(12) United States Patent
Shrager et al.

(10) Patent No.: US 11,887,738 B2
(45) Date of Patent: Jan. 30, 2024

(54) PLATFORMS FOR CONDUCTING VIRTUAL TRIALS

(71) Applicant: Cancer Commons, Palo Alto, CA (US)

(72) Inventors: Jeffrey C. Shrager, Palo Alto, CA (US); Jay Martin Tenenbaum, Los Altos, CA (US); Christopher Kelly Porter, Chapel Hill, NC (US); William Arthur Hoos, Chapel Hill, NC (US); Mark Adam Shapiro, Durham, NC (US)

(73) Assignee: CANCER COMMONS, Palo Alto, CA (US)

( * ) Notice: Subject to any disclaimer, the term of this patent is extended or adjusted under 35 U.S.C. 154(b) by 0 days.

(21) Appl. No.: 16/934,303

(22) Filed: Jul. 21, 2020

(65) Prior Publication Data

US 2020/0411199 A1 Dec. 31, 2020

Related U.S. Application Data

(63) Continuation of application No. PCT/US2019/014539, filed on Jan. 22, 2019.

(Continued)

(51) Int. Cl.
| | | |
|---|---|---|
| *G16H 50/70* | (2018.01) | |
| *G16H 40/20* | (2018.01) | |
| *G16H 15/00* | (2018.01) | |
| *G16H 50/20* | (2018.01) | |
| *G16H 70/40* | (2018.01) | |
| *G16H 10/20* | (2018.01) | |

(Continued)

(52) U.S. Cl.
CPC .............. *G16H 50/70* (2018.01); *G06F 40/58* (2020.01); *G16H 10/20* (2018.01); *G16H 15/00* (2018.01); *G16H 40/20* (2018.01); *G16H 50/20* (2018.01); *G16H 70/20* (2018.01); *G16H 70/40* (2018.01)

(58) Field of Classification Search
CPC ........ G16H 50/70; G16H 40/20; G16H 15/00; G16H 50/20; G16H 70/40; G16H 10/20; G16H 70/20; G16H 40/67; G16H 80/00; G16H 10/60; G16H 20/00; G06F 40/58
See application file for complete search history.

(56) References Cited

U.S. PATENT DOCUMENTS

| | | |
|---|---|---|
| 9,629,856 B2 | 4/2017 | Dreher |
| 2003/0036627 A1 | 2/2003 | Montelaro et al. |
| | (Continued) | |

OTHER PUBLICATIONS

International Search Report dated Apr. 15, 2019 for International Application Serial No. PCT/US2019/014539, (2 pages).

(Continued)

*Primary Examiner* — Jason S Tiedeman
*Assistant Examiner* — Liza Tony Kanaan
(74) *Attorney, Agent, or Firm* — Wilson Sonsini Goodrich & Rosati

(57) ABSTRACT

The present disclosure provides platforms, systems, media, and methods for capturing clinical cases and expert-derived treatment rationales to facilitate biomedical decision making, which can include virtual clinical trials that continuously learn from the experiences of all patients, on all treatments, and all the time. Algorithms such as Bayesian machine learning methods can be applied to coordinate such virtual trials.

17 Claims, 27 Drawing Sheets

Related U.S. Application Data

(60) Provisional application No. 62/620,365, filed on Jan. 22, 2018.

(51) Int. Cl.
*G16H 70/20* (2018.01)
*G06F 40/58* (2020.01)

(56) References Cited

U.S. PATENT DOCUMENTS

| | | | |
|---|---|---|---|
| 2003/0126101 A1 | 7/2003 | Rao et al. | |
| 2006/0121083 A1 | 6/2006 | Mor | |
| 2011/0119212 A1* | 5/2011 | De Bruin | A61B 5/369 706/12 |
| 2015/0019241 A1* | 1/2015 | Bennett | G16H 50/20 705/2 |
| 2015/0056253 A1 | 2/2015 | Bancel et al. | |
| 2016/0048655 A1* | 2/2016 | Maitra | G16H 70/40 705/3 |
| 2016/0129282 A1* | 5/2016 | Yin | G16H 20/40 600/1 |
| 2016/0224760 A1* | 8/2016 | Peták | G16H 50/70 |
| 2016/0253473 A1 | 9/2016 | Anderson et al. | |
| 2016/0357944 A1 | 12/2016 | Iyer et al. | |
| 2017/0076046 A1* | 3/2017 | Barnes | G16H 40/20 |
| 2017/0124263 A1* | 5/2017 | Crafts, Jr. | G16H 20/60 |
| 2017/0173225 A1 | 6/2017 | Troxel | |
| 2017/0323083 A1* | 11/2017 | Sablinski | G16H 10/20 |
| 2018/0046780 A1* | 2/2018 | Graiver | G06F 40/44 |
| 2018/0206778 A1* | 7/2018 | Tan | G16H 10/20 |

OTHER PUBLICATIONS

Mocellin, Simone et al. "Targeted Therapy Database (TTD): a model to match patient's molecular profile with current knowledge on cancer biology." PloS one vol. 5,8 e11965. Aug. 10, 2010, doi:10.1371/journal.pone.0011965.

Shrager, J., Tenenbaum, J. Rapid learning for precision oncology. Nat Rev Clin Oncol 11,109-118 (2014). https://doi.org/10.1038/nrclinonc.2013.244.

Won, Brian et al. "Post-crizotinib management of effective ceritinib therapy in a patient with ALK-positive non-small cell lung cancer." BMC cancer vol. 16 568. Aug. 2, 2016, doi:10.1186/s12885-016-2636-z.

Written Opinion of the International Searching Authority dated Apr. 15, 2019 for International Application Serial No. PCT/US2019/014539, (10 pages).

European Supplemental Search Report issued in EP19741532 dated Aug. 13, 2021.

* cited by examiner

FIG. 3

Quark -- Case and Insight Capture

*FOR DEMONSTRATION AND EDUCATIONAL PURPOSES ONLY; NOT TO BE USED IN CLINICAL SETTINGS; DO NOT ENTER PHI*

[TEx] [Quark] [Peer Review] [Insights in Oncology/Nano-Journal] [Trials Dashboard] [Take a Tour] [Docs]

Header info *(DO NOT INCLUDE PHI)*:

Meeting ID: [Test meeting]   Analyst's ID (or email): [Test@Test.Edu]

Meeting description: [Description of test meeting]

*DO NOT INCLUDE PHI*

[Cheatsheet] [New Case] [Add TR]

- 54 yo m; 2016:NSCLC, currently stage 4;
- Observations: EIF2AK3-ALK fusion
- Discussion: (use the ADD TR button to frame treatment rationales)
- *EIF2AK3-ALK fusion in NSCLC confers sensitivity to ceritinib (Won, Mambetsariev, and Salgia, BMC Cancer. 2016 Aug 2;16:568)

Peer Review Dashboard

FIG. 5

*FOR DEMONSTRATION AND EDUCATIONAL PURPOSES ONLY, NOT TO BE USED IN CLINICAL SETTINGS; DO NOT ENTER PHI*

[TrEx] [Quark] [Peer Review] [Insights in Oncology/Nano-Journal] [Trials Dashboard] [Take a Tour] [Docs]

All vetting input is anonymous. If you want to be contacted, you'll have to put your email, phone, etc. in a comment.
(2 'Agrees' to accept; 2 'Disagrees' to reject.)

EIF2AK3-ALK fusion in NSCLC confers sensitivity to ceritinib (Won, Mambetsariev, and Salgia, BMC Cancer. 2016 Aug 2;16:568) Search on Google Scholar

| Agreement | Generality | Evidence | Importance |
|---|---|---|---|
| ○ Disagree  ○ Neutral  ● Agree | ○ Specific  ○ Neutral  ● General | ○ Weak  ● Medium  ○ Strong | ○ Less  ● Medium  ○ Very |

[Anonymous comment if desired (NO PHI, PLEASE!)]

[Submit]

[TrEx] [Quark] [Peer Review] [Insights in Oncology/Nano-Journal] [Trials Dashboard] [Take a Tour] [Docs]

Copyright 2017 Cancer Commons. These tools were built by a team headed by Jeff Shrager, Connor Sweetnam, and Robert Baertsch. Thanks, as well, to advice and guidance from Simone Mocellin. For support or further information contact Jeff Shrager (jeff@cancercommons.org)

FIG. 6A

Insights in Oncology -- A Nano-Journal

FOR DEMONSTRATION AND EDUCATIONAL PURPOSES ONLY;

[TrEx] [Quark] [Peer Review] ['Insights in Oncology']

<< First Page

To Fig. 6B

| ID | Cancer | Alteration | Context | Relation | Treatment | Reference |
|---|---|---|---|---|---|---|
| TTD-3716222002-236 | NSCLC | EIF2AK3-ALK FUSION | efficacy | sensitivity to | Ceritinib | Won, Mambetsariev, and Salgia, BMC Cancer. 2016 Aug 2;16:568 |
| TTD-1 | Melanoma | BRAF mut V600E | efficacy | sensitivity to | 17-AAG | Da Rocha Dias S, Cancer Res 2005, 65:10686-91 |
| TTD-1000 | Melanoma | PEDF downregulated | efficacy | sensitivity to | PEDF gene therapy | Yang H, Invest Ophthalmol Vis Sci 2010, 51:28-34 |
| TTD-1007 | Melanoma | ERBB4 mut R544W | efficacy | sensitivity to | Lapatinib | Prickett TD, Nat Genet 2009, 41:1127-32 |
| TTD-1008 | Melanoma | ERBB4 mut E563K | efficacy | sensitivity to | Lapatinib | Prickett TD, Nat Genet 2009, 41:1127-32 |
| TTD-1009 | Melanoma | ERBB4 mut E317K | efficacy | sensitivity to | Lapatinib | Prickett TD, Nat Genet 2009, 41:1127-32 |
| TTD-101 | Melanoma | JUN expressed | efficacy | sensitivity to | JUN siRNA | Lopez-Bergami P, J Biol Chem 2010, 285:903-13 |
| TTD-1010 | Melanoma | ERBB4 mut E452K | efficacy | sensitivity to | Lapatinib | Prickett TD, Nat Genet 2009, 41:1127-32 |
| TTD-1011 | Melanoma | ERBB4 mut E317K | efficacy | sensitivity to | ERBB4 siRNA | Prickett TD, Nat Genet 2009, 41:1127-32 |
| TTD-1012 | Melanoma | ERBB4 mut E452K | efficacy | sensitivity to | ERBB4 siRNA | Prickett TD, Nat Genet 2009, 41:1127-32 |

<< First Page

FIG. 6B

*NOT TO BE USED IN CLINICAL SETTINGS; DO NOT ENTER PHI*

[Nano-Journal] [Trials Dashboard] [Take a Tour] [Docs]

| | | |
|---|---|---|
| clinical series | | EIF2AK3-ALK fusion in NSCLC confers sensitivity to ceritinib (Won, Mambetsariev, and Salgia, BMC Cancer. 2016 Aug 2;16:568) [Search it on Google Scholar] |
| human in vitro | - | 17-AAG is a HSP90 inhibitor |
| animal in vivo | - | Uveal melanoma. Lentivirus-mediated gene transfer of PEDF decreased the growth of ocular melanoma and its hepatic micrometastasis in a mouse ocular melanoma model |
| human in vitro | - | Melanoma cells expressing mutationally activated ERBB4 had reduced cell growth after treatment with the ERBB inhibitor lapatinib |
| human in vitro | - | Melanoma cells expressing mutationally activated ERBB4 had reduced cell growth after treatment with the ERBB inhibitor lapatinib |
| human in vitro | - | Melanoma cells expressing mutationally activated ERBB4 had reduced cell growth after treatment with the ERBB inhibitor lapatinib |
| human xenograft | - | c-JUN upregulates PDK1 transcription which increases AKT and PKC activity by phosphorylation |
| human in vitro | - | Melanoma cells expressing mutationally activated ERBB4 had reduced cell growth after treatment with the ERBB inhibitor lapatinib |
| human in vitro | - | Melanoma cells expressing mutationally activated ERBB4 had reduced cell growth after treatment with small interfering RNA against ERBB4 |
| human in vitro | - | Melanoma cells expressing mutationally activated ERBB4 had reduced cell growth after treatment with small interfering RNA against ERBB4 |

From Fig. 6A

[Next Page >]

FIG. 7A

TrEx -- The Treatment Explorer

*FOR DEMONSTRATION AND EDUCATIONAL PURPOSES ONLY;*

[TrEx] [Quark] [Peer Review] ['Insights in Oncology' N

Rankings (by overall score):

WARNING: THIS TOOL IS FOR DEMONSTRATION, RESEARCH, AND EDUCATIONAL PURPOSES ONLY. IT IS NO

To Fig. 7B

| Treatment | [lower CI, score, upper CI] |
|---|---|
| plx4032 | [1.00, 1.00, 1.00] |
| melphalan + actinomycin-d | [-0.51, -0.50, -0.49] |

Test results:

[Rank Drugs]

| Test | Positive (Aberrant/Active/Expressed/Mu |
|---|---|
| BRAF mut V600E | Positive: ● |
| CCL17 expressed | Positive: ○ |
| CCR5 polymorphism delta32 | Positive: ○ |
| CDKN2A expressed | Positive: ○ |
| CSF2R uncharacterized | Positive: ○ |
| CTLA4 polymorphism rs11571327 | Positive: ○ |
| CTLA4 polymorphism rs231775 | Positive: ○ |
| CTLA4 polymorphism rs4553808 | Positive: ○ |
| CTLA4 uncharacterized | Positive: ○ |

FIG. 7B

| | z score | serr | p |
|---|---|---|---|
| | 299.58084 | 0.0016689985 | 0.0D0 |
| | 0.0 | 0.00334692 | 1.0D0 |

NOT TO BE USED IN CLINICAL SETTINGS; DO NOT ENTER PHI

[ano-Journal] [Trials Dashboard] [Take a Tour] [Docs]

T TO BE USED IN ANY CLINICAL SETTING

| tated) | Negative (Inactive/Unexpressed/Unmutated) | Untested (Unknown/Inconclusive) |
|---|---|---|
| | Negative: ○ | Unknown: ○ |
| | Negative: ○ | Unknown: ● |
| | Negative: ○ | Unknown: ● |
| | Negative: ○ | Unknown: ● |
| | Negative: ○ | Unknown: ● |
| | Negative: ○ | Unknown: ● |
| | Negative: ○ | Unknown: ● |
| | Negative: ○ | Unknown: ● |
| | Negative: ○ | Unknown: ● |

From Fig. 7A

FIG. 10A

Age

1 ○————————○ 100

Gender

[ Choose... ▽ ]

Biomarkers +

● All  ○ Any

[ Choose... ▽ ]  X

Treatments +

● All  ○ Any

Type [ Choose... ▽ ]  X

Survival since DX

1 ○————————○ 180

Cases (717) | Tre cases > cases > cases > trea

| Id | Age at Diagnosis |
|---|---|
| 57 | 53 |
| 62 | 40 |
| 64 | 41 |
| 70 | 35 |
| 88 | 39 |
| 95 | 47 |
| 98 | 44 |
| 101 | 31 |
| 102 | 44 |
| 103 | 44 |
| 111 | 20 |
| 112 | 59 |
| 120 | 27 |
| 126 | 47 |
| 128 | 55 |

| | | | |
|---|---|---|---|
| atments | Chart | Expert Insights | Overview | tments > treatments-chart > cases > overview > cases > cases >

| Date of Diagnosis | Last ILS | Last KScore | Last KScore Date |
|---|---|---|---|
| 1996-09-27 | 1369.0 | 0 | 2000-05-01 |
| 1994-11-04 | 1561.5 | 0 | 2000-07-29 |
| 1994-01-19 | 4357.0 | 0 | 2002-10-30 |
| 1996-04-25 | 0.0 | 80 | 1997-03-12 |
| 1993-06-22 | 182.0 | 0 | 1998-04-28 |
| 1997-01-23 | 37.0 | 0 | 1997-11-30 |
| 1993-04-29 | 58322.0 | 80 | 2017-04-09 |
| 1995-09-14 | 58322.0 | 100 | 2017-04-01 |
| 1996-07-01 | 16.0 | 0 | 1997-09-02 |
| 1991-10-01 | 57840.0 | 70 | 2017-03-01 |
| 1996-03-25 | 10.0 | 0 | 1997-10-23 |
| 1996-04-15 | 121.0 | 0 | 1996-07-31 |
| 1992-10-01 | 9092.0 | 0 | 2007-09-01 |
| 1995-07-01 | 6.0 | 0 | 1997-11-04 |
| 1996-01-11 | 0.0 | 0 | 1997-05-08 |

From Fig. 10A

PLATFORMS FOR CONDUCTING VIRTUAL TRIALS

CROSS-REFERENCE

This application is a continuation of International Application No. PCT/US2019/014539, filed Jan. 22, 2019, which claims the benefit of U.S. Provisional Patent Application No. 62/620,365, filed Jan. 22, 2018, each of which is entirely incorporated by reference herein.

BACKGROUND OF THE INVENTION

An estimated 15 million Americans are currently living with cancer. The cost of developing a single new cancer drug is now around $1 billion. Traditional clinical trials account for the bulk of cancer drug development costs, and can take years to complete. Their focus on single agent therapies and need for large sample sizes may render the current developmental model practically and financially unsustainable.

SUMMARY OF THE INVENTION

The present disclosure provides systems and methods that implement a patient-centric approach to precision oncology that enables rapid global learning from every patient treatment, including an artificial intelligence (AI)-based platform.

Clinical research in oncology faces significant challenges related to the high monetary and time costs of clinical trials, in which individual outcomes vary widely and too many trials compete for too few patients. Currently, about 3,500 open immuno-oncology trials in the U.S. are competing to jointly recruit about 600,000 patients. Most of these trials will never fully accrue, since only about 50,000 patients may enroll in US cancer trials in a year. Further, there are exponentially more plausible drug combinations to test than the current trial paradigm can handle. Many thousands of patients do not receive life-saving therapies because their physicians do not know the optimal way to treat them with currently available therapies.

Even after a drug, after the investment of many years and resources, is approved and available for use, the drug is often unavailable for use in multi-therapy regimens for treating any cancer, which may be the most effective, if not the only, solution available for the patient, because no one has optimized its use in such complex multi-therapy regimens or other combination therapies. Moreover, no one has ventured to experiment on such combinatory optimization, which may amount to its own clinical trial (on a particular combination or sequence of treatments), for the same limitations that a single clinical trial is far too slow and costly to test each of tens of thousands of plausible ways to use the already available drugs in various therapies.

Recognizing this problem, incremental innovations have been explored to improve clinical trial processes, such as adaptive platform trials, siteless trials, seamless (phaseless) trials, expanded access, and real world evidence. However, these advances do not address the problem that there are not enough patients to test all the new targeted- and immuno-therapies. Using systems and methods of the present disclosure, these and other innovations are combined in such a way that the clinical trials paradigm shifts from approving drugs to curing patients.

Recognized herein is a problem that there is no data on the combinations or sequences of approved and available drugs. Further recognized herein is a problem that there is no way to optimize the use of an available drug by conducting clinical trials on different therapy regimens because there are more rational treatment hypotheses than there are patients that are available for testing of these hypotheses in trials. The present disclosure recognizes that fighting cancer is fundamentally an artificial intelligence (AI) planning and search problem that requires the coordination of multiple agents—human and computer—to work together to efficiently search the voluminous and high dimensional space of cancer molecular subtypes and treatment combinations. Thus, provided herein is a solution to at least the above-mentioned problems by providing an AI or machine learning-based virtual trial platform that can facilitate optimization of any drug that is available for use by performing and coordinating virtual trials that generate outcomes as valuable and as real as traditional clinical trials. Differentiating from other AI-based platforms (for any application) that solve big data problems (e.g., too much data), the present disclosure provides AI-based platforms that solve no data problems (e.g., not enough data). The solution may revolutionize experimental science, and the order in which we plan, search, and recognize a solution (e.g., successful therapy) for a problem (e.g., cancer).

The present disclosure provides platforms, systems, media, and methods for capturing biomedical decision reasoning such as treatment rationales and leveraging this information to improve treatment options.

Systems and methods of the present disclosure provide the ability to perform Virtual Trials, which can take adaptive platform trials to their logical extreme, continuously learning from all patients, on all treatments, all the time. Instead of performing one clinical trial per drug to gain regulatory approval, the patient-centric Virtual Trials seek to optimize each individual's outcome using all available treatments. Instead of setting up a separate trial infrastructure to test each treatment hypothesis on a pre-defined patient cohort, the Virtual Trials can maximize the information gained over all patients and use that information to dynamically define the right cohort for each drug.

In some aspects, the Virtual Trials begin with small expanded access studies of promising therapies, comprising a few patients each. Real world data can be captured and analyzed for safety and efficacy signals. The cohorts can then be seamlessly expanded for treatments that work and the cohorts can be shrunk or refined for treatments that aren't working, until enough Bayesian evidence is obtained to either seek accelerated approval or abandon the drug.

The virtual trials enabled by systems and methods of the present disclosure can overcome many of the challenges facing traditional clinical trials. For example, the platform provides a new ecosystem within which virtual trials are carried out that capture treatment and outcome data at the point of care. Doctors can enter patient and treatment information that is anonymized and then monitored to obtain outcome data, which may be used to inform future treatment decisions, thereby transforming the everyday practice of oncology into a global adaptive search for better treatments and cures. Virtual trials connect patients with expert physicians such as molecular tumor boards, and capture their treatment recommendations and rationales in a knowledge base, along with the patient's clinical results. By engaging patients and physicians at the point of care, Virtual Trials have the potential to optimize and extend the use of available therapies far more efficiently than traditional clinical trials. As a result, patients are matched to the treatments most likely to benefit them, rather than to trials that happen to be locally available. The platform can also provide an ecosystem into which anyone can submit software for performing tasks such as decision support or trial finding. Beneficially, the platform may coordinate, and interpret, every instance of treatment, individual or collectively, as part of a virtual trial or parts of multiple virtual trials. In such an ecosystem, an individual and independent treatment or study may be found to be relevant to a trial after-the-fact unlike in traditional clinical trials where the treatments and studies are rigorously pre-planned based on a presumption that they will be relevant to the trial. In some cases, a virtual trial may be created by interpreting multiple individual treatments or studies that were previously unrelated.

Systems and methods of the present disclosure provide an AI-based platform to run such "Virtual Trials." Each patient's treatment regimen is adaptively planned by a "Virtual Tumor Board" (VTB) to optimize their individual outcome. The VTBs share treatment recommendations and rationales with each other and with leading academic cancer centers. Individual treatment plans are coordinated prospectively across all patients in the network to maximize collective learning.

The AI-based platform uses a combination of expert collective intelligence, AI, and machine learning to dynamically generate and test novel personalized treatment hypotheses. The experts on a VTB collectively review each case and develop an equipoise set of options that have the strongest rationale for success. The system uses AI and ML to retrieve recommendations made for similar patients in the past, and to rank their relevance for the current case. However, the final treatment decision still remains with the patient and their physician. In the absence of physician and patient preferences, the platform can suggest treatment options from the equipoise set that maximize information gain. Treatment decisions and rationales are captured for all patients, along with regulatory-grade real-world outcomes data.

The software disclosed herein enables disseminating the patient and treatment information to other patients and professionals at the point of care such as through a software application (e.g., a virtual trial application). Users can register a new case (such as through a clinical case capture tool), and the application optionally displays treatments, trials, and/or treatment combinations that have been tried by (or hypothesized for) similar patients. The results may be sorted by most effective, most cost effective, best risk/benefit ratio, cost, least side effects, other parameter(s), or a combination thereof. The decision to try a specific therapy, alone or in combination, is typically up to the treating physician, who can consult with peers through a network linked to the knowledge base. Outcomes can be obtained by querying patients and/or physicians. In some cases, the application suggests steps to try (e.g., treatment, monitoring, further testing), based on recommendations elicited from experts and molecular tumor boards for similar cases on the knowledge base. Accordingly, the application can facilitate the rapid testing and refinement of these hypotheses by coordinating treatment decisions across cases to rapidly replicate successful strategies and discard failures. In equipoise situations, treatment recommendations can be randomized to maximize learning.

Systems and methods of the present disclosure include one or more algorithmic decision engines that can analyze the trove of information in the knowledge base and leverage the expert-derived insight to predict treatment options customized to the unique attributes of a given case. For example, the oncology drug development pipeline for a cancer such as glioblastoma contains promising targeted- and immuno-therapies, many of which have already been approved for treatment of more common cancers. These drugs are, in principle, available today off-label, in trials, and through compassionate use programs. However, no one knows the optimal way to use these "available" therapies, because they are seldom tested head to head or in combinations. Any off-label use is untracked, which often leads to patients repeatedly using ineffective combinations because their decision making is unable to leverage any off-label use data. Furthermore, where the off-label use is untracked but efficient, the details of such effective use remain unreported and thus cannot be leveraged by other subjects in need.

Systems and methods of the present disclosure include the ability to test multi-drug regimens which are problematic in clinical trials because of the vast combinatorics. For example, there are at least 4 distinct molecular subtypes of glioblastoma, and several dozen plausible therapies for treating each of them. Which interventions are optimal for treating a given individual over the course of their disease (and the sequence, schedule and dosing) present countless combinations. Current clinical trial designs, including contemporary "adaptive" Bayesian designs, cannot efficiently search this huge combinatorial space, especially given that fewer than 5% of the 20,000 GBM patients diagnosed each year participate in trials. The present disclosure provides a faster way to improve outcomes by aggregating the insights, experiences and intuitions of the best clinicians, and continuously validating and refining them based on real-world outcomes data. Every day, patients who have exhausted the standard of care are treated with off-label drugs and rational cocktails. Unfortunately, these individualized ("N-of-1") experiments are uncoordinated, and their results seldom reported, so little is learned. The platform of the present disclosure allows these results to be captured and shared with the rest of the scientific and medical community. The information is further analyzed to generate predictions such as treatment options (optionally ranked according to predicted efficacy) and/or treatment hypotheses.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings are included to provide a further understanding of the present disclosure, and are incorporated in and constitute a part of this specification. The drawings illustrate embodiments of the present disclosure and, together with the description, serve to explain the principles of the present disclosure. The diagrams are for illustration only, which thus is not a limitation of the present disclosure, and wherein:

FIG. 3 shows an illustrative example of a transcript for a MTB review of a clinical case;

FIG. 5 shows an illustrative example of a peer review interface for vetting of a treatment rationale;

FIGS. 6A-6B show an illustrative example of a nano-journal comprising a plurality of nano-publications;

FIGS. 7A-7B show an illustrative example of a treatment explorer interface allowing a user to obtain ranked treatments based on patient/treatment information;

FIGS. 10A-10B show an embodiment of a virtual trials interface allowing parameter selection to identify clinical case cohorts in the knowledge base;

DETAILED DESCRIPTION

Figure 1:
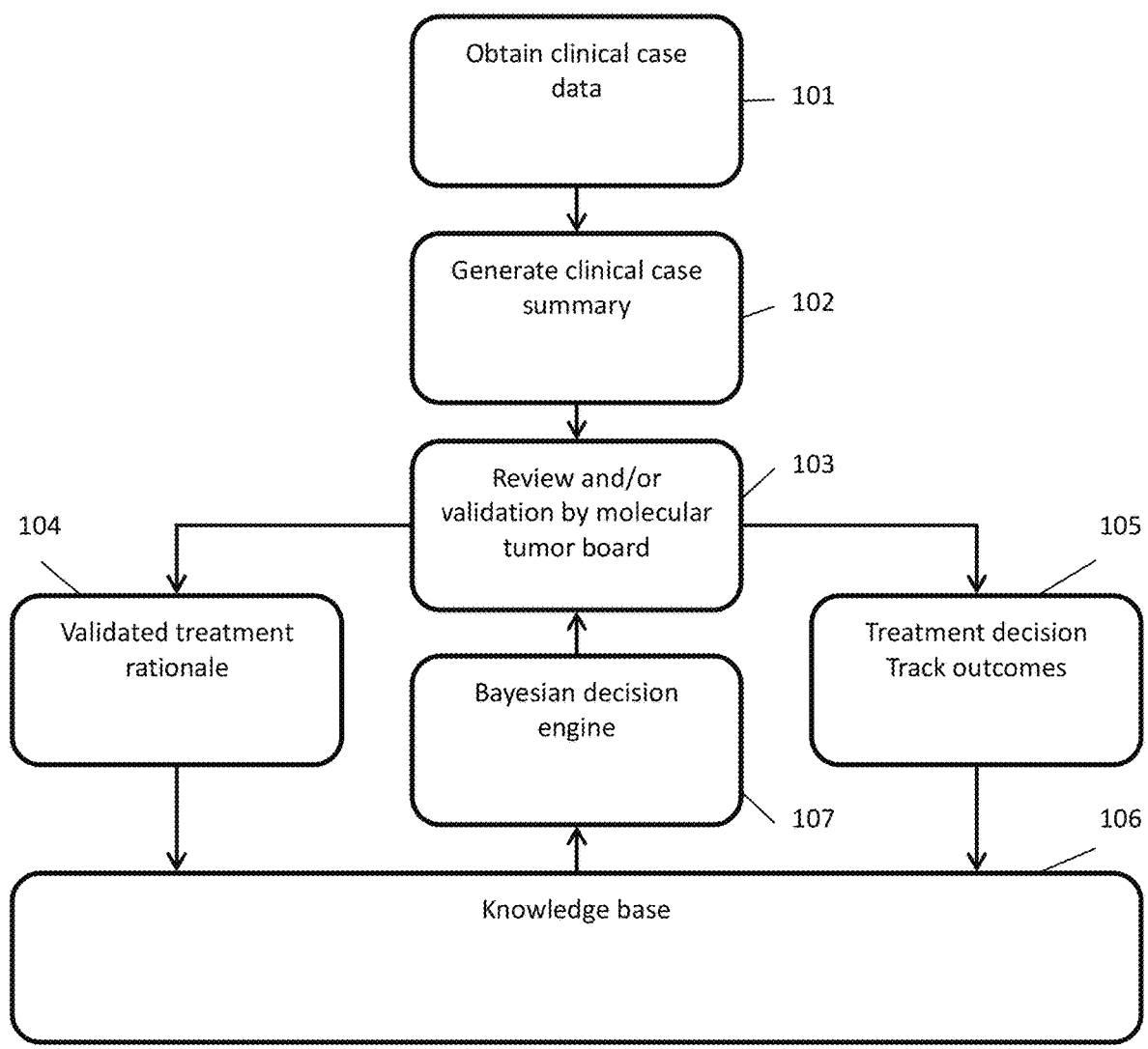
FIG. 1 shows an example process for utilizing a decision engine and molecular tumor boards to capture and analyze clinical case information.

The present disclosure recognizes that beating cancer is fundamentally an AI problem, requiring the coordination of multiple human and computer agents, working together to efficiently search the high dimensional space of cancer molecular subtypes crossed with treatment combinations. Various aspects of the present disclosure provide an ecosystem that enables the optimization of the use of currently available drugs, off-label and in cocktails. The platforms, systems, media, and methods described herein can reduce or eliminate the knowledge disparities between academic centers that see the most advanced cases, and community practices where most patients are seen; and by planning and coordinating the thousands of formal and informal treatment experiments that take place daily in oncology to optimize individual outcomes and maximize collective learning.

The optimal way to use available drugs is often unknown because the best treatments involve intelligent and contextualized combinations unique to the medical history and molecular profile of the patient, and there are far more plausible regimens than can be tested in clinical trials. Patients who have exhausted the standard of care are routinely treated with off-label drugs and rational cocktails. Unfortunately, these individualized ("N-of-1") experiments are uncoordinated, and their results seldom reported. Accordingly, the platforms, systems, media, and methods disclosed herein can facilitate the adaptive planning of each patient's treatment regimen to optimize individual outcomes, while also coordinating these plans across the patient population to maximize collective learning.

Disclosed herein are platforms, systems, applications, and methods for carrying out virtual clinical trials. The present disclosure provides the ability to obtain patient case summaries and generate and/or validate treatment rationales associated with said summaries. Individual patients or their doctors are able to input case information through a clinical case capture tool presenting selectable clinical case templates. The clinical case template may have adaptive parameters that dynamically change according to previously entered parameters to capture the unique set of information for a particular case. The completed case summary can include a treatment rationale provided by the user or trained clinicians such as those on a molecular tumor board. Alternatively, a treatment rationale can be generated as an output of an analysis of patient data. A clinician survey application enables clinicians to generate, review, and/or validate treatment rationales. The clinical survey application may receive the treatment rationale or validation thereof in the form of a Controlled Natural Language such as Biomedical Controlled English. This format allows the case information to be parsed and formatted for analysis by algorithms that utilize the validated case summaries and/or treatment rationales to generate various outputs such as suggested treatment protocols. A clinical decision engine applies one or more algorithms to identify a similar patient cohort and generate at least one treatment protocol. Each case and associated validated treatment rationale is typically monitored until an outcome of the treatment is determined. This information is then fed back into the knowledge base of system to conclude the virtual clinical trial. Thus, each patient case constitutes an "N-of-1" virtual trial, which can be captured and consolidated to provide robust results. Accordingly, the updated knowledge base can be used to further train and update the one or more algorithms. In some cases, the clinical decision engine coordinates multiple virtual trials.

Information for a subject with cancer typically can include an array of data. Examples of patient information include sex or gender, age, tumor or cancer type, cancer stage or progression, and one or more biomarkers. Such information can be entered by a user at a point of care such as a physician or patient. Additional information such as past treatments and/or responses to said treatments may be included. The patient information can make up a case summary for each patient. Such case summaries optionally include one or more treatment options and/or treatment rationales.

As used herein, a treatment option can refer to a specific treatment (e.g., active agent and/or dosing regimen) or mode of treatment (e.g., chemotherapy, surgery). Examples of treatment options include radiation, chemotherapy (e.g., adjuvant or neo-adjuvant, using specific chemotherapeutic agents, etc.), surgery, targeted therapies (e.g., monoclonal antibody treatment), hormone therapy, stem cell transplant, and immunotherapy (e.g., using immune modulators to enhance an immune response). Examples of chemotherapeutic agents include alkylating agents, plant alkaloids, anti-metabolites, anti-microtubule agents, topoisomerase inhibitors, retinoids, ribonucleotide reductase inhibitors, adrenocortical steroid inhibitors, cytotoxic antibiotics, or other agents. Examples of targeted therapeutic agents include small molecule inhibitors such as imatinib, gefitinib, erlotinib, sorafenib, sunitinib, dasatinib, lapatinib, nilotinib, bortezomib, crizotinib, obatoclax, navitoclax, iniparib, perifosine, apatinib, vemurafenib, dabrafenib, trametinib, and VAL-083. Examples of targeted therapeutic agents also include monoclonal antibodies such as rituximab, trastuzumab, alemtuzumab, cetuximab, bevacizumab, panitumumab, and ipilimumab.

As used herein, a treatment rationale refers to an explanation or rationale for why a particular treatment option or class of treatment is recommended or excluded (e.g., indicated or contraindicated). Treatment rationales generally act as explanations for treatment recommendations and represent the core content of clinical reasoning by providing the inferential connection between observations and treatment decisions. A treatment option and/or one or more associated treatment rationales can be entered by the user (e.g., patient or patient's physician) oftentimes alongside case summary information, generated using one or more predictive algorithms, or are provided by an expert clinician, researcher, or molecular tumor board when reviewing the case.

As used herein, cancer refers to diseases generally characterized by abnormal growth of cells that tend to proliferate uncontrollably. Examples of cancer can include breast cancer such as a ductal carcinoma, medullary carcinomas, colloid carcinomas, tubular carcinomas, and inflammatory breast cancer, ovarian cancer, uterine cancer, cervical cancer, prostate cancer, pancreatic cancer, bladder cancer, acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), chronic lymphocytic leukemia (CLL), multiple myeloma (MM), myelodysplastic syndrome (MDS), bone cancer, lung cancer, including non-small cell lung cancer (NSCLC), adenocarcinomas, basal cell carcinoma, melanoma, squamous cell carcinoma, liver cancer, kidney cancer, lymphoma, Kaposi's Sarcoma, cervical cancer, astrocytoma, glioblastoma, schwannomas, medulloblastomas, neurofibromas, mesotheliomas, oropharyngeal cancer, colorectal cancer, testicular cancer, thymomas, thymic carcinomas, Hodgkin disease, and non-Hodgkin lymphomas.

Molecular Tumor Boards

The treatment rationales of the present disclosure may be generated by experts in the process of reasoning about actual patients, thus capturing case-contextualized reasoning. Much of what experts know and use in regular decision-making is not published (e.g., it comes from their personal case experience) and may not even be practically or ethically testable in clinical trials. Accordingly, the methods disclosed herein enable such expert knowledge to be captured as an efficient way to focus the biomedical search.

Focusing on case-contextual reasoning provides multiple advantages. First, the case context provides the provenance for the treatment rationales (TRs), analogous to a literature citation. Second, the case context and optionally any surrounding discussion are often important in understanding the meaning and limitations of TRs and for assessing their validity and generality. Many scholars believe that knowledge deployed in an active reasoning context (e.g., "dynamic" knowledge) differs in important ways from knowledge found in papers and books (e.g., "static" knowledge) (e.g., Knorr-Cetina, 1981, Jaeger and Rosnow, 1988). Although it is not entirely understood why this difference exists, because of it, the context in which reasoning takes place is often critical to correctly interpreting and using what was said.

Only a miniscule fraction of cases that may represent useful treatment rationales are likely to end up in published case reports. Although treatment rationales regularly arise in live clinical problem solving, and are regularly voiced in discussion among physicians, such rationales rarely end up in medical records, and are almost never shared in detail with patients. This is particularly true for rejected treatment hypotheses and the reasons for their rejection, even though these may be critical for understanding the pros and cons, and eventually the success or failure, of various treatment options (e.g., Youngs, et al. 2014).

The reasoning underlying clinical problem-solving about difficult cases is commonly discussed in the expert problem-solving settings that are often referred to herein as "molecular tumor boards" (MTBs), which are now commonly mounted at major cancer centers. In creating treatment recommendations, MTBs integrate a wide range of knowledge, including information that forms the content of TRs, such as: details of tumor omics, histopathology, clinical history, patient preferences, economics, ethics, and other factors. MTBs often consult experts in bioinformatics, genomics, molecular biology, and other domains. As a result, the content of MTB discussions often contains unique knowledge that may significantly inform cancer research and clinical care. Moreover, knowledge dynamically deployed in the live problem-solving contexts, such as in MTBs, is often not the same as the static explicit knowledge available directly from papers. Unfortunately, the knowledge deployed during MTB reasoning is rarely captured and communicated in either case reports or case series. More often than not, these cases end up in an EMR, where they may eventually serve as evidence in an aggregated analysis. But EMR records rarely include the richness of clinical reasoning typical of the MTB discussion, or of published case reports, and in particular are unlikely to include the reasons that some treatments were considered but reasoned to be contraindicated, and so rejected.

The present disclosure leverages the clinical reasoning captured from live MTB discussions as a valuable new source of data. Among other functions, the capture of TRs from MTBs may help to focus the hypotheses tested in clinical trials, reducing the number of trials required to efficiently search the treatment space. MTB reasoning may also help to guide the development of tools to assist in clinical decision-making. In some cases, MTB reasoning serves as expert reasoning model(s) for clinical education. Moreover, MTBs see only the most difficult cases—usually cases where the patient has exhausted the standard of care, and often cases for which there is no appropriate clinical trial. In some instances, the platforms, systems, media, and methods disclosed herein comprise components configured for capturing, vetting, and sharing MTB reasoning in the form of de-identified case summaries and case-contextualized TRs, sourced from molecular tumor boards. Such information may be analyzed to generate models and train classifiers for predicting treatment options and/or outcomes for new clinical cases.

The present disclosure provides machine learning algorithms to process the TRs generated by various entities, such as the abovementioned MTBs. Contextual information (e.g., factors considered in MTB discussions, patient history, treatment history, physician's prior personal experience, ethical considerations, etc.) for the TR may be inputted, for example, as metadata. In some cases, such machine learning algorithms may determine which contextual information, if any, was relevant to generating a new TR or relying upon a presented TR. The machine learning may be directly or indirectly trained by the same entities forming such rationales, such as the experts in the molecular tumor boards, or different entities, such as those physicians acting upon a recommended TR, by tracking an outcome of the patient and maintaining closed-loop feedback. In some instances, even a selection of a particular recommended TR, or duration of time taken to select the particular recommended TR, from a plurality of recommended TRs may be used as feedback to train the machine learning algorithms. The machine learning algorithms may be based on a Bayesian model, as described elsewhere herein. Alternatively or in addition, the machine learning algorithms may employ any combination of classification modeling, clustering techniques, predictive modeling, neural networks, validation learning, reinforcement learning, statistical dimensional reduction, and/or other techniques. Alternatively or in addition, the machine learning algorithms may be unsupervised, such as to generate its own treatment rationale(s) based on processing and analyzing big data (e.g., both raw and processed) collected from patients or from various publications.

Treatment Rationales

A treatment rationale (TR) typically represents an explanation of the actual (or supposed) reason that particular treatments or classes of treatments were recommended or excluded (e.g., indicated or contraindicated). Treatment rationales can act as explanations for treatment recommendations and represent the core content of clinical reasoning, providing the inferential connection between observations and decisions. In some cases, the TRs described herein are the products of clinical assessment by domain experts (e.g., clinicians or scientists or groups of them such as molecular tumor boards), and can codify the justification for a selection of one or more treatment options applicable to the patient being treated, based upon some presumably relevant characterization of the state of the patient's disease.

In addition to molecular characteristics of a tumor, TRs often include other factors such as economics (e.g., the costs of the treatment, the patient's insurance), patient preference, ethical factors, and even physician personal experience and taste. These factors are difficult to capture when only looking at measured outcomes, and are difficult to organize clinical trials around. However, the virtual clinical trial format provided by the present disclosure enables such factors to be analyzed and incorporated into the medical decision making process. Treatment rationales can be entered as controlled natural language or biomedical controlled English (BCE), which may be efficiently processed or converted into a format amenable to computerized manipulation and analysis.

The present disclosure provides one or more parsers for processing BCE treatment rationales into a computerized format suitable for analysis according to the methods described herein. In some cases, the range of BCE handled by the prototype implementation is narrow and focused almost uniquely on what is needed for use by the treatment explorer or the decision engine. A parser may be implemented using a simple open source language parser such as those described in Principles of AI Programming, called "simple2" and downloadable at http://norvig.com/paip/syntax2.lisp. The core of the simple2 parser is one Lisp function, called extend-parse. The grammar for the BCE treatment rationales comprises a plurality of rules and typically derives the vocabulary from the National Cancer Institute (NCI) Thesaurus—allowing a wide range of BCE TRs to be understood using just a small rule set. In some cases, the grammar comprises at least about 5, 10, 15, 20, 25, 30, 35, 40, 45, 50, 60, 70, 80, 90, or 100 rules, including increments therein, and/or no more than about 5, 10, 15, 20, 25, 30, 35, 40, 45, 50, 60, 70, 80, 90, or 100 rules, including increments therein. The grammar rules are automatically generated using machine learning methods, manually generated (e.g., when there are insufficient examples to adequately train a machine learning algorithm), or using both types of methods (e.g., using example data to train some rules, and manually generating rules that have insufficient data to train a robust rule).

Examples of treatment rationales include the following: EIF2AK3-alk fusion in NSCLC confers sensitivity to ceritinib, as demonstrated in a randomized controlled trial with 200 patients with stage 4 lung cancer (Won, Mambetsariev, and Salgia, BMC Cancer. 2016 Aug. 2; 16:568); this 50-year-old male's stage 4 NSCLC tumor was apparently sensitized to ceritinib by an EIF2AK3-alk fusion.

Example processed data components of hypothetical treatment rationales are listed in Table 1.

TABLE 1

| Case No. | Source | Molecule | State (molecule) | Relationship | Drug 1 | Drug 2 | Model |
|---|---|---|---|---|---|---|---|
| 1 | Breast cancer | HER2 | Expressed (high) | Sensitivity to | trastuzumab | | Human |
| 2 | Breast cancer | HER2 | Expressed (low) | No relationship with | trastuzumab | | Human in vitro |
| 3 | Breast cancer | HER2 ER PR | Expressed (low) | No relationship with | trastuzumab | | Human in vitro |
| 4 | Breast cancer | HER2 ER PR | Expressed (low) | Sensitive to | vantictumab | | Human |
| 5 | Breast cancer | HER2 ER PR | Expressed (low) | Sensitive to | atezolizumab | nab-paclitaxel | Human |

The example processed data components shown in Table 1 are non-limiting examples. Such data components can include additional information such as further notes or comments on the treatment rationale for the indicated treatments. For example, case number 5 details a patient with breast cancer having a triple negative molecular profile (HER2/ER/PR negative). The entry indicates sensitivity to a combination therapy using the monoclonal antibody atezolizumab and the chemotherapeutic agent paclitaxel. Further details on the treatment rationale may include an explanation that the atezolizumab antibody targets the PD-L1 marker expressed by some tumor cells that deactivates T-cells. The antibody thus prevents the tumor cells from evading T-cells by neutralizing PD-L1. The reason for also using paclitaxel is that the chemotherapeutic agent kills tumor cells, which results in the release of tumor antigens that provoke an immune response. Thus, the combination of preventing immune escape (atezolizumab) and enhancing the immune response (pactlitaxel) may produce a synergistic effect stronger than the additive effect of either therapeutic agent alone. Just knowing the molecular profile of a tumor may not provide the whole picture of why such a combination treatment may be effective. For example, it may not be clear whether such an effect is unique to breast cancer. However, the provided comments may support a treatment hypothesis that a non-breast tumor that is PD-L1 positive may benefit from this therapy. Thus, this information may be taken into account when identifying cohorts or case series such as by ignoring or diminishing the importance of cancer source when grouping case number 5 with similar cases (e.g., for conducting virtual trials on cohorts of similar cases).

Controlled Natural Language

Current machine learning and big data methods for deriving biological insight may be unable to effectively leverage the expertise and experience of skilled clinicians such as those on molecular tumor boards. Other proposed methods have sought to analyze treatments that arise from the patient's molecular data, attempted treatment(s), and observed outcome. The present disclosure provides treatment rationales generated by experts such as molecular tumor boards in the context of case-contextualized reasoning relating to real clinical cases. Such treatment rationales, however, can be difficult to interpret using existing algorithmic methods and can introduce additional complexity into any platform attempting to analyze and utilize this information. Accordingly, the present disclosure provides methods providing treatment rationales in a controlled natural language format such as biomedical controlled English (BCE).

In order to efficiently capture the unambiguous meaning of the case-contextualized treatment rationales generated by molecular tumor boards, the platform described herein focuses on "Biomedical Controlled English" (BCE), a biomedically-specific form of Controlled Natural Language (CNL; Kuhn, 2014). CNL is a domain-specific subset of natural English that is obtained by restricting the grammar and vocabulary in order to reduce or eliminate ambiguity and complexity. CNLs are commonly utilized by industry and the military to write manuals and other texts that can be automatically translated into many different languages. One of the important advantages of CNL is that it is both easily readable by humans due to being a version of a natural language, and also enables correct compilation such as automatic translation to a formal representation for computational analysis. Moreover CNL can capture everything that can be said in a natural language. In software engineering terms, CNL is referred to as a "non-lossy" formal language—that is, one does not have to drop some things on the floor in translation that one may almost certainly have to drop in the compilation step. As a result of these properties, physicians can vet TRs expressed in CNL, and the data can be automatically coded into semantics for computerized search, and other functions.

The utilization of case-contextualized treatment rationales in combination with capturing these treatment rationales in a CNL such as biomedical controlled English that is amenable to efficient encoding for computerized analysis provides a technical solution for leveraging such expert-derived, case-contextualized treatment rationales to provide patients and doctors with data-driven, case-based decision support. Without the use of a CNL, such treatment rationales may be too complex to be effectively and accurately parsed and analyzed algorithmically, and the data set too expansive for manual processing and analysis.

Treatment Outcomes

The present disclosure is not bound by the assumption that clinical cases require final outcomes in order to develop clear treatment choice statistics with the best examples being high-powered, randomized, controlled trials. Such a requirement leads to the loss of an abundance of data that includes both direct and indirect outcomes. Direct outcomes can come from long term survival data (whether in an individual case, or in a trial context), but is often more accessible in short term proxy treatment responses, such as slowing of disease progress measured by, for example, reduction in tumor load. Even though these are not complete replacements for overall survival, such data can be carefully interpreted with an understanding of their limitations to obtain biological insight. Another available source of direct outcomes is the patient history. A patient showing up for second, third, or fourth line treatment has, by definition failed (and perhaps temporarily succeeded) on previous treatments. These are valuable outcomes data that may be used by the methods disclosed herein.

Moreover, there are indirect outcomes data present in treatment choices arrived at by experts such as in treatment rationales. Domain experts' choices, and their explanations for these choices, contain indirect outcome data because experts, by definition, have "good reasons" for making choices, and these "good reasons" bring together retrospective outcomes information (whether published, personally experienced, or even mere hearsay). The methods disclosed herein allow such indirect outcome data to be leveraged in various ways (e.g., by the decision engine) such as by helping generate treatment hypotheses, deciding on treatment options, and coordinating ongoing clinical cases (e.g., virtual trials).

Coordination Platform

Despite its collective wealth of expertise and experience, the biomedical community currently lacks an effective method for communicating and coordinating the efforts of its members. Direct collaboration between members in such a large community is inefficient. However, many complex systems organize themselves efficiently by coordination rather than collaboration—what amounts to indirect collaboration. In commercial aviation, for example, pilots are strongly discouraged from talking to other pilots to avoid cluttering the airwaves with chatter. Instead pilots talk almost exclusively to controllers. The controllers have a larger view of what is going on in the system, and can coordinate traffic by guiding the pilots with recommended actions. It is, of course, the pilots who have their hands on the actual controls, and make the final decisions. But collaboration between pilots only takes place indirectly as a result of the pilot-controller interaction. Similarly, disclosed herein are platforms that coordinate indirect collaboration within the biomedical community so as to avoid multi-way communication chaos. Many medical treatments are naturally occurring, uncoordinated, and off-trial attempts by doctors to treat patients who have not responded to standard treatments. The present disclosure provides methods for capturing and coordinating such clinical cases. This approach is predicated on the assumption that more data is better than less data even if the collected data is not from prospective, randomized, or controlled trials. This assumption asserts that a large number of prospective adaptively coordinated individual cases studies can be as statistically strong, or perhaps even stronger and more efficient, than large scale, randomized, controlled clinical trials. Accordingly, one may not need to run trials at all, but rather just efficiently coordinate and collect the results of these experiments carried out across the clinical oncology community. In addition, the present disclosure provides for both individual cases as well as large scale trials and retrospective and/or prospective studies.

In some embodiments, the platform comprises a decision engine that prospectively and adaptively coordinates treatment decisions across all patient encounters. In some cases, the platform runs as a cloud-based platform accessible by various users/parties such as patients or their physicians, clinicians, bioinformaticians, research scientists, or molecular tumor boards. Prospective adaptive coordination (a) avoids unnecessary replication of either positive or negative experiments, (b) maximizes the amount of information obtained from every encounter, and (c) permits efficiently testing causal hypotheses. In some cases, prospective adaptive coordination is achieved by re-sorting treatment options based on relevant information such as test results to reflect the prospective information value of each test. The value of each test may be determined by applying one or more algorithms to current clinical case data in the knowledge base to calculate a value such as a score for a given test. For example, a given test may identify the presence of biomarkers that may point towards effective treatment options available for cancers with this molecular profile, and thus may be assigned a high and/or positive score relative to less informative tests.

Knowledge Base

The present disclosure provides for a knowledge base that can be rapidly updated with vetted TRs being fed from MTBs via case-contextualized BCE TR capture, and optionally feeding into the MTB via decision support tools (e.g., assembling cases into cohorts for virtual trials, generating ranked treatment options). In some cases, new information such as vetted TRs are "published" using a method of "nano-publication" that can offer linked data, API access, versioning, automatic re-distribution, provenance, and/or other desirable properties (Veltrop, 2010, Kuhn et al., 2016).

The TRs can be published to the knowledge base such as in a nano-journal. Such nano-publications are generally formatted in a CNL such as BCE and optionally include any number of additional annotations and translations. The BCE form of TRs provides a format that has been vetted and is "non-lossy", whereas any current version of natural language processing (NLP) compilation that tries to create a formal representation from the BCE can likely lose information. Therefore, one may start from the original, vetted, non-lossy BCE.

A variety of different targeted translation (compilation) processes may be used to compile the BCE TRs into a computable representation. For example, an analysis that tags concepts with ontological identifiers may facilitate deep similarity search, allowing users to explore a collection of ACRs by combining search terms with ontology-based filters, while a different analysis may look for drug-biomarker correlations in the TRs. The BCE is analogous to the programming language level of representation. This level that defines the program, and then various different analyses compile to different targets for different purposes, for example, running on different hardware. But one can always refer back to the BCE as validated by the vetting process as the agreed definition of what was expressed.

The knowledge base generally maintains TRs with provenance linkages to their sources such as journal publications or case-based TRs from tumor boards. In the case of case-based TRs, the TR may include clickable or selectable options for accessing the tumor board transcript (e.g., in BCE) or the relevant publication. When citations are entered into the knowledge base with TRs, the entry may contain a mechanism to search for the mentioned publication via a search engine such as Google Scholar.

Big Data

The methods described in the present disclosure are compatible with "big data" such as whole-genome sequencing, RNA-Seq, proteomic, transcriptomic, metabolomic, or other-omic data. The methods of the present disclosure address inefficiencies in the big data approach to medicine which arises due to the high dimensionality of the problem (e.g., large feature space and small sample size), and the cost of data gathering (e.g., in terms of time, economics, and/or ethical terms such as pain and suffering). As a result, the number of independent observations (sometimes referred to as the "n" of a study) is generally much smaller than the dimensionality of the data—that is, there is lots of data about very few patients. Accordingly, typical "big data" is "tall, thin, and cheap," having many rows (large n, e.g., large number of independent observations) for relatively few columns (dimensions), whereas biomedical "big data" is generally "short, fat, and expensive," having lots of columns (dimensions) for few rows (small n). Hypothesis formation in a "short, fat, expensive" data setting requires a different approach than for the "tall, thin, cheap" variety, but typical "big data" approaches are designed for the latter, not the former. There are many ways that data can be "folded" to reduce its dimensionality. For example, reducing 3 trillion bases of DNA sequence information into symbols representing around 20,000 genes, reducing these even further to only note aberrations, using pathway models to relate columns to one another, and even empirically finding correlations between columns. The expert-sourced case-contextualized TR approach described herein gathers a novel category of knowledge that can feed into the folding of the data dimensionality (columns, e.g., dimensions of the characteristic space), and also contributes to increasing the sample size by incorporating clinical cases that are normally never captured. For example, captured treatment rationales can leverage domain expert insights to focus on the most relevant dimensions of the problem.

Algorithms and Machine Learning Methods

Various algorithms can be used to generate models that predict one or more treatment options for a clinical case and/or a cohort comprising at least one clinical case. In some instances, machine learning methods are applied to the generation of such models. In some cases, a model predicts the outcome for one or more treatment options with higher accuracy than a heuristic method, and optionally provides a confidence level of the prediction. Such models can be generated by providing a machine learning algorithm with training data in which the expected output is known in advance, e.g., an output in which it is known that a clinical case having a specific data set (e.g., patient information and treatment information) achieved a particular outcome or a probability in which a particular outcome was achieved within a known group of clinical cases having specific data sets.

In some instances, machine learning methods are applied to select, from a plurality of models generated, one or more particular models that are more applicable to certain treatment options, certain types of diseases (e.g., different types of cancer), and/or certain patients. For example, a more aggressive model which makes benefit-heavy assessments may be applied to a patient that has a predicted life span below a predetermined threshold (e.g., 3 months, 1 year, 3 years, 10 years, etc.) and recommend more high-risk, high-benefit treatment options to the patient. Conversely, a less aggressive model may make risk-heavy assessments and exclude the high-risk, high-benefit treatment options from any recommendations to a patient who has a higher predicted life span. In other instances, different predictive models (using different techniques) may be generated for analyzing treatment rationales directed to different types of diseases. For example a classification regression technique may be more suitable for analyzing the knowledge base sector relevant to a first type of cancer and a clustering technique may be more suitable for analyzing the knowledge base sector relevant to a second type of cancer.

The training data for the machine learning algorithms can be provided as follows. Clinical cases with known outcomes can be grouped into cohorts based on patient information and/or treatment information. For example, patient information can include patient age, gender, cancer type, cancer stage, site of origin of (primary) tumor, site of metastasis (if available), one or more morphological features, tissue type, test results for one or more disease markers (e.g., determined using immunohistochemistry, qPCR/qRT-PCR, genetic sequencing, flow cytometry, or other laboratory techniques), or other relevant information. The site of origin of the tumor can be lung, pancreas, colorectal, breast, ovarian, prostate, kidney, stomach, brain, esophagus, liver, gallbladder, larynx, pharynx, bladder, bile ducts, or other source. In some cases, the cancer has a hematologic origin such as lymphoma, leukemia, or multiple myeloma. Treatment information can include any past or present treatment administered to the patient (including non-treatment or placebo), any corresponding treatment rationale associated with the treatment, and any outcome of the treatment. Examples of outcomes include survival rate (e.g., disease-free survival, progression-free survival, 5-year survival rate), remission, tumor size (e.g., shrinkage, remains the same, grows), metastasis, recurrence, or other prognostic metrics. In some cases, outcomes account for changes to treatment due to unforeseen or unexpected events such as complications arising from treatment such as adverse response to the treatment that forces discontinuation of treatment, hospitalization, or other alteration of the treatment regimen.

The classifier or trained algorithm of the present disclosure can comprise one feature space. In some cases, the classifier comprises two or more feature spaces. The two or more feature spaces may be distinct from one another. Each feature space can comprise types of information about a case, such as biomarker expression or genetic mutations. The accuracy of the classification may be improved by combining two or more feature spaces in a classifier instead of using a single feature space. The patient and treatment information generally make up the input features of the feature space and are labeled to indicate the classification of each case for the given set of input features corresponding to that case. In many cases, the classification is the outcome of the case. For example, a case may include more than one classification/outcome (e.g., a case may have an outcome that includes successful 5-year survival and tumor shrinkage). The training data is fed into the machine learning algorithm which processes the input features and associated outcomes to generate a model or prediction engine. In some cases, the machine learning algorithm is provided with training data that includes the classification (e.g., treatment option, outcome, etc.), thus enabling the algorithm to "learn" by comparing its output with the actual output to modify and improve the model. This is often referred to as supervised learning. Alternatively, in some instances, the machine learning algorithm is provided with unlabeled or unclassified data, which leaves the algorithm to identify hidden structure amongst the cases (e.g., clustering). This is referred to as unsupervised learning. Sometimes, unsupervised learning is useful for identifying the representations that are most useful for classifying raw data (e.g., identifying features that help separate cases into separate cohorts). For example, unsupervised learning may identify hidden patterns such as relationships between certain features and treatment rationales from the data in the knowledge base that may not be readily apparent to trained clinicians.

One or more sets of training data may be generated and provided to a decision engine comprising one or more algorithms for making predictions. An algorithm may utilize a predictive model such as a neural network, a decision tree, a support vector machine, or other applicable model. Using the training data, an algorithm can form a classifier for classifying the case according to relevant features. The features selected for classification can be classified using a variety of viable methods. In some embodiments, the trained algorithm comprises a machine learning algorithm. The machine learning algorithm may be selected from the group consisting of a supervised, semi-supervised and unsupervised learning, such as, for example, a support vector machine (SVM), a Naïve Bayes classification, a random forest, an artificial neural network, a decision tree, a K-means, learning vector quantization (LVQ), self-organizing map (SOM), graphical model, regression algorithm (e.g., linear, logistic, multivariate, association rule learning, deep learning, dimensionality reduction and ensemble selection algorithms. In some embodiments, the machine learning algorithm is selected from the group consisting of: a support vector machine (SVM), a Naïve Bayes classification, a random forest, and an artificial neural network. Machine learning techniques include bagging procedures, boosting procedures, random forest algorithms, and combinations thereof. Illustrative algorithms for analyzing the data include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis.

A trained algorithm or classifier may employ information from any part of the information from a training data set. The classifier can be tested using data that was not used for training to evaluate its predictive ability. The predictive ability of the classifier can be explained using various metrics. These metrics include accuracy, specificity, sensitivity, positive predictive value, negative predictive value, which are determined for a classifier by testing it against a set of independent samples (cases). True positive (TP) is a positive result that detects the condition when the condition is present. True negative (TN) is a negative result that does not detect the condition when the condition is absent. False positive (FP) is a result that detects the condition when the condition is absent. False negative (FN) is a test result that does not detect the condition when the condition is present. Accuracy is defined by the formula: accuracy=(TP+TN)/(TP+FP+FN+TN). Specificity ("true negative rate") is defined by the formula: specificity=TN/(TN+FP). Sensitivity ("true positive rate") is defined by the formula: sensitivity=TP/(TP+FN). Positive predictive value (PPV or "precision") is defined by the formula: PPV=TP/(TP+FP). Negative predictive value (NPV) is defined by the formula: NPV=TN/(TN+FN). In some instances, a trained classifier has an accuracy of at least about 70%, 75%, 80%, 85%, 90%, 95% or more for at least about 1, 2, 3, 4, 5, 6, 7, 8, 9, 10, 15, 20, 25, 35, 40, 45, 50, 60, 70, 80, 90, 100, 110, 120, 130, 140, 150, 160, 170, 180, 190, or 200 independent samples, including increments therein. In some instances, a trained classifier has a specificity of at least about 70%, 75%, 80%, 85%, 90%, 95% or more for at least about 1, 2, 3, 4, 6, 7, 8, 9, 10, 15, 20, 25, 30, 35, 40, 45, 50, 60, 70, 80, 90, 100, 110, 120, 130, 140, 150, 160, 170, 180, 190, or 200 independent samples, including increments therein. In some instances, a trained classifier has a sensitivity of at least about 70%, 75%, 80%, 85%, 90%, 95% or more for at least about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, or 200 independent samples, including increments therein. In some instances, a trained classifier has a positive predictive value of at least about 70%, 75%, 80%, 85%, 90%, 95% or more for at least about 1, 2, 3, 4, 5, 6, 7, 8, 9, 10, 15, 20, 25, 35, 40, 45, 50, 60, 70, 80, 90, 100, 110, 120, 130, 140, 150, 160, 170, 180, 190, or 200 independent samples, including increments therein. In some instances, a trained classifier has a negative predictive value of at least about 70%, 75%, 80%, 85%, 90%, 95% or more for at least about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, or 200 independent samples, including increments therein.

FIG. 1 shows an example process for utilizing a decision engine and molecular tumor boards to carry out analysis of clinical cases. The process shows a continuous and self-reinforcing process by which new clinical cases are entered into the system 101. These cases are reviewed and/or validated by one or more molecular tumor boards 102, which may involve generation or validation of treatment hypotheses, treatment options, treatment rationales, or a combination thereof. Molecular tumor boards are generally composed of domain experts such as clinicians, researchers, and bioinformaticians. In some cases, treatment information such as treatment options are generated by the decision engine 107 using the knowledge base and presented to the molecular tumor board for consideration during the evaluation of a case. The decision engine can coordinate decisions across multiple patients to optimize learning (e.g., a multi-armed bandit problem) while also optimizing each patient's outcome. Once the molecular tumor board has reviewed a given case, the attending physician or healthcare professional at the point of care may decide with the patient on a particular treatment option 105 (e.g., according to a treatment recommendation made by the molecular tumor board). In some cases, the treatment decision is not an actual treatment but instead a decision to run one or more tests, or to monitor the patient. This treatment decision is stored, and the case is then monitored for any additional information such as outcome data with all the information stored in the knowledge base 106. The information in the knowledge base 106 can include published cases (e.g., mined from journal articles), ask cases (e.g., cases entered by members of the network/community), and tumor board cases (e.g., includes complex cases reviewed by molecular tumor boards). The knowledge base 106 can also have data such as from the CC registry, NHS data, or partner registries. Likewise, the validated treatment rationales 104 are also stored in the knowledge base. The decision engine 107 can learn using information from the knowledge base 106 (e.g., using knowledge base data as the prior for determining a posterior probability distribution).

Figure 2:
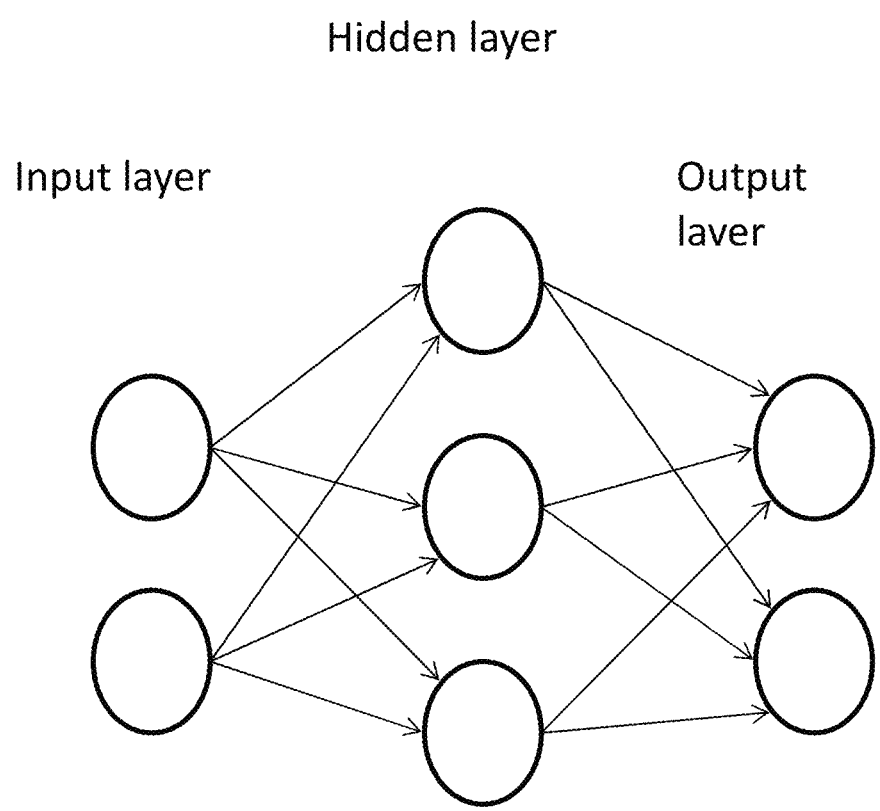
FIG. 2 shows an example neural network that may be used to carry out machine learning algorithms described herein.

Although FIG. 1 shows a Bayesian decision engine, this is an example embodiment, and non-Bayesian decision engines may be used for performing the methods described herein. The information in the knowledge base can be used to generate prior probabilities for use by the Bayesian decision engine to calculate the posterior probabilities (e.g., of one or more treatment outcomes). As the clinical cases are monitored, some can achieve one or more outcomes (e.g., remission, 5-year survival). This new data is added to the knowledge base 106 and incorporated into the analysis by the Bayesian decision engine. The process may use a Bayesian network. In some cases, the process uses an artificial neural network as shown in FIG. 2 as a machine learning method. However, it must be noted that other machine learning methods such as support-vector machines (SVMs), decision trees, and other methods can also be utilized.

Artificial neural networks such as the one shown in FIG. 2 mimic networks of neurons based on the neural structure of the brain. They process records one at a time, or in a batch mode, and "learn" by comparing their classification of the case (which, at the outset, may be largely arbitrary) with the known actual classification of the case. Artificial neural networks are typically organized in layers which comprise an input layer, an output layer, and at least one hidden layer, wherein each layer comprises one or more neurons or nodes. Some artificial neural networks comprise at least one, two, three, four, five, six, seven, eight, nine, or ten hidden layers and/or no more than one, two, three, four, five, six, seven, eight, nine, or ten hidden layers. Each node in a given layer is usually connected to the nodes in the preceding layer and the nodes in the subsequent layer. Typically, a node receives input from the neurons in the preceding layer, changes its internal state (activation) based on the value of the received input, and generates an output based on the input and activation that is then sent towards the node in the subsequent layer. The connections between neurons or nodes are represented by a number (weight) which can be positive (indicative of activating or exciting the subsequent node) or negative (indicative of suppression or inhibition of the subsequent node). A larger weight value indicates a stronger influence the node in a preceding layer has on the node in the subsequent layer. Accordingly, the input propagates through the layers of the neural network to generate a final output classification such as, for example, a value for one or more treatment options represented by neurons in the output layer. As an example, the output layer may comprise a node corresponding to surgery and a node corresponding to chemotherapy. The output can be ranked according to the values of these respective nodes (which are typically normalized to a value between 0 and 1). In a case where the node corresponding to surgery has a value of 0.9 while the node corresponding to chemotherapy has a value of 0.1, the output can be ranked with surgery as the number one treatment option and chemotherapy as the number two treatment option. In some cases, treatment options are not ranked and/or presented when they fall below a minimum significance threshold. In some instances, a threshold is a normalized value of about 0.1, 0.2, 0.3, 0.4, 0.5, 0.6, 0.7, 0.8 or 0.9, including increments therein.

The input nodes may correspond to selected parameters relevant to the output. For example, input nodes may correspond to patient age, gender, tumor type, or other patient/ cancer/treatment parameters. In some cases, the errors from the initial classification of the first record are fed back into the network, and are used to modify the network's algorithm in an iterative process.

The neural network can be trained using the training data described herein. As shown in FIG. 2, a neuron or node in an artificial neural network is present in one of the input, output, or hidden layers. A neuron typically has a set of input values ($x_i$) and associated weights ($w_i$) and a function (g) that sums the weights and generates an output (y) based in part on the input values, weights, and function. A bias (constant term) is also provided to each neuron. The input layer is composed of nodes containing the values in the data that constitute inputs for the next layer of nodes. The next layer is called a hidden layer of which there may be several. The final layer is the output layer, and may have one node for each classification. A single run forward through the network using a sample (e.g., a clinical case) produces a value for each output node, and the class label is often assigned to the output node with the highest value.

During training, the correct class for each case is known (supervised training), and the output nodes can therefore be assigned the correct values (e.g., 1 for a correct class and 0 for incorrect/others). This allows a comparison to be made between the neural network's calculated values for the output nodes to the correct or known values. Accordingly, an error may be calculated for the output nodes and then are used to adjust the weights in the hidden layers so that the output values may converge towards the correct values as the network is trained through successive rounds using the training data. The neural network uses an iterative learning process in which data cases (e.g., clinical cases) are presented to the network one at a time, and the weights associated with the connections between layers are adjusted each time. For example, a node that is found to have low relevance or impact on a node in a subsequent layer may have a connection weight that decreases through the course of training, thus reflecting its weak relationship with the other node.

Advantages of neural networks include high noise tolerance and the ability to classify patterns on which they have not been trained. One example of a neural network algorithm is a back-propagation algorithm, such as Levenberg-Marquadt.

During training, the neural network typically processes the records in the training data one at a time, using the weights and functions in the hidden layers, then compares the resulting outputs against the desired outputs. Errors are then propagated back through the system, causing the system to adjust the weights for application to the next record to be processed. This process occurs over and over as the weights are continually tweaked. During the training of a network the same set of data may be processed many times as the connection weights are continually refined. Where predictive treatment options are provided, such predictive treatment options may be assigned a predicted outcome score for each of one or more outcomes (e.g., 1 for 3 month survival, 0.8 for 5 year survival, 0.1 for 10 year survival, etc.) based on the cumulative training of the neural network, and recordation of actual outcome may be provided for comparison, the differential of which may be propagated back through the system to iteratively train the neural network for higher accuracy. In some instances, for a Bayesian decision engine, a plurality of historical actual outcome data may be compiled to assess the accuracy of a probability prediction.

The platforms, systems, media, and methods described herein can be implemented using probabilistic programming. Probabilistic programming languages are designed to describe statistical models and draw inferences based on those models. Examples of probabilistic programming languages include bayesloop, probabilistic-C, PSQL, Alchemy, ProBT, Gamble, Tuffy, WebPPL, and Pyro. In some cases, Bayesian programming is used for specifying probabilistic models and drawing inferences based on incomplete information. Examples of such models include Bayesian networks such as dynamic Bayesian networks, Kaman filters, and hidden Markov Models. Bayesian statistics may use Markov chain Monte Carlo methods such as random walk Monte Carlo (e.g., reversible jump, slice sampling, Gibbs sampling, Metropolis-Hastings, and multiple-try metropolis), training-based Markov chain Monte Carlo, and hybrid Monte Carlo methods. In some cases, the decision engine utilizes Bayesian Monte Carlo Markov chain for searching and/or analyzing data in the knowledge base such as case summaries, treatment rationales, biomarkers, outcomes, or other relevant information.

Clinical Case Capture Tool

Disclosed herein is a clinical case capture tool for capturing the clinical case and/or case summary of a patient. The capture tool can generate the case summary using entered information for the captured case. The clinical case capture tool often comprises one or more software modules for carrying out various functions. In some instances, the capture tool comprises a software module presenting a plurality of selectable clinical case templates, each template comprising a plurality of adaptive clinical case parameters, each parameter comprising one or more selectable values. The capture tool may interface with a user-side application or provide a web interface for receiving user input. This allows a user to enter case information such as data on the patient, the disease or cancer, and any past or ongoing treatment(s). The user may enter input using a selectable clinical case template. Such templates can correspond to certain categories such as cancer type or other relevant characteristic. The adaptive clinical case parameters may dynamically change in response to previous parameter selections. For example, a user who is using a clinical case template for colorectal cancer may select a parameter indicating the presence of an APC mutation, which prompts an adaptive clinical case parameter to appear and/or present a selection of APC mutation types (e.g., point mutation, copy number variation, etc.). In this way, the plurality of templates enables a broad range of clinical case information to be captured from users such as at a point of care.

In some cases, the capture tool generates a case summary based on the clinical case information entered for a patient. The captured clinical case information can include treatment rationale(s), although treatment rationales are generally provided by molecular tumor boards rather than by the patient or physician at the point of care. In some cases, the physician provides a treatment rationale that is subsequently modified and/or validated by a molecular tumor board.

Clinical Survey Application

Disclosed herein is a clinical survey application for capturing treatment rationales such as in an MTB context. This clinical survey application can enable a user such as a trained "clinical analyst" to capture TRs directly into a knowledge base. The trained "clinical analyst" is typically a user who is trained to enter information into the clinical survey application in the form of a CNL such as BCE. The analyst often acts as a recorder for MTB (or other expert individual or group) reviews of captured clinical cases and facilitates the capture of treatment rationales by entering the case-contextualized reasoning in a CNL. Alternatively, an analyst may participate in the process after review by a MTB such as by converting a transcription or summary of the MTB's treatment rationale into BCE. FIG. 3 provides an illustrative example of a captured transcript from a MTB review of a clinical case including a treatment rationale. The use of a CNL enables rapid and efficient entry of the treatment rationale with minimal or no ambiguity. In some cases, the clinical survey application comprises one or more software modules for speech capture and/or readback tools. The clinical survey application may comprise a software module configured to transcribe captured or recorded audio for review and/or conversion by the clinical analyst into a CNL format. In certain instances, a software module is configured to apply a machine learning algorithm for carrying out natural language processing on recorded case entries (e.g., case information, case summary, treatment rationale, or other information associated with a clinical case) so as to generate an audio transcription. In some cases, the machine learning algorithm is trained to partially or completely format the entries into a CNL such as BCE. Sometimes, the clinical survey application also comprises one or more software modules for capturing the clinical case and/or clinical case summary (e.g., performing the functions of the clinical case capture tool). The clinical case capture tool can be a component of the clinical survey application.

In some cases, the survey of a molecular tumor board is conducted in a single step, or in an iterative process where the experts participate in a moderated discussion (synchronously in person or by teleconference, or asynchronously via email or the web); or a combination of these methods, whereby the discussion is informed by periodic surveys. The moderator can determine what happens at each step in the process, with the goal of guiding the discussion toward convergence on the best options for this patient. In each step, the experts may edit an existing treatment option or its rationale, provide additional rationales (pro and/or con) that support either the general desirability of that option (based on factors such as the quality of the science, the strength of clinical and preclinical evidence, or other relevant criteria) or its specific relevance to the case at hand (e.g., whether the patient meets the inclusion/exclusion criteria of a trial, or how well that option aligns with the patient's own treatment preferences). The experts can also use a survey tool (such as Survey Monkey or an application specifically designed for this purpose) to rank order the options. This ranking may be based on qualitative, subjective judgements, which they can document in the treatment rationales. They can also rank using objective measures of utility, such as might be provided by a computer running data analytics on the past performance of various treatments in similar patients, or the results of in vivo and in vitro assays, or an in silico simulation that predicts how well a patient is likely to do on a given treatment (e.g., a Bayesian classifier that predicts an outcome for the given treatment based on data for similar clinical cases from the knowledge base). The expert can also suggest new options that were not previously available or considered, along with their rationales for recommending that option. The survey/discussion process can iterate until it converges (e.g., no new options, rationales, or rankings). The results of this analysis by the molecular tumor board can be presented to the treating physician for the patient who will decide whether to treat the patient according to the recommendations by the tumor board or recommend the treatment to the patient. In some cases, the treating physician may select one of a ranked list of treatment options and rationales. The selected treatment and/or outcome data can be captured and used to update the knowledge base, which in turn can be used to improve the algorithms and models used by the decision engine to generate more accurate predictions for both existing and future cases in the virtual trials.

Figure 4:
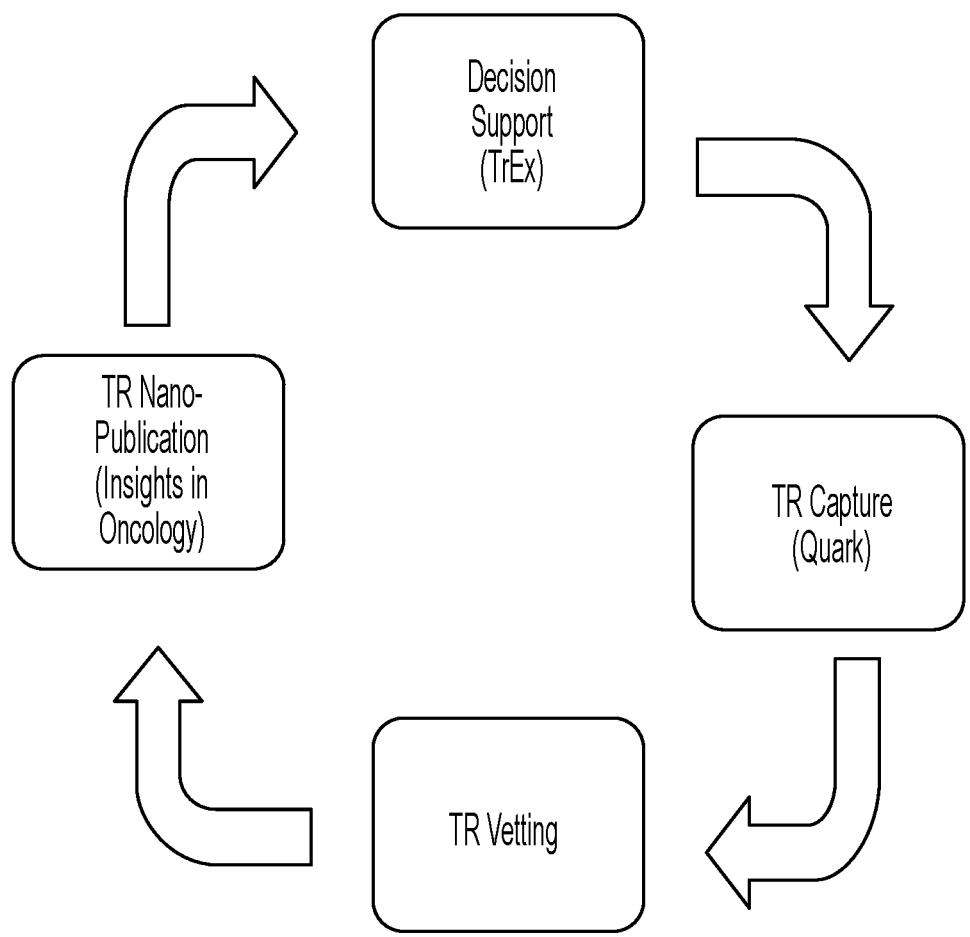
FIG. 4 shows an example process by which treatment rationales are captured, vetted, published, and incorporated into a decision engine for supporting treatment decisions.

Captured treatment rationales are often not publicly available on the network until they have undergone "peer review" (vetting of the treatment rationale by one or more other members of the network). FIG. 4 provides an overview of the process by which treatment rationales are captured, vetted, published, and then fed into an algorithmic decision engine for supporting patients and physicians in making medical decisions such as treatment (also see FIG. 15). Vetting is an optional quality control process that takes place during or after the capture process. Vetting is automated, partially automated, or manual. Different combinations of users and tools may undertake various aspects of vetting. For example, de-identification (anonymization) of clinical cases and/or treatment rationales can be automated, while checking for correct BCE may be carried out by trained domain experts (e.g., trained analysts), and scoring along content-relevant dimensions may be carried out by domain experts (e.g., doctors, scientists). Accordingly, captured treatment rationales may be shared to a limited network of domain experts for vetting before publication to the general public (e.g., becomes viewable or searchable by an end user such as a patient or attending physician). A vetting tool supports various checking and scoring such as checking de-identification and correct BCE encoding or scoring the TR along various dimensions. In some embodiments, the vetting tool captures three-point scores along dimensions of agreement, generality, importance, and level of evidence. This approach is predicated on the observation that professional oncologists rarely deal with specific quantitative information on the state of a patient's tumor, but rather communicate among themselves in semi-quantitative terms, for example by describing the patient's disease as "progressing", "rapidly progressing", "stable", "in remission", or other terms that lack precise quantitative meaning. Therefore, some versions of the vetting tool transact in "semi-quantitative" terms and three-point scales. Alternatively, the vetting tool may gather accurate numerical measures (e.g., alone or alongside the semi-quantitative dimensions) for greater precision. The vetting tool often provides users with the option to choose which measures are used in the vetting process. In some instances, the vetting process is anonymous (e.g., such as with traditional peer review). Alternatively, the vetting process may analogous to open peer review with the identities of any users performing the vetting being disclosed. FIG. 5 shows an illustrative embodiment of a peer review interface for scoring a treatment rationale statement according to the dimensions of agreement, generality, evidence, and importance.

Vetted TRs, represented in correct BCE, can be automatically compiled into partial internal semantic code. Non-limiting examples of this semantic code include the data component entries from the knowledge base shown in Table 1. This format enables computer-based manipulation and analysis such as organizing clinical cases into cohorts for virtual trials and predicting treatment outcomes.

The treatment rationale and/or associated case summary are generally published to the knowledge base once the vetting process has been completed. FIGS. 6A-6B provide an illustrative representation of rows of nano-publication entries in a nano-journal. In some instances, the case is published as a nano-publication such as in a nano-journal within the knowledge base. The published case can include any of the case summary and/or treatment rationale in BCE, the vetting scores, and the data components or internal representations of the case. The vetting process often requires a minimum number of vetting or peer review or, alternatively, a minimum number of agreements before publication. As an example, the vetting process may require at least three peer reviews to be in agreement regarding the three-point scores along the dimensions of agreement, generality, importance, and level of evidence for a given case before it is published to the knowledge base. This provides a level of quality control to prevent or mitigate publication of cases or treatment rationales that contain ambiguities. In some cases, the vetting process requires at least one, two, three, four, five, six, seven, eight, nine, or ten peer reviews to be in agreement for at least one parameter or dimension for a treatment rationale for it to pass the vetting process and/or proceed to publication. The information published to the knowledge base can be used for downstream analysis such as according to any of the machine learning algorithms described herein for organizing and coordinating clinical cases into cohorts or case series for carrying out virtual trials.

Treatment Explorer

Disclosed herein is an application for ranking possible treatment options treatments based on patient and/or treatment information such as test results (e.g., biomarker or molecular profile, tumor characteristics, etc.). An example of a treatment explorer interface is shown in FIGS. 7A-7B. The treatment options can be treatment rationales (e.g., provides contextual reasoning for the specific treatment). Ranked treatment options can be generated for an entered clinical case such as one captured using the clinical case capture tool. Alternatively, ranked treatment options may be generated in response to entry or selection of specific parameters (e.g., positive test result for a biomarker, a specific cancer type or subtype, resistance to a certain therapeutic agent). Examples of test parameters and results are shown in FIGS. 7A-7B indicating test results for specified biomarkers. In some instances, filters are applied to further sort and/or narrow the ranked search. The ranked treatment options may be limited to only include those options supported by certain kinds of evidence such as clinical modes (e.g., case series, controlled trials, or meta-analyses of controlled trials). The columns in the ranked results may include "sources" and "notes" columns. The sources column entries are often clickable and can typically bring the user to the PubMed entry for the paper from which the evidence was obtained. This enables one to examine the source of the evidence if one likes. Furthermore, a user may drill down into the knowledge base by selecting a condition (e.g., biomarker mutation), a treatment hypothesis or treatment rationale, the source of the information, or the original BCE write-up of the treatment rationale. In cases when the evidence is a case context, one or more links may be displayed that lead to the case summary.

In some cases, the ranked treatment options are ranked according to one or more ranking algorithms (Mocellin et al. (2010) Targeted Therapy Database (TTD): A Model to Match Patient's Molecular Profile with Current Knowledge on Cancer Biology. PLoS ONE 5(8): e11965). The information provided by the treatment explorer may be accessible by experts such as MTBs during the treatment rationale capture process. In some cases, the treatment explorer is a part of the clinical decision engine (e.g., one or more software modules).

Virtual Trials

Disclosed herein are platforms, systems, media, and methods for carrying out virtual trials. In some cases, virtual trials are carried out using analysis of information from the knowledge base or network. The analysis typically entails use of an algorithm such as a Bayesian machine learning algorithm that seeks simultaneously to optimize the assignment of patients to cohorts and the best treatment options for each cohort by gathering evidence to validate or reject treatment hypotheses within and/or across cohorts. These algorithms may be used to generate output presented to a user such as via the treatment explorer interface described herein. As an example, advanced cancer patients arrive randomly at tumor boards (TBs) in the knowledge network of patients, doctors, expert clinicians, researchers, or other participants.

New patient cases can be uploaded into a knowledge base configured to store a plurality of clinical cases. The knowledge base can store clinical information pertaining to the cases such as patient genetic information (e.g., detected mutations from a tumor biopsy), serum biomarkers (e.g., protein metabolites in the blood), cancer stage, time of diagnosis, molecular subtype of the cancer (e.g., ErbB2 positive breast cancer). The knowledge base can also store one or more treatment options and/or treatment rationales for each clinical case. Treatment options can include known or available treatments for the patient's disease, while the treatment rationale provides the basis for the treatment's potential therapeutic effectiveness. In some instances, at least some of the treatment options and/or treatment rationales are determined before the tumor boards evaluate the case. For example, treatment options and/or treatment rationales may be gathered or mined from the scientific literature, conferences, research data, medical records, or other available sources of healthcare information. In some cases, the tumor board itself provides treatment options and/or treatment rationales during their assessment of the clinical case. Treatment options and/or treatment rationales can be generated based on analysis of existing clinical cases within the knowledge base determined to be similar to the specific clinical case. For example, in the case of a stage II ErbB2 positive breast cancer patient, the knowledge base may be searched to identify a cohort of cases having the same cancer type, cancer stage, and molecular profile (or any other relevant factors such as patient sex, age, etc.). A decision engine employing an algorithm such as a Bayesian classifier may then evaluate the cohort to identify one or more treatment options (which can have associated treatment rationales). The treatment options can be ranked or prioritized according to a statistical score. The classifier can continuously update based on new data (e.g., administered treatment(s) and outcome or result of the treatment(s)) and re-evaluate the ongoing clinical case. Thus, the decision engine may dynamically or continuously monitor a clinical case over time and recommend a change to the existing treatment options or a new treatment based upon the updated classifier when the ranking or prioritization of the treatment options changes. For example, it may be discovered that the first cohort undergoing a specific treatment is experiencing outcomes that are statistically worse than a second cohort having the same clinical profile but using a different treatment. In this case, the classifier may generate updated rankings of the treatment options to indicate a higher ranking for the first cohort and a lower one for the second cohort due to the outcome data. A tumor board may take this information into account and make the recommendation to switch the second cohort to the treatment for the first cohort.

The treating physician for an individual case in the second cohort may then make a decision on whether to adopt the recommendation. In some instances, the knowledge base is continuously being updated with information for new clinical cases and new information for existing cases already uploaded to the database. This information can be used to update or re-train the classifier(s) utilized by the decision engine to generate updated rankings or prioritizations of treatment options and/or associated treatment rationales.

The virtual trials can be informed by a decision engine helping to coordinate the treatment plans across similar patients to maximize learning and information gain. When there is a clearly best option, ethics require the patient receives that superior option. However, in the case of equipoise when more than one treatment option is available without a best choice (e.g., when the experts do not have a strong preference among the top options), the decision engine may utilize an algorithm to prioritize options that can accelerate learning. For example, the algorithm may prioritize treatments that are working (e.g., incoming outcome data indicates some success in initial virtual trials) to quickly replicate successes and amass a case series (e.g., a cohort of similar cases utilizing the same treatment option/rationale); alternatively or in combination, running pop up studies to resolve equipoise sets (a set of options that are judged to be roughly equal in terms of quality and relevance to the patient), or directing patients to treatments in the equipoise set for which there is less data, and thus more uncertainty, or in the simplest case, prioritizing options randomly so that everyone doesn't try the same treatment (which would result in little or no new information or learning).

Figure 8:
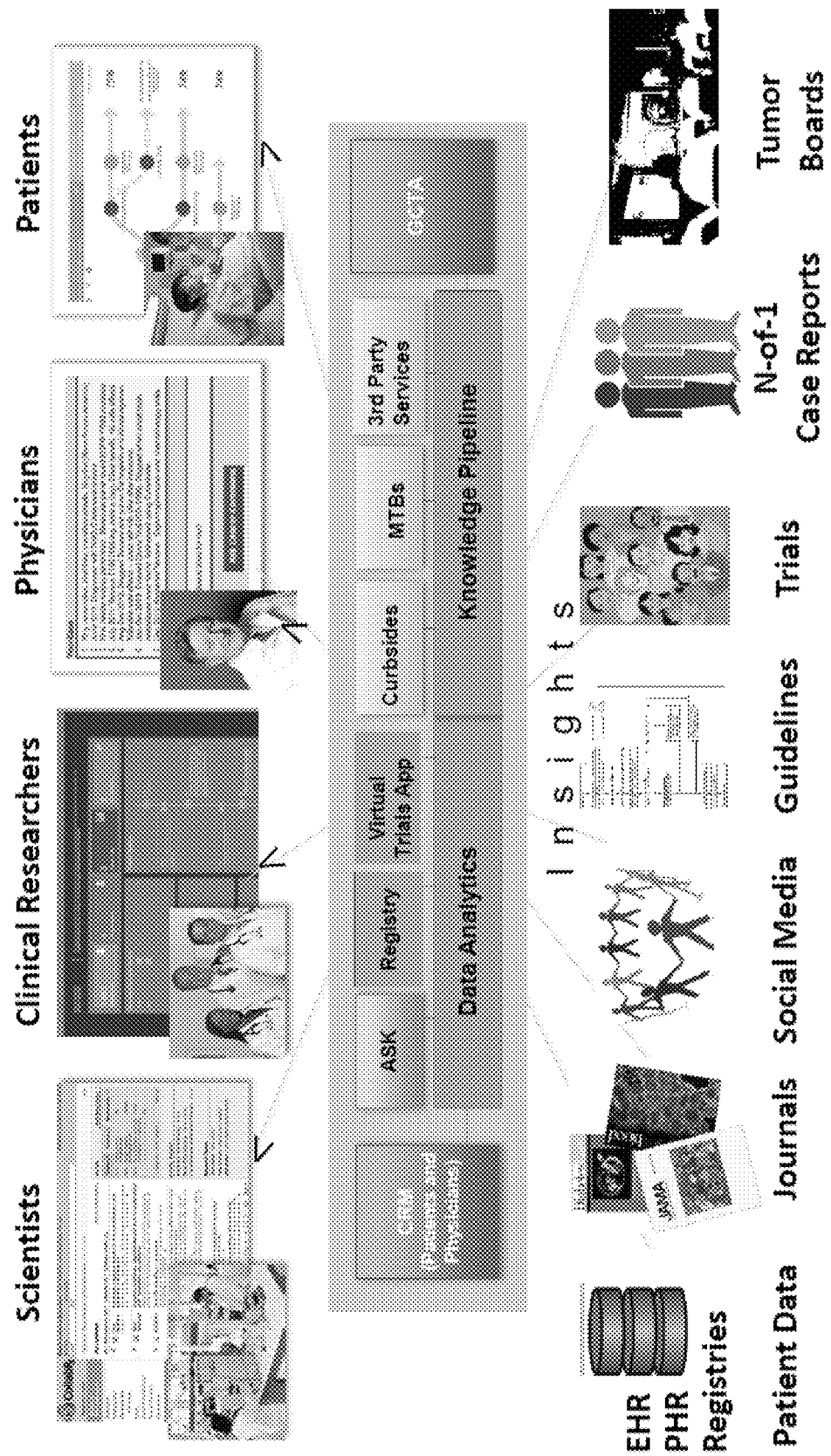
FIG. 8 shows an illustrative example of a technology platform described herein.
Figure 9:
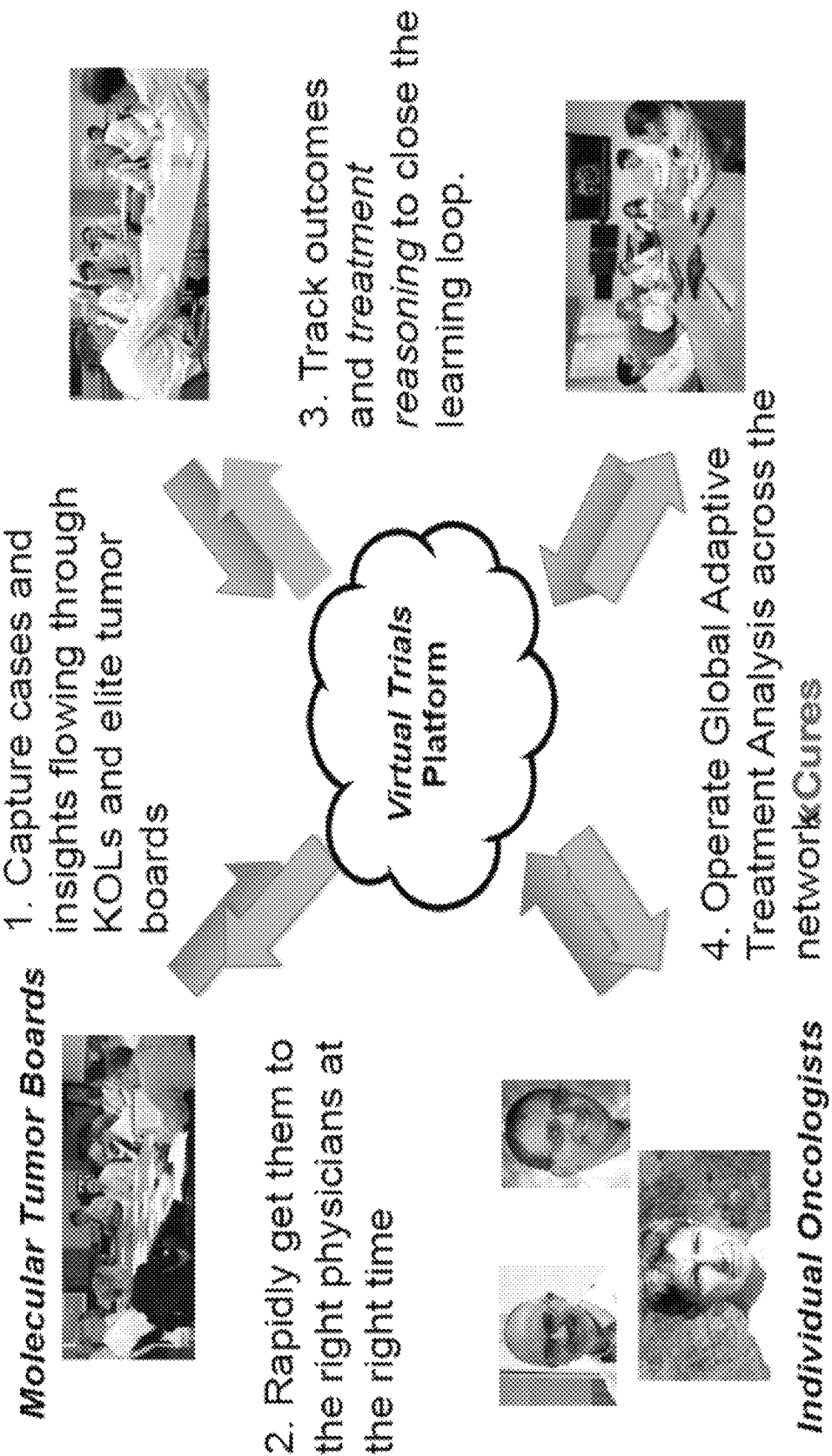
FIG. 9 shows an illustrative example of high level steps carried out through a platform for conducting virtual trials.

The present disclosure provides an ecosystem that connects a community to leverage clinical insights for better patient outcomes. As shown in FIG. 8, the community can include scientists, clinical researchers, physicians, and patients. Various sources of information and insight can be gleaned from this collaborative community such as via patient data, journals, social media, medical guidelines, trials, N-of-1 case reports, and tumor boards. The data analytics and knowledge pipeline can be combined to generate treatment hypotheses and rationales as well as coordinate virtual trials for validation. FIG. 9 provides an illustrative example of the high level steps for conducting virtual trials. The platforms described herein can allow for cases to be captured and evaluated such as by molecular tumor boards. Recommended treatment options and treatment rationales can help guide patients to the appropriate physicians (e.g., independent oncologists who may specialize or have expert knowledge on the particular treatment). The treatment outcomes and treatment rationales are tracked and the outcome data fed back into the platform to close the learning loop. In other words, the platform, which may comprise one or more decision engines (e.g., Bayesian machine learning decision engine), can utilize the outcome data to learn and improve its ability to coordinate ongoing and future virtual trials. Thus, the decision engine can consider all patients all the time in a continuous basis. For example, virtual trials may be conducted such that patients cannot be excluded (no exclusion criteria), no controls are used, and no placebos—and as treatments fail or new superior treatments or combinations of existing drugs are determined to be superior, patients may be dynamically switched over to the better treatments as part of an ongoing virtual trial.

Figure 11:
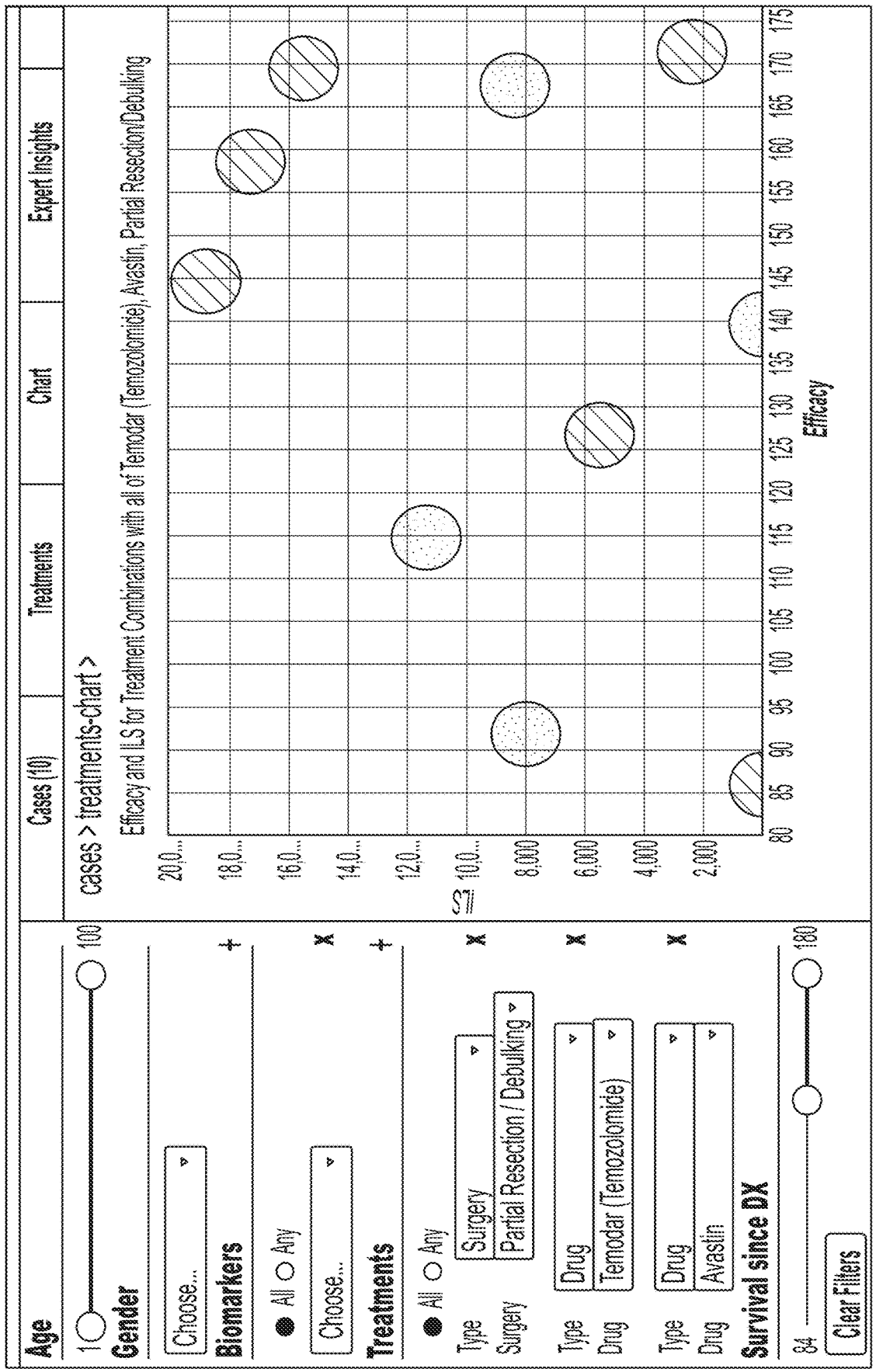
FIG. 11 shows an embodiment of a virtual trials interface presenting a treatment chart allowing comparison of treatments amongst clinical cases in the knowledge base.
Figure 12:
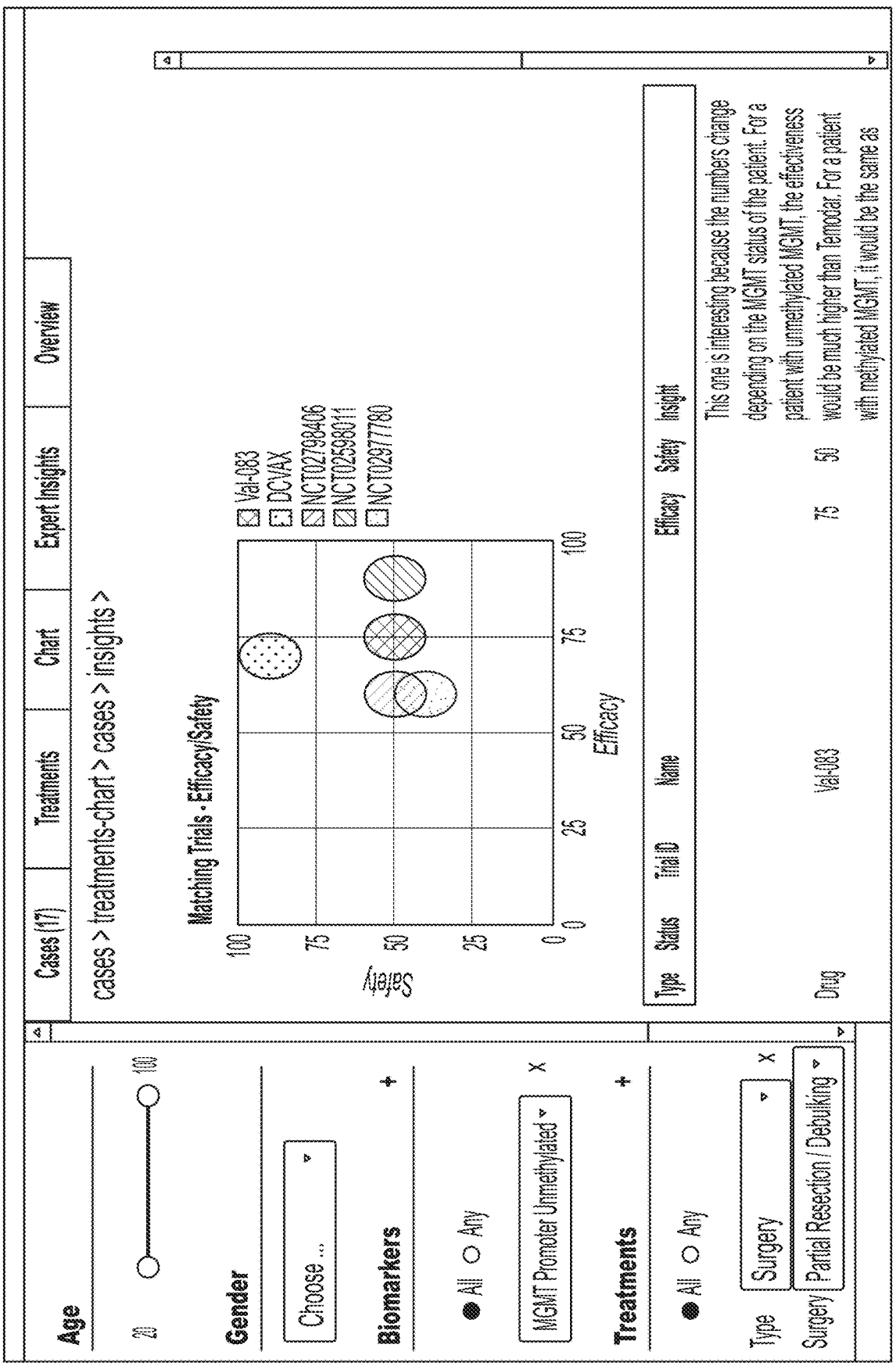
FIG. 12 shows an embodiment of a virtual trials interface presenting expert insights on matching trials.
Figure 13:
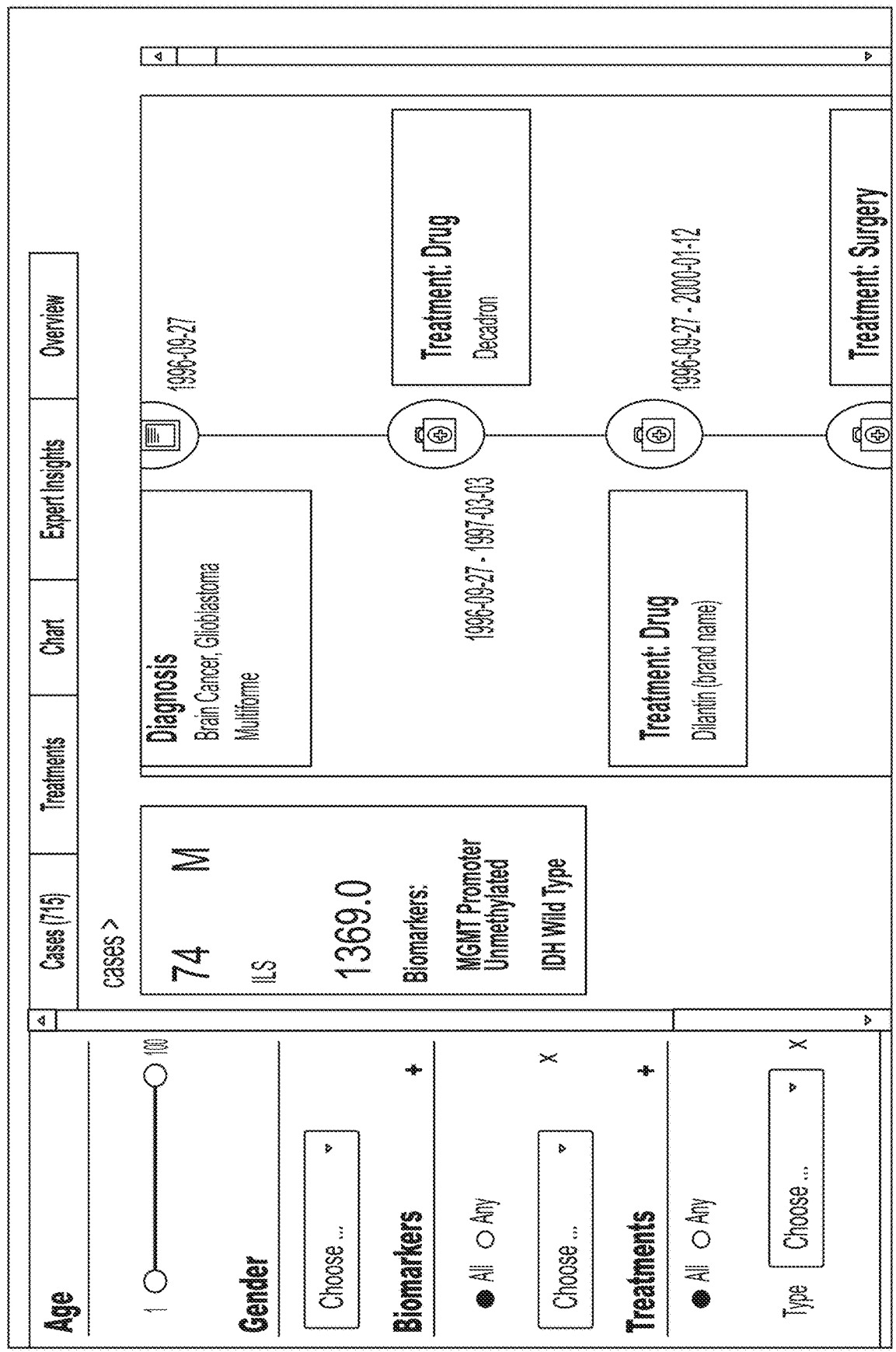
FIG. 13 shows an embodiment of a virtual trials interface presenting the treatment history for a particular clinical case.
Figure 14A:
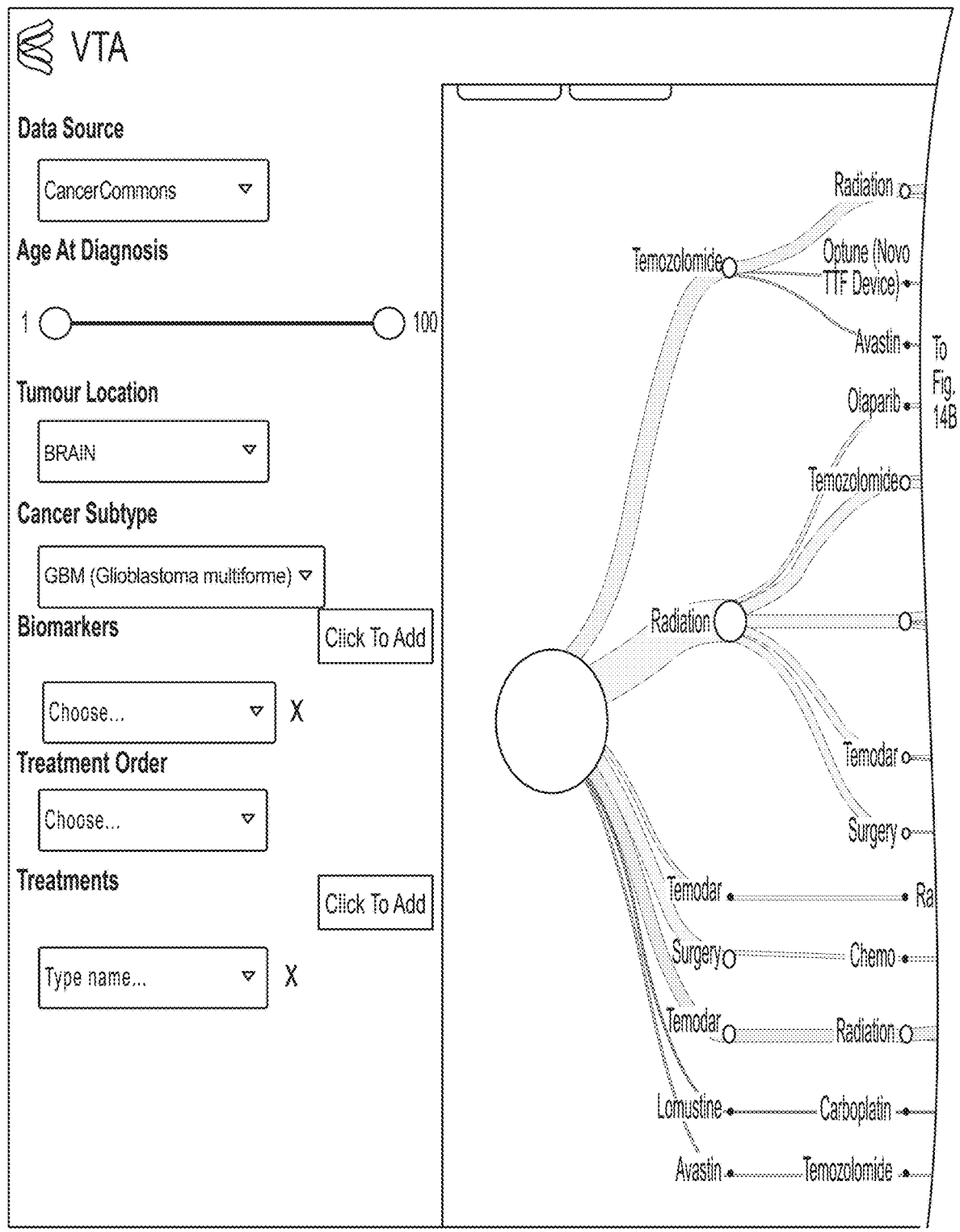
FIGS. 14A-14B show an embodiment of a cancer map displaying the treatment history and outcomes of a cohort of clinical cases for patients diagnosed with glioblastoma.
Figure 14B:
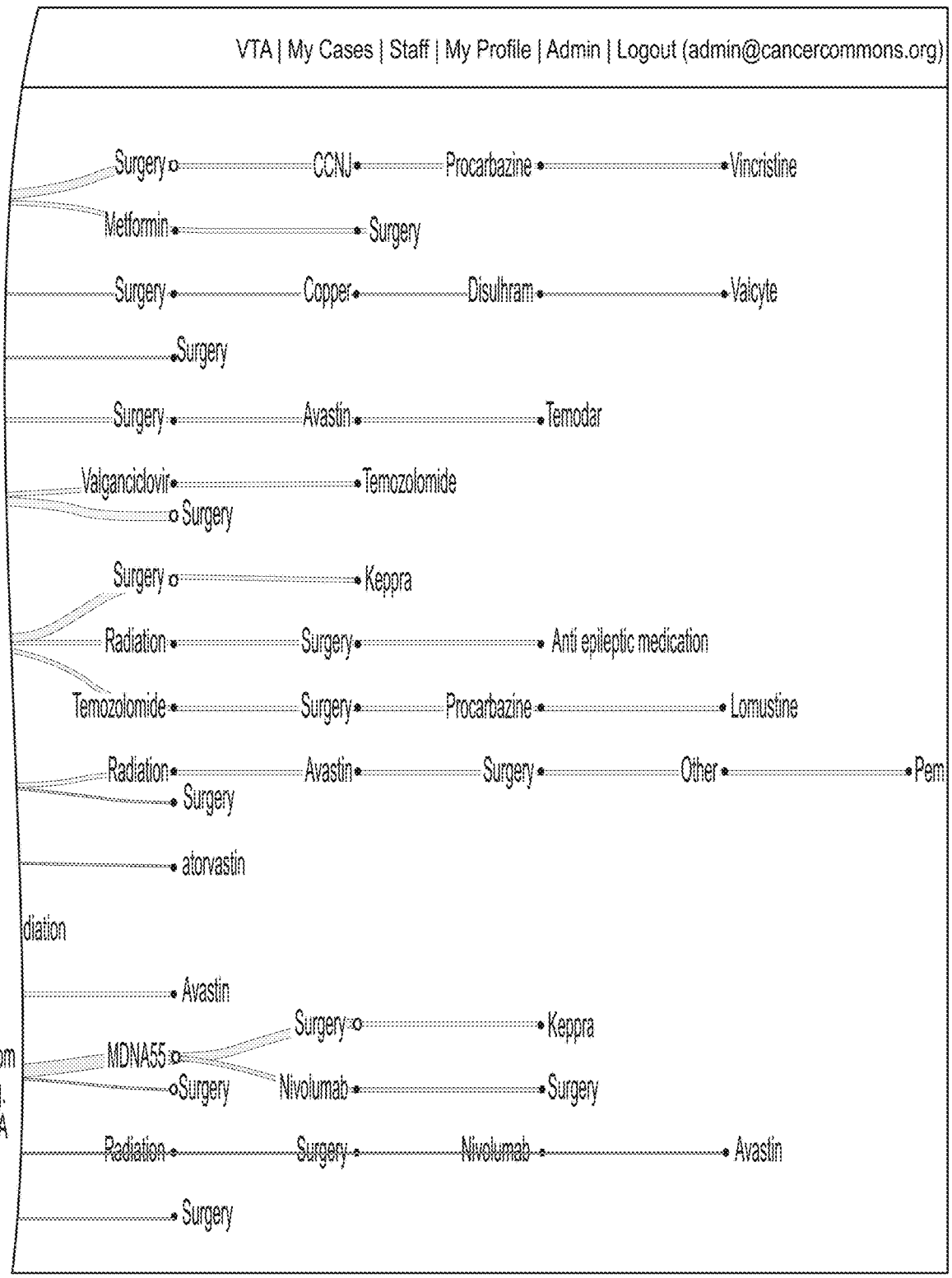
Figure 15:
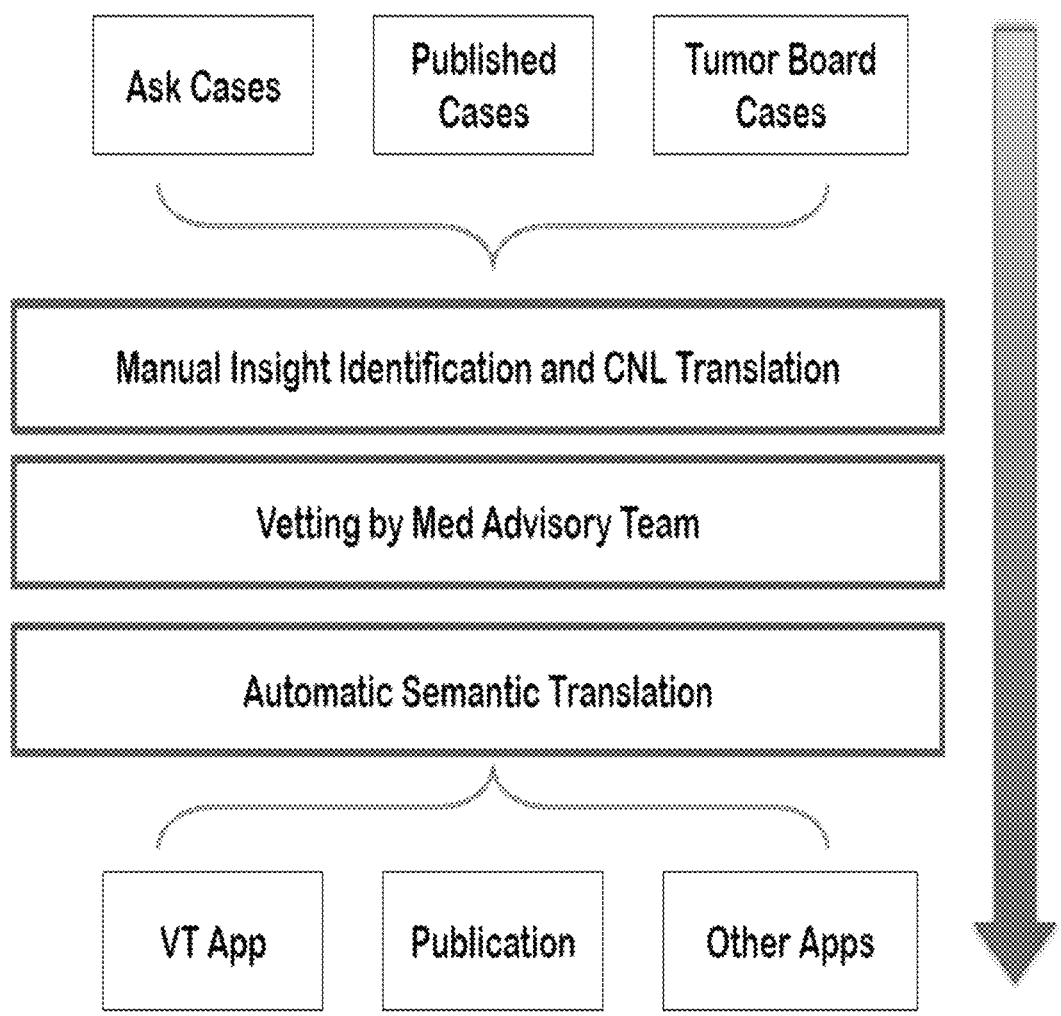
FIG. 15 shows a flow diagram illustrating a knowledge pipeline by which expert insight is captured, analyzed, and distributed according to the platforms and methods described herein.
Figure 16:
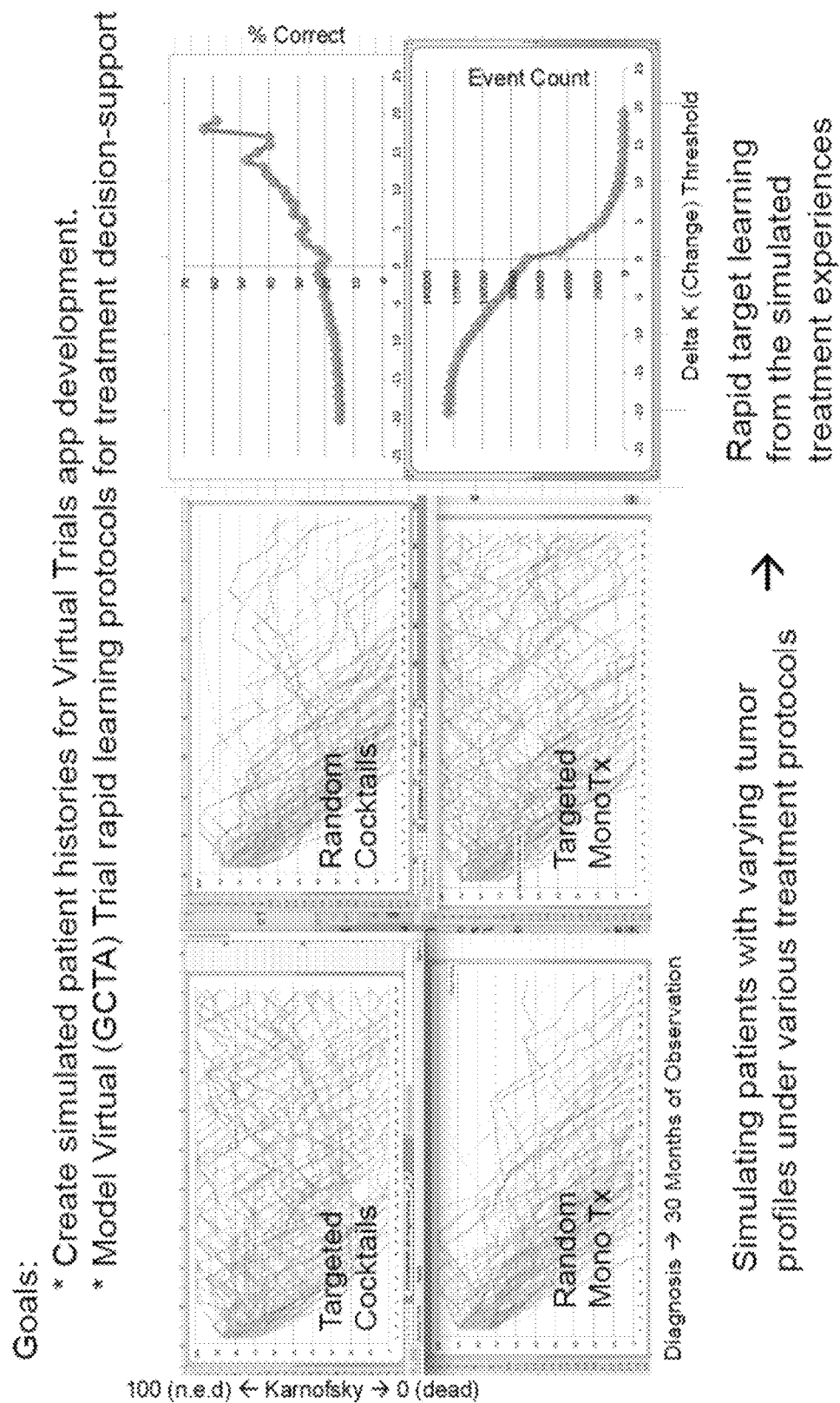
FIG. 16 shows a virtual trial simulator that generates simulated patient histories for development and/or training of a virtual trials application.

A user may use an application or portal presenting an interactive virtual trial interface. The interface can comprise parameters comprising user-selectable values. These parameters can include patient information such as age, gender, biomarkers, treatments, survival since diagnosis, and other relevant criteria that may be used to sort, filter, and/or search for a cohort of clinical cases. The interface can provide detailed information such as cases identified in a search, treatments, chart, expert insights (e.g., treatment rationales or other insights), an overview, or any combination thereof. Examples of the interface are shown in FIGS. 10A-14B. FIGS. 10A-10B show a list of cases identified using a parameter-based search. FIG. 11 shows an efficacy vs ILS chart for treatment combinations. FIG. 12 shows treatment insights relating to matching trials. FIG. 13 shows the treatment history for a particular clinical case. In addition, FIGS. 14A-14B show a cancer map displaying the treatment history and outcomes of a cohort of clinical cases for patients diagnosed with glioblastoma. This cancer map can be obtained by searching or selecting a cohort of cases. The interface may be for a virtual trials app (VT app), which interfaces with the rest of the platform and is able to receive or visualize information that has been translated such as by an automatic semantic translation (FIG. 15). In some cases, simulated patient histories are generated under various treatment protocols to achieve rapid target learning (FIG. 16).

The platforms and methods disclosed herein can carry out virtual trials according to formats distinct from traditional clinical trials. In some cases, a virtual trial has no exclusion criteria. For example, a virtual trial may have no placebo. In some instances, virtual trials have no control groups (e.g., no control arms or cohorts). A key benefit in this scenario is that a patient will not be turned away. When there is no exclusion criteria, patients can also never be dropped from the virtual trial (such as after the trial has commenced). In case a patient does fail a particular treatment (e.g., negative or ineffective outcome) during a no-exclusion virtual trial, the patient must be reassigned to another cohort or n-of-1 arm. These features of the present disclosure further distinguish virtual trials from the methodology carried out in traditional clinical trials, in which subjects who drop out of the clinical trial are unable to rejoin.

An algorithm can generate one or more treatment options for the patient from which a tumor board may select a particular treatment or treatment combination (e.g., multiagent treatment). Alternatively, the tumor board creates the treatment or treatment combination based on their expertise and/or the available information in the network. For example, the tumor board may have knowledge that a particular treatment option is ineffective based on the molecular profile of a biopsy obtained from the patient and adjust the treatment recommendation accordingly. Thus, the tumor board can validate and/or modify the treatment rationale. When there is equipoise or some other gap in knowledge, the algorithm chooses the treatments from a list of plausible treatment options, which is optionally based on which treatment option can provide the most information. For example, when two treatment options are equivalent in terms of predicted efficacy, the algorithm may choose the option that is associated with a smaller cohort of patients so as to increase the statistical robustness of the data. The patients are then dynamically grouped into cohorts based on any statistically relevant features of the patient or treatment option. In some cases, a cohort contains only one patient (N-of-1 cohort).

Another key advantage of the virtual trial that further differentiates from traditional clinical trials is the ability to test various drug or treatment combinations. Traditional clinical trials are normally limited to testing of specific agents in large, randomized, controlled trials due to both regulatory and financial constraints (e.g., lack of incentive to test proprietary drug in combination with a competitor's product). The virtual trials disclosed herein can offer an alternative solution that leverages both the insights of domain experts and computer analytics to drill down to potentially effective treatment combinations that are not considered in clinical trial formats. For example, the methods disclosed herein allow for the capture of treatment combinations, analysis of the outcomes, predictions for new clinical cases, and the coordination of clinical cases to carry out virtual trials involving multiple cohorts and/or n-of-1 cases. This process can enable numerous drug and treatment combinations to be evaluated continuously and cumulatively in an ongoing learning process driven by expert insight and facilitated by computer algorithms. This process can also allow the injection of treatment hypotheses for coordinating virtual trials of ongoing clinical cases. For example, a decision engine or molecular tumor board may discern that a particular multi-drug combination may have a synergistic effect in treating tumors having a specific biomarker profile. Perhaps there is not enough data to be certain. However, this information may be sufficient to test the treatment hypothesis by coordinating one or more cohorts or n-of-1 cases to receive the treatment combination (which may be compared to other cohorts/cases receiving more traditional treatment) and monitoring them for one or more outcomes. As outcome data is accrued to the knowledge base, the decision engine may begin switching or recommending the switching of cohorts onto the more effective treatment. Accordingly, the methods described herein can provide a dynamic virtual trial platform that accrues data, improves its predictive and/or coordination abilities based on new data, and conducts virtual trials accordingly in a positive feedback loop.

A virtual trial may be monitored for additional information that becomes available throughout its duration. Biomarkers may be tracked as laboratory testing or diagnostics are performed. These biomarkers may be added to the virtual trial, tracked, and analyzed using any of the algorithms described herein. The insight provided by the biomarkers may be incorporated into a virtual trial by modifying the trial to test new treatments or treatment combinations. In some cases, the information is taken into account when the decision engine coordinates new cohorts or n-of-1 virtual trials that are designed to test the impact of the biomarker on treatment options. In contrast, traditional clinical trials do not allow new treatments, even if approved, to be used by patients in the ongoing trial. Consequently, the present disclosure enables a patient-centric approach with the goal of improving patient outcomes rather than the traditional clinical trial focus on the drug itself.

Another advantage provided by the methods disclosed herein is the ability to account for non-medical information to produce or predict the best outcome for a patient. For many patients, the cost of healthcare is an important consideration when deciding on treatment options. Accordingly, factors such as insurance coverage, reimbursement (yes/no/likelihood), out of pocket costs, and other financial considerations may be integrated into the treatment rationales and/or the knowledge base to add further dimensions to the decision engine analysis (e.g., accounting for finance when coordinating virtual trials or predicting outcomes). For example, in cases when two treatment options are predicted to be similar or equivalent in an outcome such as 5-year survival, the decision engine may assign a clinical case to the treatment with a lower out of pocket cost.

In some embodiments, a decision engine uses self-learning schemes to analyze cases in the knowledge base, for example, machine learning algorithms, artificial intelligence algorithms, artificial neural networks, logistic regression models, inductive logic programming, statistical clustering algorithms, Bayesian learning schemes, probability based classification algorithms, support vector machines, and/or other forms of self-learning schemes that are able to understand the information about the patient and/or the patient's treatment regimen, and derive a conclusion about the possible treatment options for the user based on this data.

Figure 17:
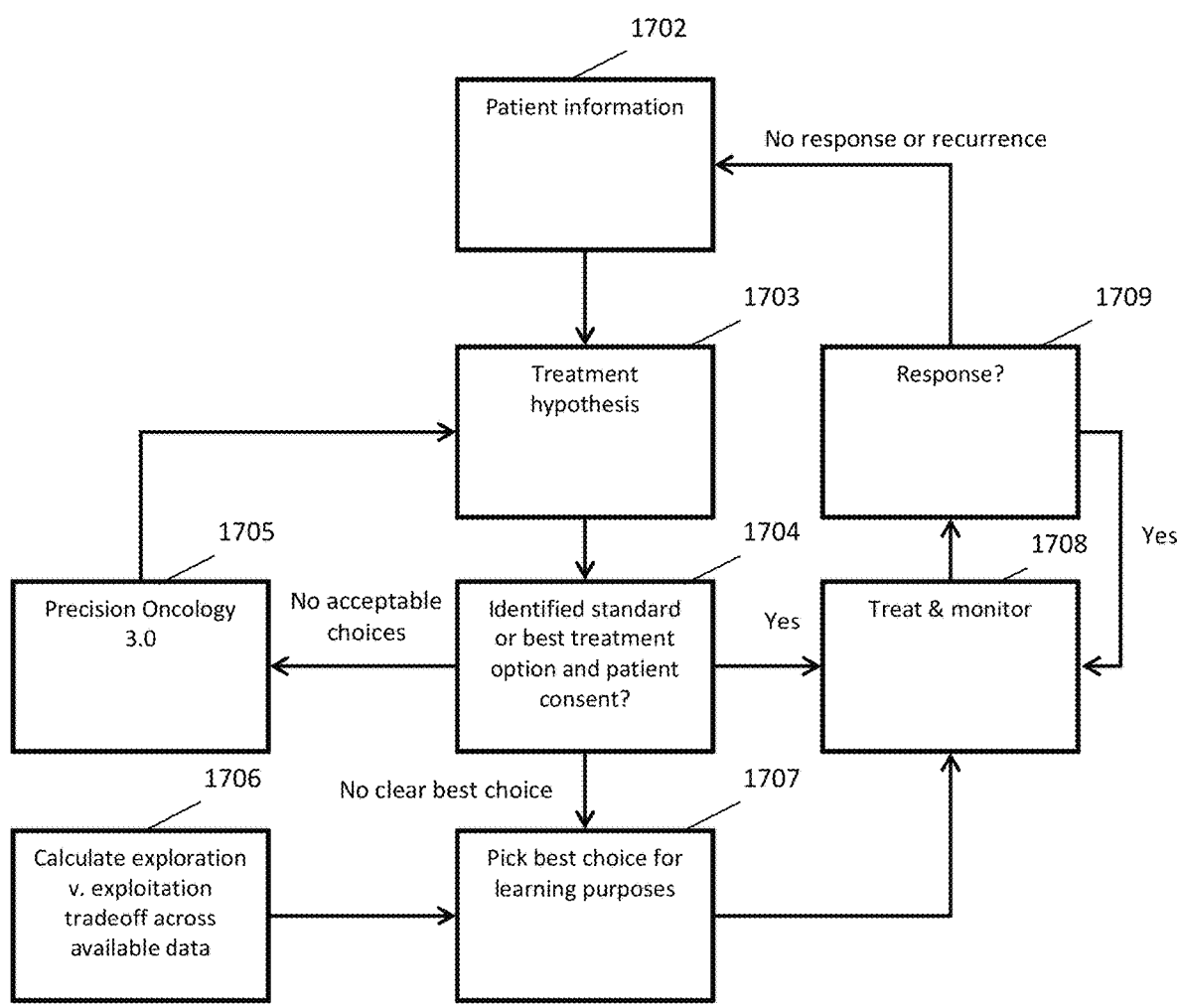
FIG. 17 shows illustrative flow chart of a method for carrying out patient treatments.

FIG. 17 provides an illustrative flow chart showing one process by which a patient may be treated and monitored. Patient information 1702 may be obtained (e.g., through the clinical case capture tool) and can include panomic data (e.g., such as genomic, proteomic, metabolomics, and/or transcriptomic data). One or more treatment hypotheses 1703 can be generated by molecular tumor boards that review the case and/or according to predictive algorithm(s) that evaluate the case based on analysis of insight from the knowledge base (e.g., past cases and treatment rationales validated with outcome data). When a treatment is identified as the best or optimal treatment 1704, then a consenting patient may receive treatment and monitoring 1708. A response 1709 that is positive may result in the treatment being continued. Conversely, a lack of response provides outcome data that may be used to generate one or more new treatment hypothesis 1703. In the case that there is no clear best choice, a tradeoff analysis 1706 of the treatment options may be calculated using an algorithm to select the best choice for learning purposes 1707. The tradeoff analysis can utilize a model that attempts to acquire knowledge (exploration) and attempts to optimize decisions based on existing knowledge (exploitation) so as to maximize the value (information). This problem is often referred to as the multi-armed bandit problem in probability theory. When there are no acceptable choices, then additional information may be needed to generate more treatment hypotheses. Precision Oncology 3.0 tools 1705 may provide the data needed and can include analyzing biopsies, panomics testing, network analysis, identifying targets (e.g., molecular drug targets based on biomarker profile), testing, combo therapies, or examining serum markers. This information may be fed back into the generation of new treatment hypotheses 1703.

The network of patients that participate in the platform described herein can be always on and pre-consented such that patients may be added to virtual trial testing without having to actively obtain consent. The virtual trials can be seamlessly progressed from one phase to the next. For example, a virtual trial may progress from phase 1 to phase 2, 3, or 4. This progression can occur dynamically as the decision engine monitors and coordinates virtual trial cohorts. For example, a virtual trial testing a particular combination treatment using existing drugs on the market may begin based on treatment hypotheses generated by molecular tumor boards for a particular cohort of patients. The testing may begin in phase 1 by evaluating pharmacokinetics, and seamlessly transition to phase 2 once sufficient outcome data is collected for the treatment to pass phase 1. During phase 2, efficacy of the treatment is evaluated. Moreover, information gathered during phase 1 may also be incorporated into the outcome data for phase (e.g., signs of efficacy or lack thereof during phase 1 is taken into account during phase 2). The methods described herein can enable ultra-efficient virtual trials to be conducted by third parties such as pharmaceutical companies. For example, the CRO for a virtual trial patient may be about $10-20 k in contrast to about $50 k for current CROs.

Monetization

The knowledge base may be monetized by charging fees and/or subscriptions to medical professionals and/or institutions. In addition, other parties such as pharmaceutical companies, insurance companies, Wall Street firms or companies, and other parties may pay for access. Pharmaceutical companies seeking a cheaper and more effective alternative to the clinical trial can pay for access to the platforms described herein for the designing and carrying out of virtual trials. Profit sharing with knowledge providers (e.g., molecular tumor boards, clinicians, trained analysts, patients/doctors, journals, cancer centers and other institutions, etc.) can be used to incentivize the sharing of information via the knowledge base.

Digital Processing Device

In some embodiments, the platforms, media, methods, and applications described herein include a digital processing device, a processor, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device. In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Many smartphones are suitable for use in the system described herein. Select televisions, video players, and digital music players with optional computer network connectivity are suitable for use in the system described herein. Suitable tablet computers include those with booklet, slate, and convertible configurations.

In some embodiments, the digital processing device includes an operating system configured to perform executable instructions. The operating system is, for example, software, including programs and data, which manages the device's hardware and provides services for execution of applications. Suitable server operating systems include, by way of non-limiting examples, FreeB SD, OpenBSD, NetBSD®, Linux, Apple® Mac OS X Server®, Oracle® Solaris®, Windows Server®, and Novell® NetWare®. Suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the non-volatile memory comprises magnetoresistive random-access memory (MRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a subject. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In some embodiments, the display is E-paper or E ink. In other embodiments, the display is a video projector. In still further embodiments, the display is a combination of devices such as those disclosed herein.

In some embodiments, the digital processing device includes an input device to receive information from a subject. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, the platforms, media, methods, and applications described herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, media, methods, and applications described herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. A computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. A web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. A web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

A mobile application can be created using hardware, languages, and development environments. Mobile applications may be written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, media, methods, and applications described herein include software, server, and/or database modules, or use of the same. Software modules may be created using machines, software, and languages. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. Many databases are suitable for storage and retrieval of barcode, route, parcel, subject, or network information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Technology Platform

Figure 18:
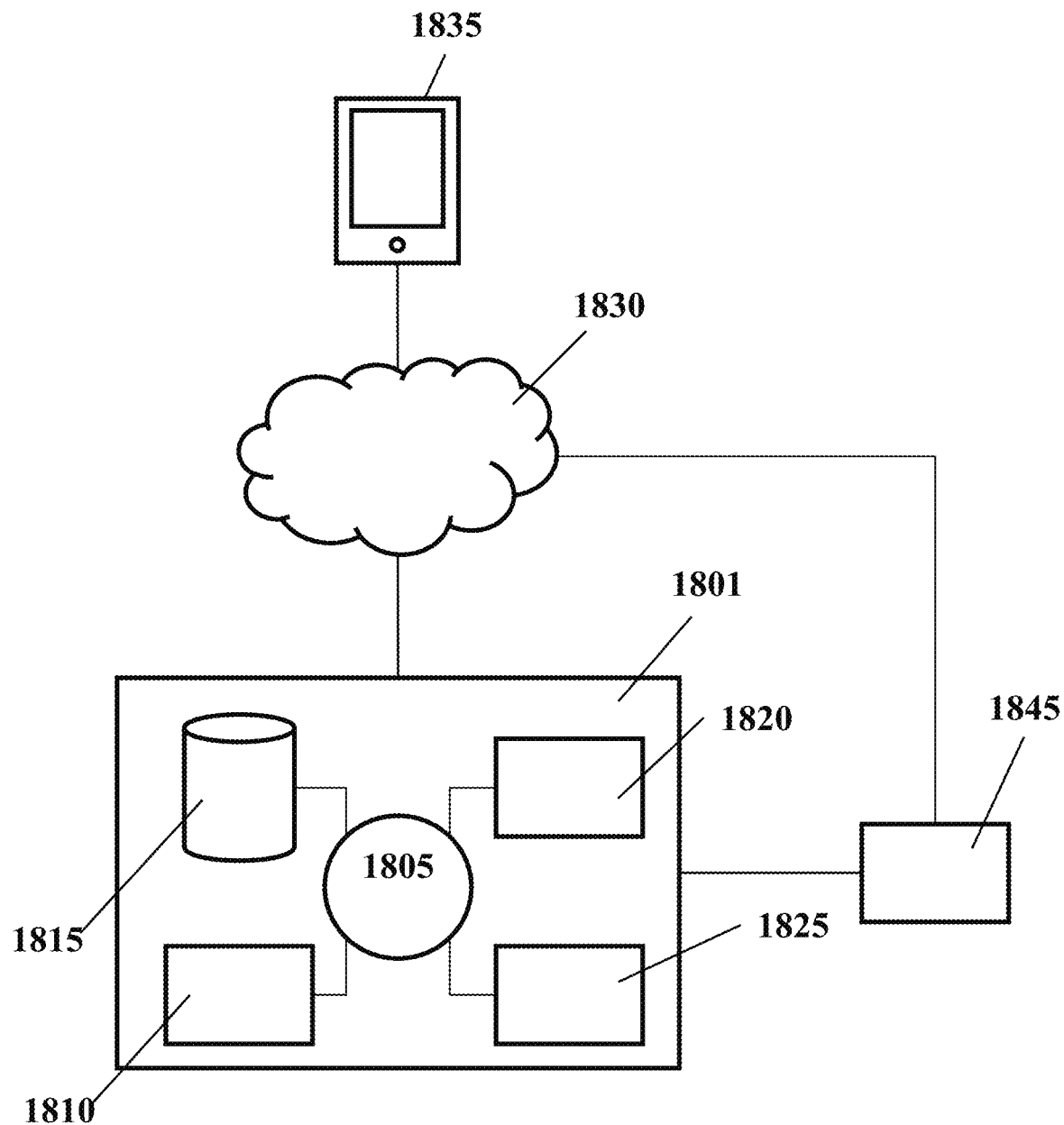
FIG. 18 schematically illustrates a computer control system that is programmed or otherwise configured to implement methods provided herein.

FIG. 18 schematically illustrates a computer control system or platform that is programmed or otherwise configured to implement methods provided herein. The system can comprise a computer system 1801 that is programmed or otherwise configured to carry out executable instructions such as for implementing a decision engine. The computer system includes at least one CPU or processor 1805. The computer system includes at least one memory or memory location 1810 and/or at least one electronic storage unit 1815. The computer system can comprise a communication interface 1820 (e.g., network adaptor). The computer system 1801 can be operatively coupled to a computer network ("network") 1830 with the aid of the communication interface 1820. An end user device 1835 may be used for entering clinical case information (e.g., by a physician at the point of care), uploading treatment rationales (e.g., by a trained analyst following MTB review), vetting (e.g., of treatment rationales by clinicians or other domain experts), general browsing of the knowledge base 1845 (e.g., nano-publications available to the public), or performance of other suitable tasks. The knowledge base 1845 may be one or more databases separate from the computer system 1801.

NUMBERED EMBODIMENTS

The following embodiments recite nonlimiting permutations of combinations of features disclosed herein. Other permutations of combinations of features are also contemplated. 1. A computing platform comprising: (a) a processor configured to provide a clinical case capture tool comprising: (i) a software module for presenting a plurality of selectable clinical case templates, each template comprising a plurality of adaptive clinical case parameters, each parameter comprising one or more selectable values; (ii) a software module for receiving user input pertaining to at least one template, parameter, and value to capture a clinical case of a patient; and (iii) a software module for generating a summary of a captured clinical case, the summary comprising at least one treatment rationale for the patient; (b) a processor configured to provide a clinician survey application comprising: (i) a software module for publishing the summary of the captured clinical case to an expert clinician network; (ii) a software module for collecting vetting feedback pertaining to a treatment rationale of the summary; and (iii) a software module for storing a plurality of vetted treatment rationales to form a knowledge base; and (c) a processor configured to provide a clinical decision engine comprising: (i) a software module allowing a user to identify a cohort and a treatment hypothesis; (ii) a software module applying an algorithm utilizing the knowledge base to provide one or more ranked treatment protocols; and (iii) a software module providing a registry for collecting outcome data to train the algorithm. 2. The platform of embodiment 1, wherein the clinical case capture tool comprises a software module for converting user input from a Controlled Natural Language (CNL) into a formal logic. 3. The platform of embodiment 1, wherein the clinical case capture tool generates a standardized summary of each clinical case captured. 4. The platform of embodiment 1, wherein the clinical case capture tool comprises a treatment explorer generating ranked treatment options based on clinical case information. 5. The platform of embodiment 1, wherein the clinical case capture tool comprises templates, parameters, and values derived from a clinical modeling language. 6. The platform of embodiment 1, wherein the clinical case capture tool comprises parameters and values selected from Controlled Natural Language (CNL). 7. The platform of embodiment 1, wherein the clinical case capture tool comprises parameters and values selected from Biomedical Controlled English (BCE). 8. The platform of embodiment 1, wherein the clinical case capture tool is adapted for use by a specially-trained clinical analyst. 9. The platform of embodiment 1, wherein the clinical case capture tool generates a summary comprising a cancer treatment rationale. 10. The platform of embodiment 1, wherein the clinical case capture tool further comprises a software module for obtaining panomic data for the patient. 11. The platform of embodiment 1, wherein the clinical case capture tool further comprises a software module for obtaining one or more electronic medical records for the patient. 12. The platform of embodiment 1, wherein the clinician survey application conducts an adaptive Delphi survey process. 13. The platform of embodiment 1, wherein the clinician survey application publishes the summary of the captured clinical case to an expert clinical oncology network. 14. The platform of embodiment 1, wherein the clinician survey application comprises a software module for converting the plurality of vetted treatment rationales from a Controlled Natural Language (CNL) into a formal logic. 15. The platform of embodiment 1, wherein the clinical decision engine conducts a Bayesian decision process. 16. The platform of embodiment 15, wherein the clinical decision engine utilizes the Bayesian decision process to coordinate decisions across a plurality of patients. 17. The platform of embodiment 15, wherein the Bayesian decision process utilizes a Bayesian network. 18. The platform of embodiment 15, wherein the Bayesian decision process utilizes a hill climbing algorithm. 19. The platform of embodiment 1, wherein the clinical decision engine allows the user to select the cohort based on one or more of: data source, age, gender, at least one biomarker, genetic variant, tumor type, cancer stage, tumor location, lymph node status, treatment, treatment order, desired evidence threshold, and survival. 20. The platform of embodiment 1, wherein the clinical decision engine further comprises a software module utilizing vetted treatment rationales to generate one or more inferential chains that comprise at least one treatment hypothesis. 21. The platform of embodiment 20, wherein the one or more inferential chains are generated using a machine learning algorithm. 22. A computer-implemented method of conducting a virtual clinical trial comprising: (a) providing an adaptive interface for recording clinical details pertaining to a patient case, the interface comprising a plurality of selectable templates, each template comprising one or more parameters with selectable values; (b) generating a standardized summary of the patient case comprising at least one treatment rationale; (c) identifying any patient case summaries that are similar to the patient case to form a case series; (d) publishing the case series to an expert clinician network; (e) conducting an adaptive survey of the network to validate the at least one treatment rationale and optionally ranking or prioritizing the at least one treatment rationale; (f) accruing the case series having validated treatment rationales to a knowledge base; (g) applying a machine learning algorithm to the knowledge base to predict a response of the patient to the at least one treatment rationale; and (h) providing an outcome registry to collect a clinical outcome for the patient and accrue the outcome to the case series in the knowledge base. 23. A computer-implemented method of conducting a virtual clinical trial comprising: (a) providing an adaptive interface for receiving user input corresponding to a disease profile, the interface comprising a plurality of selectable parameters with selectable values; (b) identifying any patient case summaries in a knowledge base that are similar to the disease profile to form a cohort of case summaries having validated treatment rationales; (c) applying a machine learning algorithm to the knowledge base to predict a response of the patient to the at least one treatment rationale; and (d) providing an outcome registry to collect a clinical outcome for the patient and accrue the outcome to the case series in the knowledge base. 24. The method of embodiment 23, wherein the cohort is selected based on one or more of: data source, age, gender, biomarkers, genetic variant, tumor type, tumor location, treatment, treatment order, and survival. 25. The method of embodiment 23, wherein the publishing comprises nanopublication. 26. The method of embodiment 23, wherein the adaptive survey comprises an incremental Delphi process. 27. The method of embodiment 23, wherein comprising injecting a treatment hypothesis and applying the machine learning algorithm to predict an outcome to test the hypothesis. 28. The method of embodiment 26, further comprising determining a value for the hypothesis. 29. The method of embodiment 23, wherein the clinical outcome comprises a measure of reimbursement support. 30. The method of embodiment 29, further comprising determining a reputation score based on the measures of reimbursement support accrued to the knowledge base. 31. A computer-implemented system comprising: a digital processing device comprising: a processor, an operating system configured to perform executable instructions, a memory, and a computer program including instructions executable by the digital processing device to create a clinical case capture application, the application comprising: (a) a software module configured to present a plurality of selectable clinical case templates, each template comprising a plurality of adaptive clinical case parameters, each parameter comprising one or more selectable values; (b) a software module configured to receive input by a specially-trained clinical analyst pertaining to at least one template, parameter, and value to capture a clinical case of a patient; and (c) a software module configured to generate a standardized summary of a captured clinical case, the summary comprising at least one treatment rationale for the patient. 32. The clinical case capture application of embodiment 31, further comprising a software module for converting user input from a Controlled Natural Language (CNL) into a formal logic. 33. The clinical case capture application of embodiment 31, further comprising a software module for generating a standardized summary of each clinical case captured. 34. The clinical case capture application of embodiment 31, further comprising a treatment explorer generating ranked treatment options based on clinical case information. 35. The clinical case capture application of embodiment 31, further comprising a template, parameters, and values derived from a clinical modeling language. 36. The clinical case capture application of embodiment 31, further comprising parameters and values selected from Controlled Natural Language (CNL). 37. The clinical case capture application of embodiment 31, further comprising parameters and values selected from Biomedical Controlled English (BCE). 38. The clinical case capture application of embodiment 31, wherein the clinical case capture application is adapted for use by a specially-trained clinical analyst. 39. The clinical case capture application of embodiment 31, wherein the clinical case capture application generates a summary comprising a cancer treatment rationale. 40. The clinical case capture application of embodiment 31, further comprising a software module for obtaining panomic data for the patient. 41. The clinical case capture application of embodiment 31, further comprising a software module for obtaining one or more electronic medical records for the patient. 42. A computer-implemented system comprising: a digital processing device comprising: a processor, an operating system configured to perform executable instructions, a memory, and a computer program including instructions executable by the digital processing device to create an adaptive clinician survey application comprising: (a) a software module configured to publish a summary of a clinical case comprising at least one treatment rationale to an expert clinician network; (b) a software module configured to conduct an adaptive Delphi survey process of the network to collect vetting feedback pertaining to a treatment rationale of the summary; and (c) a software module configured to store a plurality of vetted treatment rationales to form a knowledge base. 43. The system of embodiment 42, wherein the adaptive clinician survey application conducts an adaptive Delphi survey process. 44. The system of embodiment 42, wherein the adaptive clinician survey application publishes the summary of the captured clinical case to an expert clinical oncology network. 45. The system of embodiment 42, wherein the adaptive clinician survey application comprises a software module for converting the plurality of vetted treatment rationales from a Controlled Natural Language (CNL) into a formal logic. 46. A computer-implemented system comprising: a digital processing device comprising: a processor, an operating system configured to perform executable instructions, a memory, and a computer program including instructions executable by the digital processing device to create a Bayesian clinical decision engine comprising: (a) a knowledge base comprising a plurality of summarized clinical cases, each case comprising at least one treatment rationale vetted by a network of expert clinicians; (b) a software module configured to allow a user to identify a cohort of the cases and a treatment hypothesis; (c) a software module configured to apply an algorithm utilizing the knowledge base to provide one or more ranked treatment protocols; and (d) a software module configured to provide a registry for collecting outcome data to train the algorithm. 47. The system of embodiment 46, wherein the clinical decision engine conducts a Bayesian decision process. 48. The system of embodiment 47, wherein the clinical decision engine utilizes the Bayesian decision process to coordinate decisions across a plurality of patients. 49. The system of embodiment 47, wherein the Bayesian decision process utilizes a Bayesian network. 50. The system of embodiment 47, wherein the Bayesian decision process utilizes a hill climbing algorithm. 51. The system of embodiment 46, wherein the clinical decision engine allows the user to select the cohort based on one or more of: data source, age, gender, at least one biomarker, genetic variant, tumor type, cancer stage, tumor location, lymph node status, treatment, treatment order, desired evidence threshold, and survival. 52. The system of embodiment 46, wherein the clinical decision engine further comprises a software module utilizing vetted treatment rationales to generate one or more inferential chains that comprise at least one treatment hypothesis. 53. The system of embodiment 52, wherein the one or more inferential chains are generated using a machine learning algorithm. 54. The system of embodiment 46, wherein the algorithm utilizes probabilistic logic. 55. The system of embodiment 46, wherein the algorithm utilizes at least one machine learning model. 56. The system of embodiment 55, wherein the at least one machine learning model is selected from an artificial neural network, a support vector machine, a decision tree, or a combination thereof. 57. A computer-implemented method, comprising: (a) normalizing a plurality of treatment rationales to generate a plurality of normalized treatment rationales; and (b) applying an algorithm for processing the plurality of normalized treatment rationales to determine a treatment for a subject. 58. A computer-implemented system comprising: (a) a network adaptor configured to communicate with a network of nodes, each node in the network of nodes comprising a data source; and (b) a processor communicatively coupled to the network adaptor, wherein the processor is configured to (i) generate a knowledge database from the network, (ii) receive an input for a subject, and (ii) based at least in part on the input, apply an algorithm to navigate the knowledge database to determine a treatment recommendation for the subject. 59. A computer-implemented method, comprising: (a) generating a knowledge base from a plurality of treatment rationales; (b) receiving a first input for a subject; (c) applying, via a processor, an algorithm to process the first input and the plurality of treatment rationales; and (d) recommending a treatment for the subject. 60. A computing platform comprising: (a) a processor configured to provide a biomedical reasoning capture tool for capturing database records in a language representation comprising: (i) a software module that permits input of database records describing one or more problem settings; (ii) a software module that permits input of database records describing a plurality of choices proposed, selected, and/or rejected with regard to the one or more problem settings; (iii) a software module that permits input of database records describing a plurality of treatment rationales for the proposal, selection, and/or rejection of the plurality of choices; comprised of one or more of a plurality of other database records, recursively; (b) a software module for transforming the database records captured in a) into additional records, in a database or file, from one of a plurality of possible formal or natural language representations into one of a plurality of semantic representations suitable for software analysis; and (c) a processor configured with at least one such software application, as described in b), that executes algorithmic searches over the database, and produces the database records before or after transformation. 61. The platform of embodiment 60, wherein the database records are entered using or are transformed into a free-form natural language representation. 62. The platform of embodiment 60, wherein a representation used either to input the database records or into which the database records are transformed is a controlled natural language. 63. The platform of embodiment 60, wherein a representation used to input the database records or into which the database records are transformed is a formal language 64. The platform of embodiment 63, wherein the database records are represented in JSON and comprise terms in a form of tags. 65. The platform of embodiment 60, wherein a representation used to input the database records or into which the database records are transformed is a free-form language, a controlled language, natural, a formal language, or a combination thereof. 66. The platform of embodiment 60, wherein a representation used to input the database records or into which the database records are transformed is created by a user by selection from among a plurality of parameters, and by selection from among a plurality of values for each parameter. 67. The platform of embodiment 66, wherein the selection is carried out through a graphical user interface. 68. The platform of embodiment 66, wherein some parameters or relationships between the parameters is selected by moving graphical representations of parameters or values on a graphical user interface. 69. The platform of any of embodiments 60-66, further comprising a software module executing at least one algorithm specified by the user. 70. The platform of any of embodiments 60-66, further comprising a software module executing at least one algorithm specified by the user in any of a plurality of formal computer programming languages. 71. The platform of any of embodiments 60-70, wherein the at least one application is a decision engine allowing one or more persons to rank choices based upon the content of the database records. 72. The platform of any of embodiments 60-70, wherein the platform is used a clinical medical setting, wherein the problems are clinical cases, the choices are medical tests or treatments, and the treatment rationales provide reasons that the choices were proposed, selected, or rejected. 73. The platform of any of embodiments 60-70, further comprising a software application that produces a summary of database records selection by a search application. 74. The platform of any of embodiments 60-70, wherein the summary produced results in an output that conforms to one or more of a plurality of reporting templates selected by a user. 75. The platform of embodiment 74, wherein the one or more of the plurality of reporting templates produces graphical report components. 76. The platform of embodiment 74, wherein the one or more of the plurality of reporting templates produces report components. 77. The platform of embodiment 74, wherein the one or more of the plurality of reporting templates produces reports expressed using a representation selected from a free-form language, a controlled language, natural, a formal language, or a combination thereof. 78. The platform of any of embodiments wherein the database records are input through extraction from another database. 79. The platform of embodiment 78, wherein the database records extracted from the another database are transformed before loading into a representation appropriate for a database of the platform. The platform of any of embodiments 60-77, wherein the at least one application allows users of the platform to score entries in the database in accord with one or more of a plurality of dimensions, wherein the scores are associated with one or more of the database records. 81. The platform of embodiment 80, wherein the scoring is performed by a computer algorithm. 82. The platform of embodiment 80, wherein scoring is performed by a combination of a computer algorithm and one or more persons, as specified by a workflow algorithm. 83. The platform of embodiment 82, wherein the scoring workflow algorithm is specified by the users of the platform. 84. The platform of embodiment 83, wherein an ability to specify the scoring workflow is limited to a subset of users. 85. The platform of any of embodiments 60-84, wherein the platform is deployed locally within an institution on computers and networks under control of persons employed by that institution. 86. The platform of any of embodiments 60-84, wherein the platform is deployed remotely on computers and networks under the control of persons employed by an organization that is not a user organization. 87. A computing platform comprising a processor configured to provide a self-improving biomedical decision aid comprising: (a) a software module receiving input comprising a plurality of problem descriptions by a plurality of users; (b) a software module receiving input of a plurality of plausible action choices for responding to the plurality of problems; (c) a software module selecting statistically one or more optimal choices from among the plurality of plausible actions; (d) a software module ranking the optimal choices to provide a greatest global information gain to an overall decision process over all problems, action choices, and users; (e) a software module communicating a list of the optimal choices and rankings to one or more of the users; (f) a software module receiving input of a decision by a user; and (g) a software module receiving input of a reason for making the decision. 88. The platform of embodiment 87, wherein the problems, choices, and rationales are received as or transformed into representations selected from the group consisting of a free-form language, a controlled language, natural, a formal language, or a combination thereof. 89. The platform of embodiment 87, wherein biomedical decision aid provides decision support that facilitates human-machine collaborative work. 90. The platform of embodiment 89, wherein (a)-(g) are performed manually. 91. The platform of any of embodiments 87-90, wherein one or more human users participate in decision ranking computations performed by the biomedical decision aid. 92. The platform of embodiment 87, wherein the platform provides tools to support collaboration between a plurality of humans when more than one human is involved in a ranking computation. 93. A computing platform comprising at least one processor configured to provide: (a) a clinical case capture tool configured to obtain clinical case information to capture a clinical case of a patient; (b) a clinician survey application configured to: (i) publish a summary of said captured clinical case and at least one treatment rationale corresponding to said captured clinical case to an expert clinician network; (ii) collect vetting feedback for said at least one treatment rationale corresponding to said summary through said expert clinician network; and (iii) store said at least one vetted treatment rationale on a knowledge base comprising a plurality of treatment rationales; and (c) a clinical decision engine configured to: (i) collect treatment and outcome data corresponding to said captured clinical case and storing said treatment and outcome data on said knowledge base; and (ii) training or updating an algorithm using said knowledge base, said algorithm configured to evaluate a clinical case and provide one or more treatment protocols. 94. The platform of embodiment 93, wherein the clinical case capture tool comprises a software module for converting user input from a Controlled Natural Language (CNL) into a formal logic. 95. The platform of embodiment 93, wherein the clinical case capture tool generates a standardized summary of each clinical case captured. 96. The platform of embodiment 93, wherein the clinical case capture tool comprises a treatment explorer generating ranked treatment options based on clinical case information. 97. The platform of embodiment 93, wherein the clinical case capture tool comprises template, parameters, and values derived from a clinical modeling language. 98. The platform of embodiment 93, wherein the clinical case capture tool comprises parameters and values selected from Controlled Natural Language (CNL). 99. The platform of embodiment 93, wherein the clinical case capture tool comprises parameters and values selected from Biomedical Controlled English (BCE). 100. The platform of embodiment 93, wherein the clinical case capture tool is adapted for use by a specially-trained clinical analyst. 101. The platform of embodiment 93, wherein the clinical case capture tool generates a summary comprising a cancer treatment rationale. 102. The platform of embodiment 93, wherein the clinical case capture tool further comprises a software module for obtaining panomic data for the patient. 103. The platform of embodiment 93, wherein the clinical case capture tool further comprises a software module for obtaining one or more electronic medical records for the patient. 104. The platform of embodiment 93, wherein the clinician survey application conducts an adaptive Delphi survey process. 105. The platform of embodiment 93, wherein the clinician survey application publishes the summary of the captured clinical case to an expert clinical oncology network. 106. The platform of embodiment 93, wherein the clinician survey application comprises a software module for converting the plurality of vetted treatment rationales from a Controlled Natural Language (CNL) into a formal logic. 107. The platform of embodiment 93, wherein the clinical decision engine conducts a Bayesian decision process. 108. The platform of embodiment 107, wherein the clinical decision engine utilizes the Bayesian decision process to coordinate decisions across a plurality of patients. 109. The platform of embodiment 107, wherein the clinical decision engine utilizes the Bayesian decision process to provide said one or more treatment protocols for said clinical case in step (c)(ii). 110. The platform of embodiment 109, wherein the clinical decision engine ranks said one or more treatment protocols according to predicted outcome. 111. The platform of embodiment 110, wherein the clinical decision engine identifies the top ranked treatment protocol from treatment protocols that have overlapping variance by selecting the treatment protocol that provides greater information gain. 112. The platform of embodiment 107, wherein the Bayesian decision process utilizes a Bayesian network. 113. The platform of embodiment 107, wherein the Bayesian decision process utilizes a hill climbing algorithm. 114. The platform of embodiment 93, wherein the clinical decision engine allows a user to select a cohort and a treatment protocol. 115. The platform of embodiment 114, wherein the clinical decision engine allows the user to select the cohort based on one or more of: data source, age, gender, at least one biomarker, genetic variant, tumor type, cancer stage, tumor location, lymph node status, treatment, treatment order, desired evidence threshold, and survival. 116. The platform of embodiment 93, wherein the clinical decision engine is further configured to use vetted treatment rationales to generate one or more inferential chains that comprise at least one treatment hypothesis. 117. The platform of embodiment 20, wherein the one or more inferential chains are generated using a machine learning algorithm. 118. A computer-implemented method of conducting a virtual clinical trial, comprising: (i) providing an adaptive interface for recording clinical details pertaining to a patient case; (j) generating a standardized summary of the patient case; (k) generating a case series comprising the standardized summary of the patient case and any similar patient case summaries; (l) publishing the case series to an expert clinician network; (m) conducting an adaptive survey of the network to validate at least one treatment rationale for the case series; (n) accruing the case series having validated treatment rationales to a knowledge base; (o) applying a machine learning algorithm to the knowledge base to predict a response of the patient to the at least one treatment rationale; and (p) providing an outcome registry to collect a clinical outcome for the patient and accrue the outcome to the case series in the knowledge base. 119. A computer-implemented method of conducting a virtual clinical trial, comprising: a) obtaining clinical details pertaining to a patient case corresponding to a disease profile; b) applying a machine learning algorithm to the patient case to generate one or more treatment options and associated treatment rationales; and c) conducting an adaptive survey of an expert clinician network to validate at least one of the one or more treatment options and associated treatment rationales for the patient case; d) collecting a treatment decision and a clinical outcome for the patient; and e) updating the machine learning algorithm based on the treatment decision and clinical outcome; and (e) re-analyzing the patient case using the machine learning algorithm to generate one or more updated treatment options and associated treatment rationales. 120. The method of embodiment 23, further comprising identifying any patient cases in a knowledge base that are similar to the disease profile to form a cohort of case summaries having validated treatment rationales 121. The method of embodiment 120, wherein the cohort is selected based on one or more of: data source, age, gender, biomarkers, genetic variant, tumor type, tumor location, treatment, treatment order, and survival. 122. The method of embodiment 23, wherein the adaptive survey comprises an incremental Delphi process. 123. The method of embodiment 23, further comprising determining one or more values for the one or more treatment options. 124. The method of embodiment 23, wherein the clinical outcome comprises a measure of reimbursement support. 125. The method of embodiment 29, further comprising determining a reputation score based on the measures of reimbursement support accrued to the knowledge base. 126. The method of embodiment 23, wherein the machine learning algorithm comprises a Bayesian decision process. 127. The method of embodiment 126, wherein the Bayesian decision process is used to coordinate decisions across a plurality of patients. 128. The method of embodiment 126, wherein the Bayesian decision process utilizes a Bayesian network. 129. The method of embodiment 126, wherein the Bayesian decision process utilizes a hill climbing algorithm. 130. The method of embodiment 23, wherein the machine learning algorithm ranks said one or more treatment options according to predicted outcome. 131. The method of embodiment 130, wherein a top ranked treatment option is selected from treatment options that have overlapping variance by identifying the treatment option that provides the greatest information gain. 132. The method of embodiment 23, further comprising receiving user selection of a cohort and a treatment option. 133. The method of embodiment 132, wherein user selects the cohort based on one or more of: data source, age, gender, at least one biomarker, genetic variant, tumor type, cancer stage, tumor location, lymph node status, treatment, treatment order, desired evidence threshold, or survival. 134. The method of embodiment 23, wherein the machine learning algorithm utilizes validated treatment rationales to generate one or more inferential chains that comprise at least one treatment hypothesis. 135. The method of embodiment 134, wherein the one or more inferential chains are generated using a machine learning algorithm. 136. The method of embodiment 23, further comprising providing a searchable knowledge base to the expert clinician network. 137. The method of embodiment 136, wherein the searchable knowledge base comprises patient cases and associated treatment options, treatment rationales, and outcomes. 138. A computer-implemented system comprising: a digital processing device comprising: a processor, an operating system configured to perform executable instructions, a memory, and a computer program including instructions executable by the digital processing device to create a Bayesian clinical decision engine comprising: (e) a knowledge base comprising a plurality of summarized clinical cases; (f) a software module configured to apply an algorithm to a knowledge base comprising a plurality of summarized clinical cases to segment said clinical cases into cohorts; (g) a software module configured to apply an algorithm utilizing the knowledge base to generate a treatment protocol for at least one cohort; (h) a software module configured to suggest the treatment protocol for a clinical case belonging to the at least one cohort; and (i) a software module configured to collect outcome data to train the algorithm. 139. The system of embodiment 46, wherein the clinical decision engine conducts a Bayesian decision process. 140. The system of embodiment 47, wherein the clinical decision engine utilizes the Bayesian decision process to coordinate decisions across a plurality of patients. 141. The system of embodiment 47, wherein the Bayesian decision process utilizes a Bayesian network. 142. The system of embodiment 47, wherein the Bayesian decision process utilizes a hill climbing algorithm. 143. The system of embodiment 46, wherein the clinical decision engine segments the clinical cases into cohorts based on one or more of: data source, age, gender, at least one biomarker, genetic variant, tumor type, cancer stage, tumor location, lymph node status, treatment, treatment order, desired evidence threshold, and survival. 144. The system of embodiment 46, wherein the clinical decision engine further comprises a software module utilizing vetted treatment rationales to generate one or more inferential chains that comprise at least one treatment hypothesis. 145. The system of embodiment 52, wherein the one or more inferential chains are generated using a machine learning algorithm. 146. The system of embodiment 46, wherein the algorithm utilizes probabilistic logic. 147. The system of embodiment 46, wherein the algorithm utilizes at least one machine learning model. 148. The system of embodiment 55, wherein the at least one machine learning model is selected from an artificial neural network, a support vector machine, a decision tree, or a combination thereof 149. A computing platform comprising: (a) a knowledge database comprising a plurality of clinical cases and treatment options and treatment rationales associated with said plurality of clinical cases. (b) a clinical case capture tool configured to capture a clinical case; (c) a clinician survey application configured to publish the clinical case to an expert clinician network and collect feedback for one or more treatment options and associated treatment rationales for the clinical case; and (d) a clinical decision engine configured to provide a user with at least one recommendation of the one or more treatment options based on said feedback. 150. The platform of embodiment 149, wherein the one or more treatment options and associated treatment rationales are mined or crowdsourced from peer reviewed literature, conferences, medical data, a physician for the clinical case, an expert in a disease profile of the clinical case, or any combination thereof. 151. The platform of embodiment 149, wherein the recommendation comprises a ranking of the one or more treatment options. 152. The platform of embodiment 149, wherein the clinical case capture tool comprises a software module for converting user input from a Controlled Natural Language (CNL) into a formal logic. 153. The platform of embodiment 149, wherein the user is a treating physician of a patient of the clinical case. 154. The platform of embodiment 149, wherein the clinical case capture tool generates a standardized summary of each clinical case captured. 155. The platform of embodiment 149, wherein the clinical case capture tool comprises a treatment explorer generating ranked treatment options based on clinical case information. 156. The platform of embodiment 149, wherein the clinical case capture tool comprises templates, parameters, and values derived from a clinical modeling language. 157. The platform of embodiment 149, wherein the clinical case capture tool comprises parameters and values selected from Controlled Natural Language (CNL). 158. The platform of embodiment 149, wherein the clinical case capture tool comprises parameters and values selected from Biomedical Controlled English (BCE). 159. The platform of embodiment 149, wherein the clinical case capture tool is adapted for use by a specially-trained clinical analyst. 160. The platform of embodiment 149, wherein the clinical case capture tool generates a summary comprising a cancer treatment rationale. 161. The platform of embodiment 149, wherein the clinical case capture tool further comprises a software module for obtaining panomic data for the patient. 162. The platform of embodiment 149, wherein the clinical case capture tool further comprises a software module for obtaining one or more electronic medical records for the patient. 163. The platform of embodiment 149, wherein the clinician survey application conducts an adaptive Delphi survey process. 164. The platform of embodiment 149, wherein the clinician survey application publishes the summary of the captured clinical case to an expert clinical oncology network. 165. The platform of embodiment 149, wherein the clinician survey application comprises a software module for converting the plurality of vetted treatment rationales from a Controlled Natural Language (CNL) into a formal logic. 166. The platform of embodiment 149, wherein the clinical decision engine conducts a Bayesian decision process. 167. The platform of embodiment 166, wherein the clinical decision engine utilizes the Bayesian decision process to coordinate decisions across a plurality of patients. 168. The platform of embodiment 166, wherein the Bayesian decision process utilizes a Bayesian network. 169. The platform of embodiment 166, wherein the Bayesian decision process utilizes a hill climbing algorithm. 170. The platform of embodiment 149, wherein the clinical decision engine allows the user to select the cohort based on one or more of: data source, age, gender, at least one biomarker, genetic variant, tumor type, cancer stage, tumor location, lymph node status, treatment, treatment order, desired evidence threshold, and survival. 171. The platform of embodiment 149, wherein the clinical decision engine further comprises a software module utilizing vetted treatment rationales to generate one or more inferential chains that comprise at least one treatment hypothesis. 172. The platform of embodiment 20, wherein the one or more inferential chains are generated using a machine learning algorithm. 173. The platform of embodiment 149, wherein the knowledge base is updated with outcome data for the captured clinical case. 174. The platform of embodiment 173, wherein the updated knowledge base is analyzed using a machine learning algorithm to coordinate a plurality of ongoing clinical cases. 175. A computer-implemented method of conducting a virtual clinical trial comprising: (a) providing an interface for recording clinical details pertaining to a patient case; (b) generating a standardized case summary of the patient case; (c) publishing the case summary to an expert clinician network; (d) conducting a survey of the network to validate and rank one or more treatment options and associated treatment rationales; (e) accruing the case summary with the validated and ranked one or more treatment options and associated treatment rationales to a knowledge base; (f) presenting the validated and ranked one or more treatment options and associated treatment rationales to a physician responsible for treating the patient in the patient case; (g) receiving a chosen treatment option and associated treatment rationale from the physician and accruing chosen treatment option and associated treatment rationale to the case summary in the knowledge base; and (h) collecting clinical results and outcomes for the patient case and accruing the clinical results and outcomes to the case summary in the knowledge base. 176. A computer-implemented method of conducting a virtual clinical trial comprising: (a) providing a clinical case corresponding to a patient using a clinical case capture tool, wherein the clinical case is published to an expert clinician network for validation of at least one treatment option and associated treatment rationale; (b) receiving a treatment recommendation based on the validation of the at least one treatment option and associated treatment rationale; and (c) providing the patient with a treatment according to the treatment recommendation. 177. The method of embodiment 23, further comprising uploading the treatment and an outcome of the clinical case. 178. The method of embodiment 23, wherein the clinical outcome comprises a measure of reimbursement support. 179. The method of embodiment 29, further comprising determining a reputation score based on the measures of reimbursement support accrued to the knowledge base. 180. The method of embodiment 23, further comprising receiving an updated treatment recommendation comprising a change to the treatment. 181. The method of embodiment 180, further comprising switching the patient to a new treatment based on the updated treatment recommendation. 182. The method of embodiment 23, wherein the treatment recommendation is generated using a knowledge base comprising a plurality of clinical cases, treatment rationales, and outcome data. 183. The method of embodiment 182, further providing outcome data to the knowledge base. 184. The method of embodiment 183, wherein the knowledge base is a searchable database accessible by healthcare providers. 185. The method of embodiment 182, wherein the at least one treatment option is generated by a machine learning algorithm trained using information in the knowledge base. 186. The method of embodiment 185, wherein the machine learning algorithm comprises a Bayesian learning process. 187. The method of embodiment 185, wherein the machine learning algorithm dynamically or periodically re-evaluates the clinical case to generate updated analysis of available treatment options and treatment rationales. 188. The method of embodiment 23, wherein the treatment recommendation comprises a plurality of treatment options and associated treatment rationales. 189. The method of embodiment 188, wherein the plurality of treatment options and associated treatment rationales are ranked.

EXAMPLES

Example 1: Virtual Trial Platform with Informatics Capability

Using systems and methods of the present disclosure, a Virtual Trial Platform can be implemented to conduct virtual trials, as described herein. The Virtual Trial Platform can include three core capabilities: informatics capability, drug access capability, and real-world data capture.

The informatics capability can support collaborative human-machine treatment planning and coordination by Virtual Tumor Boards (VTBs), as described herein. The informatics capability can be implemented by three modules: a treatment planning module for individual patients; a knowledge network module for sharing treatment options and rationales across VTBs; and a Global Cumulative Treatment Analysis (GCTA) module performing a set of algorithms that coordinates treatment decisions across all patients to maximize learning.

The treatment planning module can be implemented as follows. The VTBs provide individualized treatment options and rationales (TRRs) to a patient's treating physician (TP). Using the Virtual Trial Platform, an appropriately skilled facilitator (e.g., a physician, cancer scientist or nurse navigator) first selects several (e.g., about 3, 4, or 5) experts with expertise relevant to the patient's case. These experts are selected from a pool by matching their interests, qualifications, and availabilities to the patient's case (e.g., cancer subtype, biomarkers, and past therapies, as well as the complexity and urgency of the case). The Virtual Trial Platform then helps the facilitator curate the case for presentation to the VTB, distilling the most relevant information from the patient's medical record and selecting an initial 'Leaderboard' of about 6-12 top treatment options with rationales. This selection is based on past recommendations for similar patients, how often those treatments were actually pursued, and how well they worked.

Next, the facilitator moderates a software-mediated iterative process, whereby VTB members discuss, refine, and rank the Leaderboard options, to converge on a consensus recommendation. At each step in this process, members of the expert pool can provide additional rationales (e.g., pros and cons) for each of the listed options, suggest new options with rationales, and participate in structured polls conducted by the facilitator to prioritize and cut options (e.g., voting, rank ordering, and Delphi). A member of the expert pool can also recommend additional tests and analyses to increase their confidence. At the end of each round, the facilitator integrates the responses and creates a new Leaderboard. The process continues until convergence is reached on a small equipoise set of top options. VTB members can participate in this process via a web browser, e-mail, and/r texting.

The equipoise option set (typically about 3, 4, or 5) is presented to the treating physician along with their rationales and any available data on clinical outcomes. The final decision as to what clinical action to undertake is always up to the treating physician (TP), in consultation with the patient. They are free to select an option from the equipoise set, or alternatively another option as desired. Through the platform they report which option they chose, why they chose this option, and how well it worked, which is how the Virtual Trial Platform continually learns. The VTB recommendations, physician decisions, rationales, and clinical results are captured, analyzed, and used to inform the treatment of future patients.

Leaving the final decision up to the TP is important for multiple reasons. First, rather than engaging in the practice of medicine, the Virtual Trial Platform provides information to physicians and captures data in a registry. Second, the Virtual Trial Platform protocol is to be viewed by IRBs as an observational registry trial. Such trials are considered to have minimal risk and are usually exempted from review. From an IRB's perspective, the Virtual Trial Platform facilitates observation of the VTBs and TPs making decisions and capturing the results. However, because the decisions are based in part on information provided by the Virtual Trial Platform, there is an opportunity to conduct interventional studies under the rubric of a registry trial. Third, AI-based systems are not yet able to accurately and efficiently determine treatment decisions; and even if they were, physicians do not trust decision outputs generated by a "black box" machine learning algorithm. From an ethical perspective, the Virtual Trial Platform assists physicians in their decision-making by augmenting human intelligence rather than replacing it. Further, providing explicit treatment rationales mitigates or eliminates the issues with the "black box" issue of machine learning algorithms.

The Virtual Trial Platform also advantageously captures the rationales underlying both VTB deliberations and physician decisions. Such rationales are seldom captured in medical records, yet are essential for judging the relevance of past recommendations and decisions to future patients, whether by AI software or human experts. Capturing this information longitudinally for a given patient across multiple lines of therapy is very important for optimizing multi-therapy regimens, as explained below. For example, Controlled Biomedical English (CBE) can be used to encode these rationales into a form accessible to both humans and computers, as described herein.

The knowledge network module can be implemented as follows. All VTBs share knowledge and data through the Treatment Planner's TRR repository and registry. This de-facto knowledge network provides participants with an unprecedented view of what their colleagues at other institutions are recommending for similar patients as well as real time, real-world data on how well these treatments are working. This can be considered a real-time version of "Up-to-Date" (a journal of best practice), searchable by the particulars of a case, molecular pathway, or therapeutic. The knowledge and data are valuable to bio-pharmaceutical companies, payers, and investors, providing a unique window into the thinking process of physicians and scientists in the field of clinical oncology.

As described herein, TRRs can be extracted from a complementary knowledge source: the live discussions of Molecular Tumor Boards (MTBs) at major cancer centers. Such a process uses human facilitators to capture treatment recommendations, and solicit rationales if they were not already provided. The resulting discussions are then translated semi-automatically into Controlled Biomedical English, which the software uses to create a searchable knowledge base of TRRs. MTBs typically consider a half dozen or so cases a week, and are not scalable. Further, many MTBs are run like academic journal clubs, helping physicians learn about precision medicine. This model may be extended to VTBs without necessarily replacing or excluding these MTBs. A goal is to rapidly scale the knowledge network by pooling cases and TRRs from all sources, including VTBs, MTBs, individual physicians, and the literature, as well as by mining clinical data.

The global cumulative treatment analysis (GCTA) module can be implemented as follows. Since the novel treatment hypotheses generated by VTBs and MTBs may or may not be correct, they are tested in a clinical trial. The Virtual Trial Platform enables these unique hypotheses to be tested with high efficiency, at significantly reduced time and cost as compared to a traditional clinical trial. For example, such savings can potentially amount to 90% or more compared to the gold standard randomized controlled trial: answers in months versus years, per-patient costs of about $2,000 versus as much as $50,000, and far fewer patients. For treatments with strong efficacy signals, a dynamically defined cohort of about 10-20 patients in the adaptive Bayesian process described herein can provide the same strength of evidence as a static cohort of several hundred patients in a traditional clinical trial based on frequentist statistical inference. In deadly cancers, strong signals are far more significant. These efficiencies are achieved because the Virtual Trial Platform is always on (with no start up delays, or delays between phases, since all patients are pre-consented), costs are amortized across all therapies in the system, and the GCTA algorithm allocates patients to treatments in a globally efficient way that enables more hypotheses to be tested with far fewer patients. This approach creates a Succeed Fast/Fail Fast dynamic that benefits all parties involved: patients receive the best available treatment for their individual case (which seldom happens in traditional drug-centric trials), and bio-pharmaceutical companies reduce costs incurred in pursuing treatments that are likely to fail in their trial, or even worse in the marketplace when competing against better drugs.

In particular, the Virtual Trial Platform can be deployed using cohorts of patients with aggressive diseases such as brain cancer (adult and pediatric) and pancreatic cancer. Because of the high unmet need and aggressiveness of these diseases, the Virtual Trial Platform can enable physicians to learn quickly whether a given intervention is having an effect.

The GCTA comprises algorithms which attempt to replicate successes and discard failures, expanding the cohorts of treatments that appear to be working, and shrinking the cohorts of those treatments that do not appear to be working. This approach can close the learning loop, enabling the human-machine system to continually improve treatments and outcomes, thereby optimizing system-wide information gain. Many additional features can be added to the Virtual Trial Platform to improve performance, including resolving an equipoise set of options by prioritizing those that maximize information gain. The "information gain" is used in the spirit of exploration/exploitation tradeoffs from AI planning algorithms; if there is no clear reason to prefer one drug to another, then the drug for which more data would be most helpful is prioritized (e.g., if everyone else is choosing drug A, then try drug B, or vice versa; or if the variance among treatment options overlap (clinical equipoise), then select the high-risk, high-variance option because it maximizes both the chance of a cure and system-wide information gain). Further, cohorts can be refined dynamically based not only on drug response, but on a high-dimensional vector of patient attributes. In lieu of traditional endpoints in a drug-focused trial, the data is analyzed continuously in real time, using Bayesian algorithms that determine when enough evidence is obtained for a given cohort to warrant accelerated approval. Together, these features enable the Virtual Trial Platform to efficiently learn what factors predict which treatments are best for an individual patient (e.g., as described in Shrager and Tenenbaum, "Rapid learning for precision oncology," Nat. Rev. Clin. Oncol., 11(2): 109-18, February 2014, especially including the algorithms/models utilized to generate treatment options or decisions and the validation and refinement of said models, which is hereby incorporated by reference in its entirety).

The Virtual Trial platform may advantageously addressing cancer as a "small-data" problem. For example, regularization techniques, which are used when building models of logistic regression in machine learning, can be used for Bayesian models as well and can be applied to avoid overfitting. Using systems and methods of the present disclosure, a patient segmentation machine-learning approach can be performed with techniques to avoid overfitting the model to optimize the recommendation of therapy options. Such an approach is similar to approaches used to segment and forecast behavior in cases having more input features (e.g., baseline patient characteristics and co-variates) than client or customer cases (e.g., patients).

Example 2: Virtual Trial Platform with Drug Access Capability

Patients and physicians have long faced formidable administrative, regulatory, and financial challenges obtaining the latest investigational therapies through clinical trials and expanded access, or getting reimbursed for approved drugs used off-label. Using systems and methods of the present disclosure, a Virtual Trial Platform can be implemented to conduct virtual trials, as described herein. The Virtual Trial Platform can include three core capabilities: informatics capability, drug access capability, and real-world data capture.

The drug access capability can include a suite of 'clearinghouse' services to help Virtual Trial patients obtain access to investigational therapies through trials and expanded access programs, and get reimbursed for approved drugs that are used off-label. The drug access capability can be implemented by three modules: a trial matching module, an expanded access module, and a module for reimbursement for off-label drugs.

The trial matching module can be implemented as follows. Clinical trials may encounter significant issues, such as negative reception from patients, difficulty in enrolling eligible patients according to trial criteria, and ethical conflicts involved with trial matching services that are compensated to recruit patients to trials that are struggling to accrue. The trial matching module can use the patient registry described herein, along with a partnership with ClinWiki, to gain insights into how trials with data blinding are doing.

The expanded access module can be implemented as follows. Currently, an EA can take a physician about 20 hours to complete an application. Further, while most applications are approved rapidly by the FDA, companies may be reluctant to do it because there is a significant risk of needing to report SAEs while not having any incentive or upside to doing so. EA programs also consume significant internal attention and resources that as a result are not directed to development of a company's products in their primary indication.

Using the expanded access module, drug companies can provide access to their drugs because they are incentivized by opportunities to partner with these companies to develop their drugs in new indications for which they currently lack funding. Because the system is highly efficient, there is an excellent chance that accelerated approvals can be obtained through virtual trials disclosed herein, often before the company's own pivotal trials ever get off the ground. Approval of a first indication makes the drug available for physicians and researchers to use for all medically relevant purposes. The Virtual Trial Platform data may be subsequently used to generate treatment rationale(s) for off label reimbursement.

The module for reimbursement for off-label drugs can encourage responsible exploration of off-label use of existing approved drugs. Using the Virtual Trial Platform, drug makers can seek reimbursement based on the basis of real-world evidence that their drug is effective in a given patient. Thus, such companies can make their drugs available through a clearinghouse for off-label testing in a Virtual Trial, e.g., at no cost to a patient for the first few months. At that time, the companies can use evidence of efficacy to seek reimbursement from the patient's insurer. Additionally, the Virtual Trial Platform may be used for verification and adjudication of a patient's response in performance based contracts between payers and drug companies. The GCTA algorithm can replicate this success in other patients, potentially leading to a compendia listing or label expansion. By enabling such an individual pay-for-performance model, systems and methods of the present disclosure can provide significant advantages toward improving current approaches toward medical reimbursement for therapeutic prescriptions for patients.

The Virtual Trial Platform can produce effectiveness or response data and provide a complete structured medical necessity justification for individual patients that can be electronically signed by their doctor and submitted directly to the patient's insurer. The platform can provide both robust clinical trial evidence of safety or effectiveness similar to a phase ⅔ clinical trial in a population closely matched to the specific patient using ML algorithms as well as evidence of individual patient response indicative of clinical benefit.

For example, the efficiencies of Virtual Trials may enable additional business opportunities that are infeasible in a current clinical trials system. Bio-pharmaceutical and bio-technology companies may often have useful products on the shelf that were abandoned either because they failed in their original indication or because there were other assets that at the time appeared more promising. By performing Virtual Trials using systems and methods of the present disclosure, such companies can economically salvage these products (e.g., drugs) for new indications, or as components of combination therapies. The Virtual Trial Platform enables cost-effective testing of single or combination therapies, developed through rational design or high throughput combinatorial testing. Multi-drug regimens may otherwise be prohibitively expensive to test in traditional trials, which can require cooperation of multiple companies and collectively exponentially more patients than they feasibly enroll. However, thousands of approved and investigational drugs already exist for which no information is available regarding the optimal way to use them. By leveraging the Virtual Trial Platform to optimize multi-drug regimens (e.g., sequences and cocktails), significant advances in precision oncology can be achieved.

Example 3: Virtual Trial Platform with Real-World Data Capture Capability

Using systems and methods of the present disclosure, a Virtual Trial Platform can be implemented to conduct virtual trials, as described herein. The Virtual Trial Platform can include three core capabilities: informatics capability, drug access capability, and real-world data capture.

The real-world data capture capability can include a registry and supporting processes to capture regulatory-grade RWE. This can be performed much more efficiently than clinical trials, in part because the entire dataset collected as part of such clinical trials is not needed by this approach, and the entire dataset collected does not need to be verified through on-site audits. A patient registry can be implemented in RedCap, and modified to support multi-tenancy and multi-data capture forms.

Real-world evidence (RWE) generally refers to data regarding the usage, the potential benefits or risks, of treatments from sources other than randomized clinical trials, including disease registries. Use of such evidence has the potential to allow researchers to answer questions about treatment effects and outcomes efficiently, saving time and money while yielding answers relevant to broader populations of patients than would be possible in a specialized research environment, such as a randomized clinical trial.

Real-world evidence has been increasingly valuable in oncology across several dimensions. First, through the collection and analysis of medical records information, RWE has allowed for the creation of "synthetic control arms" for randomized trials. This approach, in which co-variate matched patients are drawn randomly from a large population to serve as matched controls for patients in a clinical trial provides several benefits. First, it reduces the exposure of patients to placebo in large clinical trials; second, it reduces the cost of clinical trials, encouraging more investigation of active compounds. The 21st Century Cures Act directed the FDA to develop formal mechanisms to make greater use of RWE in support of drug labeling. Several companies have found creative ways to use RWE to support their marketing approval applications, such as using RWE collected on patients in expanded access programs to augment regulatory submissions in rare disease.

As described herein, the Virtual Trial Platform can be leveraged to perform Virtual Trials, which are a highly economical, efficient, and ethical way to test new therapies, and represent a paradigm shift in conducting clinical trials, from approving drugs to curing patients. Every patient receives the best available treatment for their individual case (within an equipoise set). The Virtual Trials can be conducted without inclusion or exclusion criteria because all patients need and deserve to receive the appropriate effective treatment. The Virtual Trials can be conducted without randomized controls because patients being treated with different drugs can serve as cross controls for each other. This process is sometimes referred to as creating synthetic control arms. The Virtual Trials can be conducted without data blinding, which can make it difficult to optimize a given patient's treatment and can lead to situations where many patients discover years later that they were on an ineffective arm or that many other patients were deprived of an effective therapy.

Ultimately, the effectiveness and success of clinical trials requires sufficient enrollment of suitable patients, since they are the scarcest resource. By conducting Virtual Trials, patients can be spared the angst of choosing the right treatment or trial and ultimately getting access to that therapy, Virtual Trials can be advantageous for clinical research because they make the optimal use of available patients, and encourage the rapid, responsible exploration of off-label and multi-drug regimens. Further, Virtual Trials can be advantageous for business needs, by slashing the time and cost of drug development, and opening many business opportunities that are impractical in the current clinical trials system.

Example 4: A Patient-Centric Registry for Enhanced Learning Treatment Selection and Analysis with Outcomes Research Patients and their oncologists often encounter barriers to entry for clinical trials, including inclusion and exclusion criteria that limit the participation of some patients, and/or geographic, financial, or logistical barriers to accessing centers that conduct clinical trials. Further, Patients and their oncologists can encounter challenges obtaining access to off-label, but medically logical therapies due to insurance or other financial barriers and to investigational drugs under expanded access programs due to unfamiliarity with medically-logical investigational options and/or the regulatory and associated institutional processes involved in acquiring drugs under expanded access.

Figure 19:
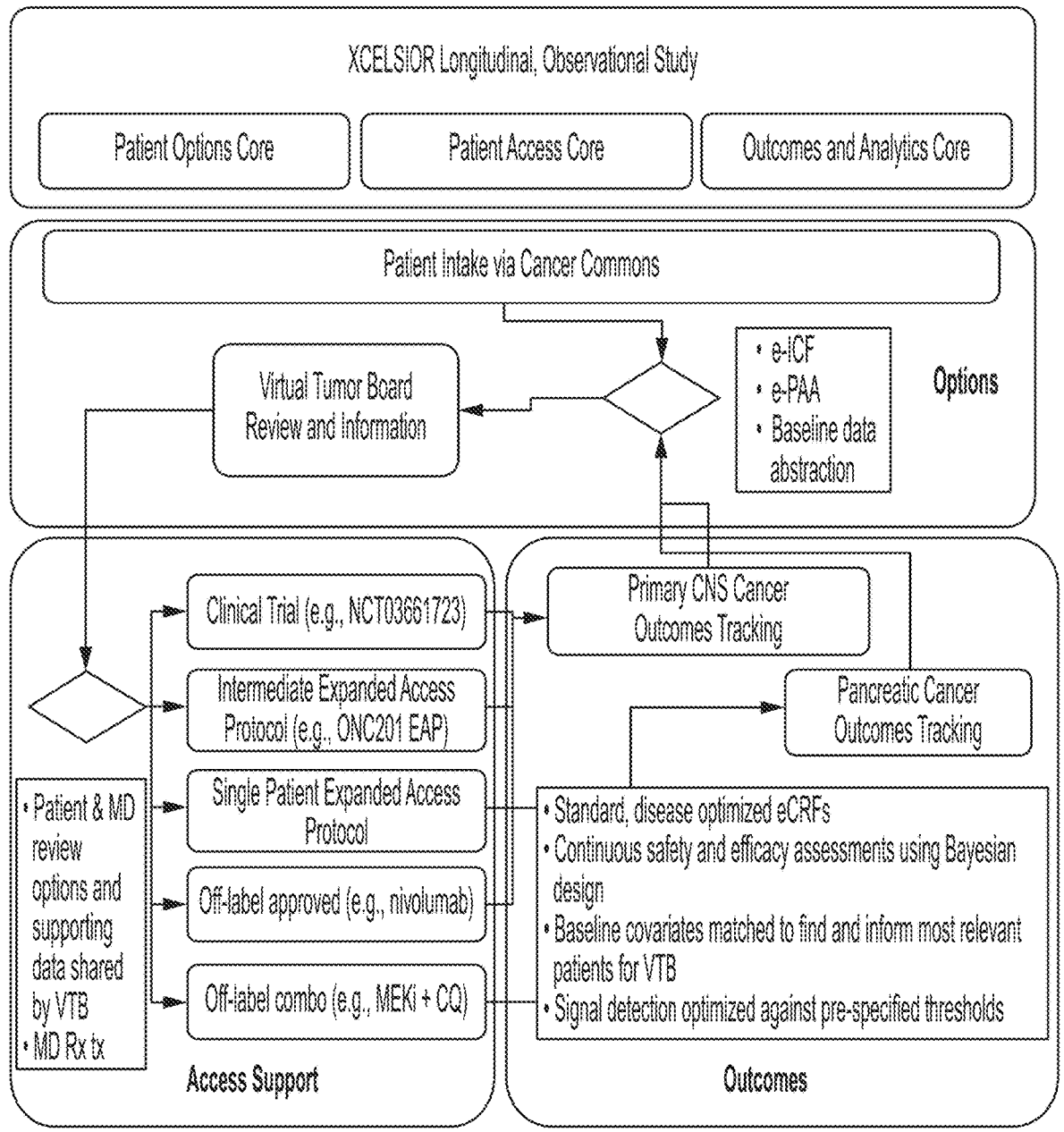
FIG. 19 shows an example of a flowchart for such a longitudinal, observational study.

Systems and methods of the present disclosure can be used to build a patient-centric registry for the registration of cancer patients, operations of a virtual tumor board, insight capture in clinical decision-making, and collection of longitudinal, observational data in a patient-centric cancer treatment and outcomes registry. FIG. 19 shows an example of a flowchart for such a longitudinal, observational study. Through this study, patient intake can occur through a web portal. This includes consent to participate in the data registry, including the collection and review of medical information by a Virtual Tumor Board (VTB), generation of patient-specific treatment options with supporting rationale, access to treatment access support services, and inclusion into a registry study that includes safety and efficacy outcomes tracking. Patients are treated and tracked in their original treatment setting, and the data generated form part of a systematic framework combining expert judgment with artificial intelligence to maximize information gain and improve treatment option set development for individual cancer patients. In some cases, the system or platform provides utilities that are used either to automatically rank the top options coming out of the VTB, based on factors such as information gain, or these utilities can be provided to the VTB so it can consider them in its own recommendations back to the treating physician. In cases when there is a lack of sufficient data for robust algorithmic or statistical analyses to rank options such as information gain, then the decision making is left to the VTB. Alternatively, when there is sufficient data, then the system or platform may provide its recommendations and/or calculated rankings to the treating physician. In some cases, the system or platform provides its recommendations and/or rankings without input from the VTB (e.g., when there is sufficient data for statistically significant differences in predicted outcomes between treatment options and/or rationales).

A goal of the patient-centric registry is to extend from just helping patients find and understand treatment options to a patient-centered system that can develop evidence for precision oncology. This study is an "always-on" data registry or "perpetual protocol" to continuously collect and analyze longitudinal information in a way that closes the learning loop for patients. This is the underlying data operations framework for the patient-centric registry. Second, the metadata that is generated during decisions about patient care is gathered and analyzed to continuously learn and incorporate new information that would partition and thereby narrow the search space for future treatment decision-making. The patient-centric registry accomplishes this through the Virtual Tumor Board (VTB) process which integrates and scales human experts with AI and machine learning. Together the system is continuously learning and incorporating new information that narrows the evidence gap of what factors predict which treatments are best for an individual patient.

The patient-centric registry can include capabilities such as one or more of: performing prospective interventional studies as part of an IRB-exempted observational registry trial; using arms-length VTBs to avoid ethical conflicts when matching patients to treatments for which the platform provide is being paid, and to promote responsible off-label drug use while maintain compliance with FDA regulations; bringing promising drugs to the attention of KOLs; using protocol amendments to add new PIs, sites, drugs, etc. in a short timeframe (e.g., in days or weeks, such as soon as a PI can be trained or access to a drug can be obtained).

In some embodiments, objectives of the patient-centric registry include: implementing a patient-centered, computer-enhanced learning model for optimizing treatment selection in precision oncology; improving access to precision medicine tests and therapies for patients with recalcitrant or advanced cancer; and collecting patient safety and effectiveness outcomes in a longitudinal, observation data registry.

In addition, further objectives of the patient-centric registry can include: developing analytic methods and tools for patient group structure modeling using artificial intelligence and machine learning; building an integrated system that combines machine learning with human experts from a Virtual Tumor Board (VTB) to generate customized patient treatment options; performing insight capture and analysis on the rationales underlying VTB recommendations and physician treatment decisions; developing methods that incorporate measures of patient goals and perspectives into cancer treatment option set development; tracking patient outcomes over time and using analytic signal detection tools that combine machine learning and human expertise to identify meaningful safety and efficacy signals; and developing new outcomes measures, systems, tools, and methods to advance patient-centered precision oncology.

The operations of the VTB are in many respects analogous to the tumor boards run at major cancer centers or molecular tumor boards. The VTB functions to provide individual information services to patients and their physicians. However, research can also be conducted on the decision-making process to understand the rationale underlying VTB recommendations in relation to the tracking of patient outcomes. Information derived from research on treatment rationales are available to the VTB to facilitate treatment option identification and associated outcomes as part of the overall learning process.

Figure 20:
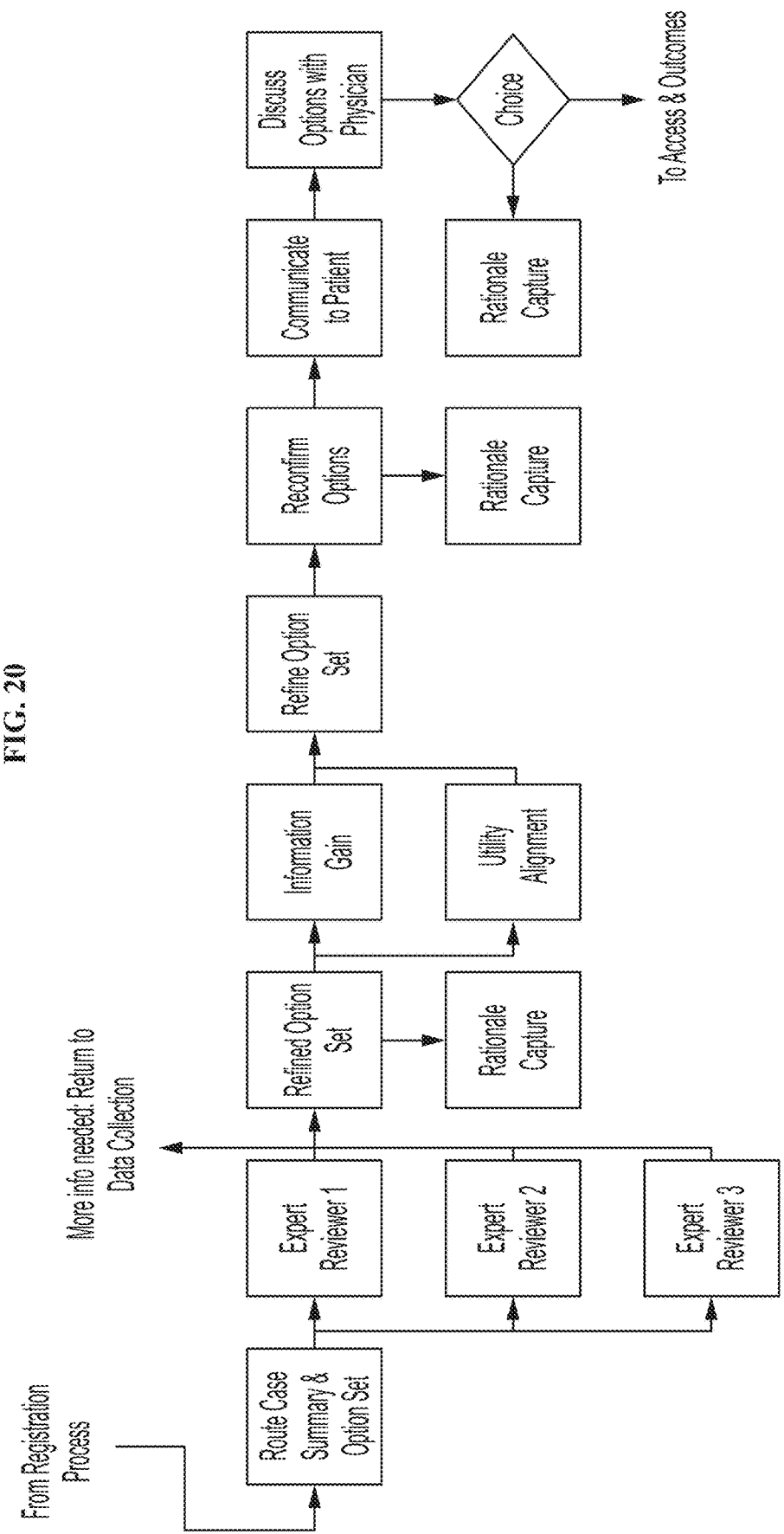
FIG. 20 shows a flowchart illustrating an embodiment of the Virtual Tumor Board (VTB) procedure.

FIG. 20 shows a flowchart illustrating the Virtual Tumor Board (VTB) procedure, which can be implemented as follows. Following registration and consent, the patient is contacted to begin collection and abstraction of their medical information into a patient summary to be provided to the VTB. This process includes identification of similar patients' medically-logical treatment options, including clinical trials, that have been suggested by the VTB for similar patients or have otherwise been identified as medically logical for similar patients, with relevant information from the study Leaderboard, if available. The completed summary is then submitted to at least three VTB members selected based on their availability and expertise for review. The VTB using will review the case, options, and discuss using on- or off-line technology support, to reduce the options into a list of best options at clinical equipoise. Rationale capture for addition, inclusion, or removal is collected for global learning analysis. Additional rounds of review and discussion may be undertaken to further refine the option list and VTB members may request additional information, including review of source records, to support their review. Once the option set is reduced the patient utility is applied and simulation analysis is run to assess the global information gain value of the options in the equipoise set. Together, these are provided to the VTB to determine whether they then wish to update their selection of options. Finally, the refined option list, with supporting information and rationales, plus information gain value and alignment with patient preference are provided to the patient and their doctor for consideration.

Information gain can be evaluated in various models such as, for example, decision trees. The Kullback-Leibler divergence can be used as a measure of how one probability distribution is different from a reference probability distribution. Thus, it can be used to determine the amount of information gained about a variable from observing another variable. For example, in decision trees, the Kullback-Leibler divergence can refer to the conditional expected value of the Kullback-Leibler divergence of the univariate probability distribution of a first variable from the conditional distribution of a second variable.

In some embodiments, the VTB can incorporate a utility assessment into treatment recommendations provided by the VTB (a virtual molecular tumor board), and relate utility with uncertainty and global information gain. Such an approach can equate treatment uncertainty with treatment outcomes variance, while recognizing that overlap of variance among treatment options equates to clinical equipoise. In general, cancer patients are risk-seeking, which equates to options with higher variance. Further, high-risk, high-variance options provide the greatest system-wide information gain. Therefore, the VTB can use a patient-utility questionnaire to inform the VTB about whether or not their patient-specific treatment suggestion aligns with the patient's risk tolerance.

The purpose of the patient-centric registry includes developing methods, systems, and algorithms for effectiveness and safety signal detection to improve treatment of cancer patients. Various endpoints are tracked to identify signals of effectiveness or safety based on composite clinical, symptomatic, and other measures of patient disease burden and treatment response collected in routine clinical practice and directly from the patients. Examples include physician-reported Karnofsky or ECOG performance status, and patient-reported quality-of-life rating scales for the primary disease, such as the EORTC QLQ BN20 or MDASI-BT for brain tumors and the QLQ-PAN26 for pancreatic tumors. Other patient-reported outcomes may be developed and used as part of the methods development of this study, such as patient statements and communications about their disease symptoms or functional status, photo and video submissions, supporting assessment of treatment effects, or other patient submitted information may provide value for identifying treatment response or nonresponse and may be used as generalizable patient-reported outcomes that provide measures of cancer symptoms.

Analysis of effectiveness can be measured using responder analysis of composite clinical, functional, or symptomatic endpoints to accommodate the wide heterogeneity in disease burden and symptomatology in late-stage and recalcitrant cancer patients. As a patient-centric registry, patients themselves may propose, suggest, and/or submit evidence or ideas for functionally relevant outcomes in their disease for further development and implementation. Additional endpoints for safety/tolerability and effectiveness are derived from real-world data collected during routine care augmented as necessary with supplemental information from the patient or their physician with blinded reviews, as necessary, to relate information to measures collected in traditional clinical trials. These may include, but are not limited to, CTCAE grade 3 or worse events, Time-to-progression (TTP), time-to-treatment failure (TTF), Complete Response (CR), Durable Response (DR), Response Rate (RR), Progression Free Survival (PFS) at relevant intervals, and Overall survival (OS). Endpoints may incorporate composite clinical, imaging, and laboratory markers developed as indicators of treatment response or failure.

Key inclusion criteria may include, for example, one or more of: both male and female patients with known or suspected recalcitrant or advanced cancer; patients with any performance status, comorbidity, or disease severity; and patients or their legally-authorized representative who are willing and able to provide written, informed consent (and assent, if applicable).

Figure 21:
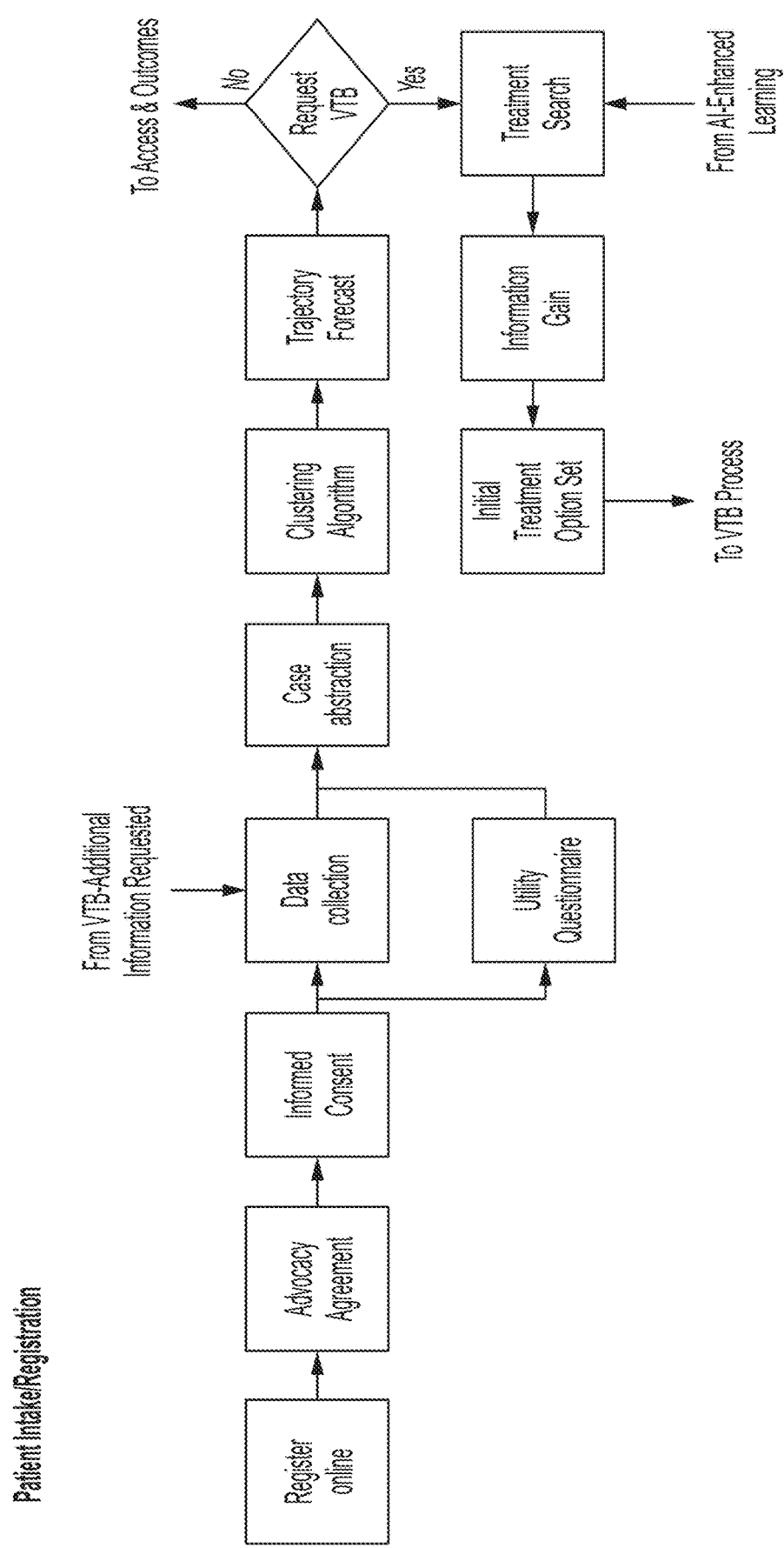
FIG. 21 shows a flow diagram illustrating a patient intake and registration procedure.

All patients that meet the inclusion criteria and complete the sign-up process on-line are enrolled into the registry. Those patients with specific sub-types of recalcitrant or advanced cancer, such as primary brain tumors or pancreatic adenocarcinoma, will be part of disease-specific sub-studies, which will include collection of measures specific to and appropriate for their disease. FIG. 21 shows a flow diagram illustrating a patient intake and registration procedure.

The patient-centric registry can be a real-world data registry. The primary site enrolls patients over the Web using patient-provided and patient-authorized remote collection of medical information from their medical records. The patient-centric registry can be a non-interventional data registry. Information about treatments, treatment decisions and rationale, and patient outcomes including safety and effectiveness of anti-cancer therapy and associated supportive care are collected for analysis.

Since it is well established that measured outcomes like the location of tumor and age of onset correlate strongly with molecular features in some tumor types, machine learning approaches can effectively be used toward understanding the hidden relationships between these types of data in order to build a model of patient groups. The patient-centric registry can use Bayesian NP clustering to provide a mechanism to fit patients to clusters without needing the same or even a complete set of data for all patients. This technique allows the mapping of a new and different dataset on to clusters produced from another dataset. For example, using registry data from a partner, a cluster model can be produced and new registry data from patients collected under this protocol can be fitted to existing groupings, while also informing and updating the group structure.

The patient-centric registry can be used to conduct an aggregated n-of-1 study design for assessment of drug safety and efficacy through individually-patient optimized treatments. Such n-of-1 studies can be aggregated into a large database with AI- and ML-based tools to analyze them. Such approaches are appropriately applied toward cancer treatment and management, especially in contexts where prior information about a drug's effectiveness exists for other types of tumors or based on molecular markers. The availability of such strong prior information invites a Bayesian model for assessing consecutive instances of treatment and response. Such aggregating n-of-1 experiments in oncology can be performed to achieve goals of personalized medicine.

While traditional n-of-1 studies have involved both blinding and randomization of the treatment sequence (A then B or B then A, denoted AB or BA, for example) this approach is less practical in oncology. However, statistical methods can be applied to aggregate and analyze individual patient treatment experiences. For example, Bayesian hierarchical methods can be used in relation to other meta-analysis approaches, including mixed-effects regression models to combine N-of-1 trials and assess the impact of outliers, missing-data, and parametric versus non-parametric assumptions of variance to build robust estimates of treatment effects and compare those results to data from a large, multicenter RCT. For example, such approaches can provide support for reimbursement approval for an off-label use of an approved drug in a rare disease population.

Randomization and blinding, while helpful for certain aspects of clinical trial validity in n-of-1 designs are not required for the aggregation or meta-analysis of data and statistical inference thereof, nor are they essential for making inferences about the effectiveness of cancer treatments. As noted in the FDA Guidance on Clinical Trial Endpoints for the Approval of Cancer Treatments, Objective Response Rate and Complete Response can both serve as approvable endpoints in single-arm, open-label cancer studies. Within the patient-centric registry study framework, use of internal controls, such as pre-specified estimates for patient trajectory based on individual characteristics, for example TTP ratio, enable a prospective evaluation of effectiveness with each patient as their own control, the result of which can be aggregated using Bayesian or other meta-analytic methods. This approach is especially powerful in rare diseases, which is a useful model for precision oncology, in which NGS data with other baseline covariates places each patient into at most, a very small cluster of similar patients. The important goal of looking for large effect sizes in rare diseases is a key aspect of signal detection in precision medicine generally and for the patient-centric approach specifically.

Figure 22:
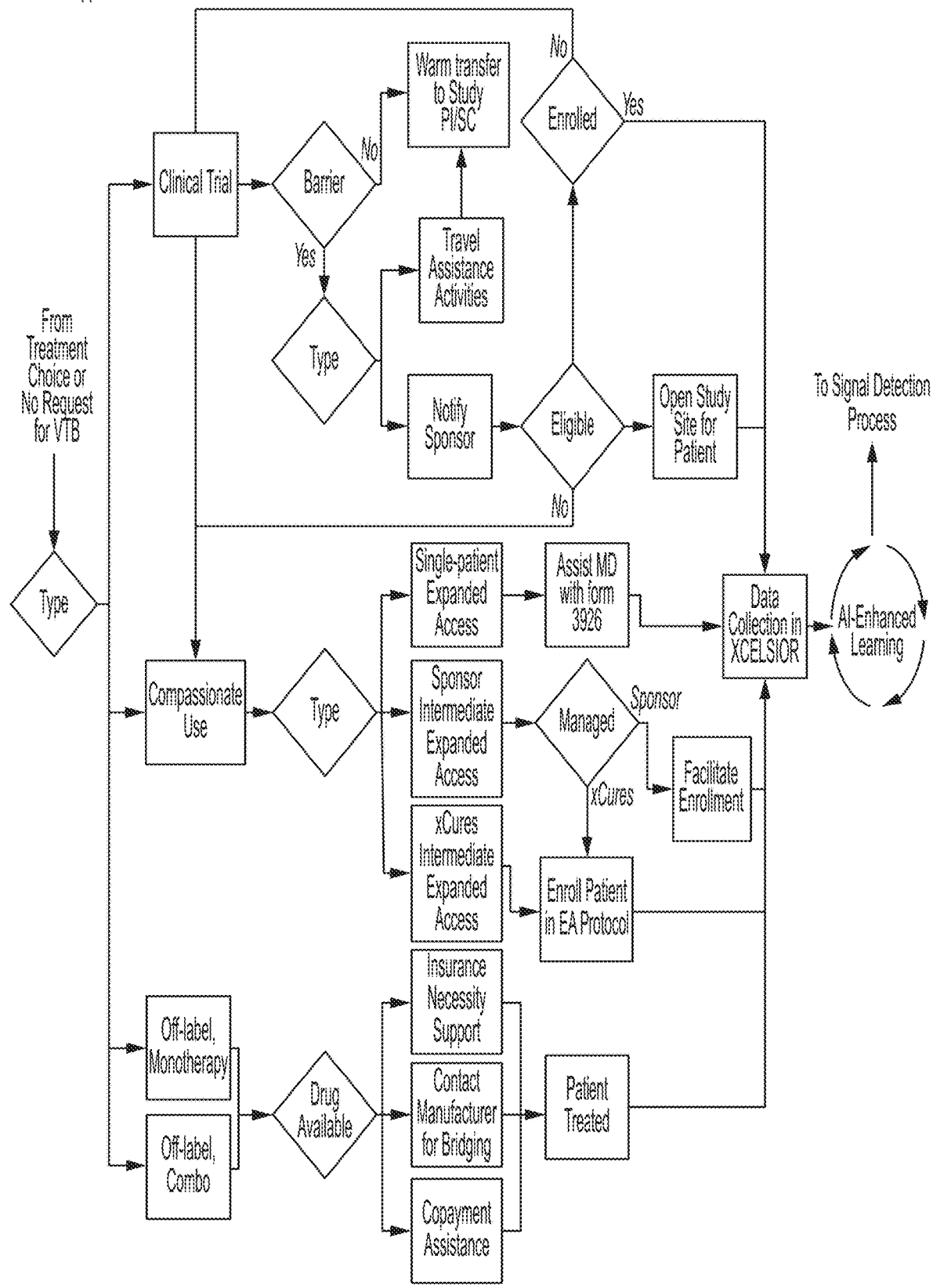
FIG. 22 shows a flowchart illustrating a patient access support procedure.

The patient-centric registry can provide treatment access support services to patients. FIG. 22 shows a flowchart illustrating a patient access support procedure. Commercially available drugs may be received directly from sponsors or manufacturers for the purposes of providing expedient treatment access services to patients. For example, sponsors may provide a supply of approved drugs to be stored at a central pharmacy, which may then provide matched therapies to sites designated for administration to specific patients participating in the patient-centric registry study. This process is envisioned in two primary ways. First, sponsors may provide drugs for patients either as bridging therapy, enabling patients to start treatment rapidly without concerns about payment while patients' physicians facilitate obtaining insurance coverage due to medical necessity. It is expected that within about two months of bridging therapy, information related response through clinical, imaging, or laboratory testing is developed and forms the basis of support for effectiveness in a specific patient. This information supports insurance coverage without delaying the start of treatment. In addition, analytic methods are incorporated to demonstrate effectiveness in similar patients based. Second, sponsors may provide drug directly out of altruism, or in exchange for access to de-identified data that improves their understanding about which patient characteristics correlate with effectiveness. In addition, patients receive assistance in enrolling in co-payment support programs.

Treatment access support services are provided to patients to facilitate availability of treatment options to patients and their doctors. In the event that provision of access to therapies involves investigational treatments, such treatments is administered by the patient's physician under an approved IND and study protocol specific for the use of such treatments that is distinct from the patient-centric data registry.

Figure 23:
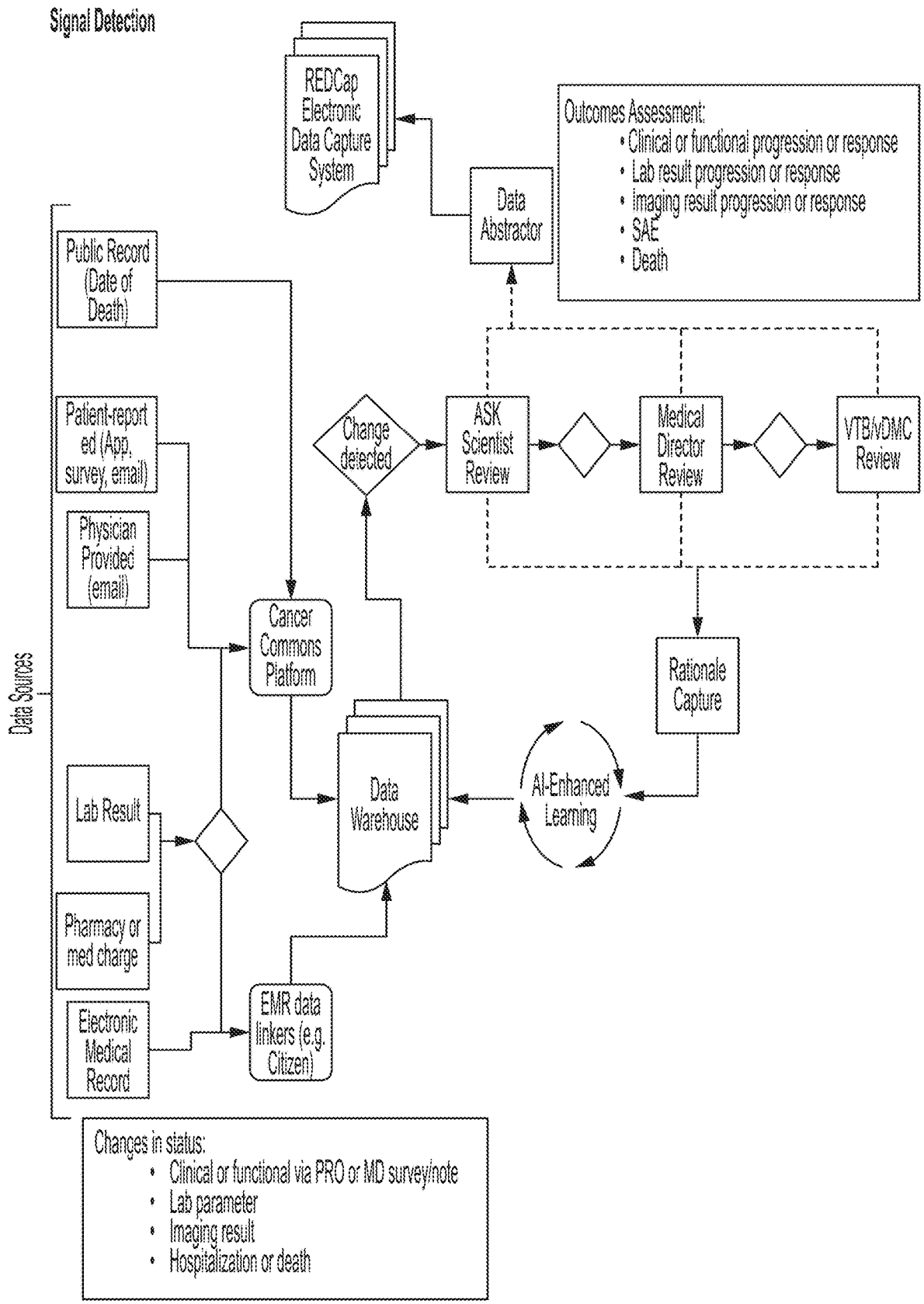
FIG. 23 shows a flowchart illustrating a signal detection procedure.

The patient-centric registry can provide signal detection activities, which are based on composite endpoints as well as outcomes in relation to a baseline trajectory forecast. FIG. 23 shows a flowchart illustrating a signal detection procedure. Because patients such as those with late-stage and recalcitrant cancers have no proven options and only a short time in which to explore options, the patient-centric registry aims to rapidly assess signals of effectiveness and safety or tolerability through composite assessment of changes in direction, magnitude, or rate of change in labs, images, disease symptoms, patient functioning, side effects, and/or changes in pharmacotherapy. Analytic methods, including traditional methods and machine learning based methods, may be used to identify and assess changes in status, which are combined with human expert judgment to evaluate and classify signals.

The patient-centric approach to precision oncology enables rapid global learning from every patient treatment. First, patients from anywhere can sign up for the service, which includes curation of their case by a cancer biologist and presentation to the VTB. Tools and techniques from artificial intelligence and machine learning help refine potential treatment options and analyze expert rationales, incorporate patient preferences for treatment, and present that information to the patient and their physician. Decisions about patient care remain with the patient and their doctor. Access to the platform is provided to the patient to track and analyze decisions, outcomes, and the associated metadata. Information gained from routine care is then maximized according to theories and algorithms that are well developed in search engine optimization, but less common in medicine. The platform uses machine learning and artificial intelligence to help integrate, assess, and inform clinicians and VTB experts while putting patients at the center of the process.

Precision medicine in oncology requires new approaches to generate information with the explicit goal of identifying the best treatment options for each individual patient. This will require integration of AI and machine learning with human cancer experts to identify treatment options, ensure access to those options, and evaluate the outcomes of therapy for patients through collection of disease-specific data in a group of large, patient-focused registries. A goal of the patient-centric registry is to pioneer the use of these approaches to generate actionable insights that will improve outcomes for late-stage cancer patients through better treatment selection, promote rapid learning about optimal treatments for specific subgroups of patients, and quickly share information to maximize the outcomes for cancer patients everywhere.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computing platform comprising one or more processors configured to provide: (a) a clinical case capture tool comprising: (i) a software module for presenting a plurality of selectable clinical case templates, each template comprising a plurality of adaptive clinical case parameters, each parameter comprising one or more selectable values; (ii) a software module for receiving user input pertaining to at least one template, parameter, and value to capture a clinical case of a patient; and (iii) a software module for generating a summary of a captured clinical case, the summary comprising at least one treatment rationale for the patient; (b) a clinician survey application comprising: (i) a software module for publishing the summary of the captured clinical case to an expert clinician network; (ii) a software module for collecting peer review feedback pertaining to a treatment rationale of the summary; and (iii) a software module for storing a plurality of peer reviewed treatment rationales to form a knowledge base; and (c) a clinical decision engine comprising: (i) a software module for receiving user input to identify a cohort and a treatment hypothesis; (ii) a software module for applying a machine learning algorithm utilizing the knowledge base to provide one or more ranked treatment protocols based on predicted outcomes, wherein the software module conducts a Bayesian decision process to prioritize the one or more ranked treatment protocols in order to coordinate treatment decisions across a plurality of patients, wherein the Bayesian decision process prioritizes the one or more ranked treatment protocols based at least in part on (1) an efficacy of the one or more ranked treatment protocols, and (2) a variance or uncertainty of an efficacy of a n equipoise set of the one or more ranked treatment protocols, and wherein the Bayesian decision process prioritizes the equipoise set based at least in part on relative amount of information gained from the predicted outcomes across the equipoise set; and (iii) a software module for providing a registry for collecting outcome data of the captured clinical case to update the knowledge base, wherein the machine learning algorithm is trained using the updated knowledge base comprising a training data set comprising a plurality of input features and the outcome data of the captured clinical case.

2. The computing platform of claim 1, wherein the clinical case capture tool further comprises a treatment explorer generating ranked treatment options based on clinical case information.

3. The computing platform of claim 1, wherein the clinician survey application further comprises a software module for conducting an adaptive Delphi survey process.

4. The computing platform of claim 1, wherein the Bayesian decision process utilizes a Bayesian network or a hill climbing algorithm.

5. The computing platform of claim 1, wherein the clinical decision engine further comprises a software module for receiving user selection of the cohort based on one or more of: data source, age, gender, at least one biomarker, genetic variant, tumor type, cancer stage, tumor location, lymph node status, treatment, treatment order, desired evidence threshold, and survival.

6. The computing platform of claim 1, wherein the clinical decision engine further comprises a software module utilizing peer reviewed treatment rationales to generate one or more inferential chains that comprise at least one treatment hypothesis.

7. A computing platform comprising one or more processors configured to provide: (a) a knowledge database comprising a plurality of clinical cases and treatment options and treatment rationales associated with the plurality of clinical cases; (b) a clinical case capture tool for capturing a clinical case; (c) a clinician survey application for publishing the clinical case to an expert clinician network and collecting feedback for one or more treatment options and associated treatment rationales for the clinical case; and (d) a clinical decision engine comprising a machine learning algorithm utilizing the knowledge database to provide a user with at least one recommendation of the one or more treatment options based on the feedback, wherein a Bayesian decision process is conducted to prioritize the one or more treatment options in order to coordinate treatment decisions across a plurality of patients, wherein the Bayesian decision process prioritizes the one or more ranked treatment protocols based at least in part on (1) an efficacy of the one or more ranked treatment protocols, and (2) a variance or uncertainty of an efficacy of an equipoise set of the one or more ranked treatment protocols, wherein the Bayesian decision process prioritizes the equipoise set based at least in part on relative amount of information gained from the predicted outcomes across the equipoise set, wherein the knowledge database is updated with outcome data for the captured clinical case, and wherein the machine learning algorithm is trained using the updated knowledge database comprising a training data set comprising a plurality of input features and the outcome data of the captured clinical case.

8. The computing platform of claim 7, wherein the one or more treatment options and associated treatment rationales are mined or crowd-sourced from peer reviewed literature, conferences, medical data, a physician for the clinical case, an expert in a disease profile of the clinical case, or any combination thereof.

9. The computing platform of claim 7, wherein the at least one recommendation comprises a ranking of the one or more treatment options.

10. The computing platform of claim 7, wherein the clinical case capture tool further comprises a software module for converting user input from a Controlled Natural Language (CNL) into a formal logic.

11. The computing platform of claim 7, wherein the clinical case capture tool further comprises parameters and values selected from Controlled Natural Language (CNL), Biomedical Controlled English (BCE), or a combination thereof.

12. The computing platform of claim 7, wherein the clinician survey application further comprises a software module for conducting an adaptive Delphi survey process.

13. The computing platform of claim 7, wherein the clinician survey application further comprises a software module for converting the plurality of peer reviewed treatment rationales from a Controlled Natural Language (CNL) into a formal logic.

14. The computing platform of claim 7, wherein the Bayesian decision process utilizes a Bayesian network or a hill climbing algorithm.

15. The computing platform of claim 7, wherein the clinical decision engine further comprises a software module for selecting the cohort based on one or more of: data source, age, gender, at least one biomarker, genetic variant, tumor type, cancer stage, tumor location, lymph node status, treatment, treatment order, desired evidence threshold, and survival.

16. The computing platform of claim 7, wherein the clinical decision engine further comprises a software module utilizing peer reviewed treatment rationales to generate one or more inferential chains that comprise at least one treatment hypothesis.

17. The computing platform of claim 16, wherein the one or more inferential chains are generated using a machine learning algorithm.

\* \* \* \* \*

UNITED STATES PATENT AND TRADEMARK OFFICE
CERTIFICATE OF CORRECTION

PATENT NO. : 11,887,738 B2
APPLICATION NO. : 16/934303
DATED : January 30, 2024
INVENTOR(S) : Jeffrey C. Shrager et al.

It is certified that error appears in the above-identified patent and that said Letters Patent is hereby corrected as shown below:

In the Claims

Claim 1, Line 31:
Replace "a n equipoise set of the one or more ranked treatment" with --an equipoise set of the one or more ranked treatment--.

Signed and Sealed this
Ninth Day of April, 2024

Katherine Kelly Vidal
*Director of the United States Patent and Trademark Office*